US009932564B2

(12) United States Patent
Matassov et al.

(10) Patent No.: US 9,932,564 B2
(45) Date of Patent: Apr. 3, 2018

(54) RECOMBINANT ISFAHAN VIRAL VECTORS

(71) Applicants: THE BOARD OF REGENTS OF THE UNIVERSITY OF TEXAS SYSTEM, Austin, TX (US); PROFECTUS BIOSCIENCES, INC., Baltimore, MD (US)

(72) Inventors: Demetrius Matassov, Forest Hills, NY (US); Rodion V. Gorchakov, Houston, TX (US); Stefan Hamm, Somers, NY (US); Rebecca Nowak, Campbell Hall, NY (US); Robert L. Seymour, Galveston, TX (US); John H. Eldridge, Bethel, CT (US); Robert B. Tesh, Galveston, TX (US); David K. Clarke, San Diego, TX (US); Theresa E. Latham, Mamaroneck, NY (US); Scott Weaver, Galveston, TX (US); Farooq Nasar, Albany, NY (US)

(73) Assignees: THE BOARD OF REGENTS OF THE UNIVERSITY OF TEXAS SYSTEM, Austin, TX (US); PROFECTUS BIOSCIENCES, INC., Baltimore, MD (US)

( * ) Notice: Subject to any disclaimer, the term of this patent is extended or adjusted under 35 U.S.C. 154(b) by 0 days.

(21) Appl. No.: 15/122,695

(22) PCT Filed: Feb. 27, 2015

(86) PCT No.: PCT/US2015/018156

§ 371 (c)(1),
(2) Date: Aug. 31, 2016

(87) PCT Pub. No.: WO2015/134332

PCT Pub. Date: Sep. 11, 2015

(65) Prior Publication Data

US 2017/0067027 A1 Mar. 9, 2017

Related U.S. Application Data

(60) Provisional application No. 61/946,734, filed on Mar. 1, 2014.

(51) Int. Cl.

| | |
|---|---|
| *C12N 7/00* | (2006.01) |
| *A61K 39/12* | (2006.01) |
| *C12N 15/86* | (2006.01) |
| *A61K 39/21* | (2006.01) |
| *A61K 39/00* | (2006.01) |

(52) U.S. Cl.

CPC ................ *C12N 7/00* (2013.01); *A61K 39/12* (2013.01); *A61K 39/21* (2013.01); *C12N 15/86* (2013.01); *A61K 2039/5256* (2013.01); *A61K 2039/545* (2013.01); *C12N 2740/16071* (2013.01); *C12N 2740/16234* (2013.01); *C12N 2760/20221* (2013.01); *C12N 2760/20222* (2013.01); *C12N 2760/20243* (2013.01); *C12N 2760/20262* (2013.01); *C12N 2760/20271* (2013.01); *C12N 2770/36134* (2013.01); *C12N 2770/36171* (2013.01)

(58) Field of Classification Search

CPC ................................ C12N 7/00; C12N 15/86; C12N 2760/20222; C12N 2760/20243; C12N 2760/20221; C12N 2760/20234; C12N 2760/20271; C12N 2760/00032; C12N 2760/00034; C12N 2760/00071; C12N 2760/20232; C12N 2760/20244; C12N 2760/20251; C12N 2760/20262; A61K 39/12; A61K 2039/6075; A61K 2039/525; A61K 2039/5258; A61K 35/766; A61K 35/76; A61K 38/162; C07K 14/005

See application file for complete search history.

(56) References Cited

U.S. PATENT DOCUMENTS

| | | | | |
|---|---|---|---|---|
| 2012/0244113 A1 | 9/2012 | Eldridge et al. | ............. | 424/85.2 |
| 2013/0023032 A1 | 1/2013 | Clarke et al. | .............. | 435/235.1 |

FOREIGN PATENT DOCUMENTS

| | | |
|---|---|---|
| WO | WO/11/143650 | 11/2011 |

OTHER PUBLICATIONS

Martinez I, Wertz GW. Biological differences between vesicular stomatitis virus Indiana and New Jersey serotype glycoproteins: identification of amino acid residues modulating pH-dependent infectivity. J Virol. Mar. 2005;79(6):3578-85.*
Amara et al. J Virol. 2002, 76(15):7625-31.
Amara et al. "Control of a mucosal challenge and prevention of AIDS by a mulfiprotein DNA/MVA vaccine." Science. vol. 292, No. 5514, 2001, pp. 69-74.
Ball et al., PNAS. 1976, 73(2):442-6.
Ball, et al. 1999 J. Virol., 73:4705-12.
Chattopadhyay et al. J. Virol. 2013, 87:395-402.
Clarke et al., J Virol. Feb. 2007;81(4):2056-64.
Conzelmann, "Nonsegmented negative-strand RNA viruses: genetics and manipulation of viral genomes." Ann. Rev. Genet, vol. 32, No. 1, 1998, pp. 123-162.
Edgar, 2004. Nucleic Acids Research 32:1792-97.

(Continued)

*Primary Examiner* — Rachel B Gill

(74) *Attorney, Agent, or Firm* — Norton Rose Fulbright US LLP

(57) ABSTRACT

Certain embodiments are directed to recombinant *vesiculovirus* encoding a heterologous polynucleotide and methods of using the same.

25 Claims, 14 Drawing Sheets

(56) References Cited

OTHER PUBLICATIONS

Egan et al. "Priming with plasmid DNAs expressing interleukin-12 and simian immunodeficiency virus gag enhances the immunogenicity and efficacy of an experimental AIDS vaccine based on recombinant vesicular stomatitis virus." AIDS Research and Human Retroviruses. vol. 21, No. 7, 2005, pp. 629-643.
Felsenstein, 1989, Cladistics 5, 164-1663.
Finke et al. "Recombinant rhabdoviruses: vectors for vaccine development and gene therapy." Current Topics in Microbiology and Immunology. vol. 292, 2005, pp. 165-200.
Frank et al., Am J Vet Res. Jan. 1945:28-38.
Gaidamovich et al., "Natural foci of viruses borne by Phlebotomus papatasi in the USSR according to a serologic study of the population." Voprosy Virusologii. 1978, (5):556-60.
Gallione et al., 1981 J. Virol. 39:529-35.
Gouy et al., 2010, Molecular Biology and Evolution 27:221-24.
Hanke et al. J Virol. 1999, 73(9):7524-32.
International Preliminary Report on Patentability in International Application No. PCT/US2015/018156 dated Sep. 15, 2016.
International Search Report and Written Opinion in International Application No. PCT/US2015/018156 dated Jun. 5, 2015.
Jones et al. "Live attenuated recombinant vaccine protects nonhuman primates against Ebola and Marburg viruses." Nature Medicine. vol. 11, No. 7, 2005, pp. 786-790.
Kahn et al. Journal of Virology. 2001, 75(22):11079-87.
Kapadia et al. Virology. 2005, 340(2):174-82.
Marriott, "Complete genome sequences of Chandipura and Isfahan vesiculoviruses." Arch Virol. vol. 150, No. 4, 2005, pp. 671-680.
Olitsky et al., Journal of Experimental Medicine. 1934, 59:159-71.
Powers et al. "Changing patterns of chikungunya virus: re-emergence of a zoonotic arbovirus." J. Gen. Virol. 88, 2007, pp. 2363-2377.
Powers. "Risks to the Americas associated with the continued expansion of chikungunya virus." J. Gen. Virol. vol. 96, 2015, pp. 1-5.
Ramsburg et al. Journal of Virology. 2004, 78(8):3930-40.
Rao et al., "A large outbreak of acute encephalitis with high fatality rate in children in Andhra Pradesh, India, in 2003, associated with Chandipura virus." Lancet. vol. 364, No. 9437, 2004, pp. 869-874.
Reed et al., 2004 The Journal of Infectious Diseases 189:1013-1017.
Reed et al., 2005 The Journal of Infectious Diseases 192:1173-1182.
Reed et al., 2007 The Journal of Infectious Diseases 196:441-450.
Reuter et al. Journal of Virology. 2002, 76(17):8900-9.
Roberts et al., 1998, Virol., 247:1-6.
Roberts et al. J Virol. 1998, 72(6)4704-11.
Roberts et al. Journal of Virology. 1999, 73(5):3723-32.
Rose and Gallione, 1981, J. Virol. 39, 519-28.
Rose et al. Cell. 2001, 106(5):539-49.
Rose et al. Journal of Virology. 2000, 74(23):10903-10.
Sabin et al., Journal of Experimental Medicine. 1937, 66:15-34.
Schlereth et al., 2000 J. Virol, 74:4652-57.
Schwartz et al. "Biology and pathogenesis of chikungunya virus." Nature Rev. Microbiol. vol. 8, No. 7, 2010, pp. 491-500.
Strauss et al. Microbiol. Rev. 1994, 58:491-562.
Tesh et al. "Isfahan virus, a new vesiculovirus infecting humans, gerbils, and sandflies in Iran." The American journal of tropical medicine and hygiene. vol. 26, No. 2, 1977, pp. 299-306.
Tesh et al., "Ecologic studies of vesicular stomatitis virus. I. Prevalence of infection among animals and humans living in an area of endemic VSV activity." Am. J. Epidemiol., vol. 90, No. 3, 1969, pp. 255-261.
Villarreal et al., "Determination of molar ratios of vesicular stomatitis virus induced RNA species in BHK21 cells." Biochemistry. vol. 15, No. 8, 1976, pp. 1663-1667.
Weaver et al., "Venezuelan equine encephalitis." Annu. Rev. Entomol. vol. 49, No. 1, 2004, pp. 141-174.
Wilks et al., J Hyg (Lond). 1986, 97(2):359-68.
Witko et al., "An efficient helper-virus-free method for rescue of recombinant paramyxoviruses and rhadoviruses from a cell line suitable for vaccine development." J Virol Methods. vol. 135, No. 1, 2006, pp. 91-101.
Xu et al. Journal of Virology. 2009, 83(19):9813-23.

* cited by examiner

```
Chandipura N        ...mmtpgqqeidqadsympylidmglstkspyssstknp...
Piry N              ...mmtpgqeidkadsympylidfglstkspyssvknp...
Cocal N             ...mmypgqeidksdsympylidlglsqkspystvknp...
VSV Alagoas N       ...mmkpgqeidkadsympylidfglsqkspystvknp...
Spring Viraemia     ...mmkpgqeidkstsympylidmgisakspystiknp...
Vesiculo Pike Fr    ...mmkpgqeidngasympylidmgisakspystiknp...
VSVnj N             ...mmypgqeidkadsympymidfglsqkspyssvknp...
VSVi N              ...mmlpgqeidkadsympylidfglsskspyssvknp...
ISF N               ...mmkerqevdkadsympylidfgistkspyssvknp...
                                      ↓↓      ↓   ↓

ISF N*              ...mmkerqevdqsdsympymidmgistkspyssvknp...
                                qs       m   m
```

FIG. 11 rVSVin N4CT1 (HIVgag-SDE)1 = rVSV-HIV-106 rISF-N4ΔG-(VSVnj G TMiCT1 mod)5-(HIV-1 gag-SDE)1 = rISF-HIV-016

**rISF-N*4GΔCT25-(HIV-1 gag-SDE)1 = rISF-HIV-018**

N*: The ISF N protein is a slightly modified form of the wild-type Isfahan protein:
A strong T cell epitope for mice has been changed (K271Q, A272S, L279M, F282M).

FIG. 12

| Group # | # mice | Vaccine | Vaccine dose | Route |
|---|---|---|---|---|
| 1 | 5 | rVSV$_N$ N4CT1 (HIVgag-SDE)1 (rVSV-HIV-106) | $10^7$ pfu | I.M |
| 2 | 5 | rSF-N4ΔG-(VSV$_N$ G TMlCT1 mod)S-(HIV-1 gag-SDE)1 (rSF-HIV-016) | $10^7$ pfu | I.M |
| 3 | 5 | rSF-N*4GΔCT2S-(HIVgag-SDE)1 (rSF-HIV-018) | $10^7$ pfu | I.M |

Prime ↓ 0 ──────────────── 10 Days

Immunol Assays: Gag and VSV N peptides spec. IFNg Elispot;

FIG. 13

HIV-1 Gag Dominant Epitope Specific IFNg ELISPOT Responses

VSV-N Specific IFNg ELISPOT Responses

Conclusion: 1) the two rSF candidates elicited similar Ag specific CMI, slightly lower than those from rVSV.
2) rSF N* mutation reduces the cross responses to rVSV N. It may benefit the prime/boost.
Further test it in MuO62b.

FIG. 14 rISF-N4GΔCT25-(HIV-1 gag-SDE)1 = rISF-HIV-015
rISF-N*4GΔCT25-(HIV-1

FIG. 18

RECOMBINANT ISFAHAN VIRAL VECTORS

PRIORITY

This application claims priority to U.S. Provisional Patent Application Ser. No. 61/946,734 filed Mar. 1, 2014, which is incorporated herein by reference in its entirety.

STATEMENT REGARDING FEDERALLY FUNDED RESEARCH

This invention was made with government support under N01-AI-30027, HHSN272201000040I, and HHSN2720004/D04 awarded by the National Institutes of Health/National Institute of Allergy and Infectious Disease. The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

Recombinant vesicular stomatitis virus (rVSV) has been developed as a vector platform for a range of human pathogens (Finke and Conzelmann. *Current Topics in Microbiology and Immunology.* 2005, 292:165-200; Jones et al. *Nature Medicine.* 2005, 11(7):786-90; Kahn et al. *Journal of Virology.* 2001, 75(22):11079-87; Kapadia et al. *Virology.* 2005, 340(2):174-82; Reuter et al. *Journal of Virology.* 2002, 76(17):8900-9; Roberts et al. *Journal of Virology.* 1999, 73(5):3723-32; Roberts et al. *J Virol.* 1998, 72(6):4704-11; Rose et al. *Cell.* 2001, 106(5):539-49), and an optimized rVSV vector expressing HIV-1 gag protein has completed clinical evaluation (HVTN 090: accessible via the worldwide web at URL clinicaltrials.gov/). Despite these advances, challenges remain in the development of the rVSV vector platform, including potential immunity generated against vector proteins that may interfere with subsequent boosting immunizations with rVSV vectors. This potential problem may be overcome when rVSV vectors are used in heterologous prime-boost immunization regimens with other immunologically distinct vectors (Amara et al. *Science.* 2001, 292(5514):69-74; Amara et al. *J Virol.* 2002, 76(15):7625-31; Egan et al. *AIDS Research and Human Retroviruses.* 2005, 21(7):629-43; Hanke et al. *J Virol.* 1999, 73(9):7524-32; Ramsburg et al. *Journal of Virology.* 2004, 78(8):3930-40; Santa et al. *J Virol.* 2007; Xu et al. *Journal of Virology.* 2009, 83(19):9813-23). Serotype switching of rVSV vectors, achieved by swapping the surface G protein with that of a different vesiculovirus serotype, also enhances immunogenicity in prime-boost regimens in mice (Rose et al. *Journal of Virology.* 2000, 74(23):10903-10). However, cross-reactivity of cellular immune responses directed towards rVSV core proteins may limit this approach.

In view of these observations and potential limitations, there is a need for additional heterologous vectors for use either alone or in conjunction with rVSV vectors.

SUMMARY

Embodiments of the invention include immunogenic compositions and methods related to vesiculoviruses, such as Isfahan virus (ISFV) alone or in combination with vesicular stomatitis virus (VSV) and their use as therapeutics and/or prophylactics. Certain aspects include methods and immunogenic compositions comprising a recombinant vesiculovirus encoding one or more heterologous polypeptides. "Recombinant virus" refers to any viral genome or virion that is the same as or different than a wild-type virus due to a rearrangement, deletion, insertion, or substitution of one or more nucleotides in the wild-type viral genome. In particular, the term includes recombinant viruses generated by the intervention of a human. In certain aspects the vesiculovirus is a recombinant Isfahan virus (rISFV). In certain aspects the rISFV is a replication competent virus. As applied to a recombinant virus, "replication competent" means that the virus is capable of cell infection; replication of the viral genome; and production and release of new virus particles; although one or more of these characteristics need not occur at the same rate as they occur in the same cell type infected by a wild-type virus, and may occur at a faster or slower rate.

In a further aspect the rISFV comprises one or more of (i) an N protein having an amino acid sequence that is 90, 95, 98, or 100% identical to the amino acid sequence of SEQ ID NO:2, (ii) a P protein having an amino acid sequence that is 90, 95, 98, or 100% identical to the amino acid sequence of SEQ ID NO:3, (iii) an M protein having an amino acid sequence that is 90, 95, 98, or 100% identical to the amino acid sequence of SEQ ID NO:4, (iv) a G protein having an amino acid sequence that is 90, 95, 98, or 100% identical to the amino acid sequence of SEQ ID NO:5, or (v) an L protein having an amino acid sequence that is 90, 95, 98, or 100% identical to the amino acid sequence of SEQ ID NO:6.

Certain embodiments are directed to a rISFV comprising 4 or 5 of an N protein gene, a P protein gene, an M protein gene, a G protein gene, and an L protein gene. In certain aspects the rISFV further comprises a heterologous polynucleotide sequence encoding a heterologous polypeptide. In certain embodiments the rISFV further comprises a heterologous transcription unit (TU). A transcription unit refers to a heterologous polynucleotide sequence (a) flanked by a transcription start signal and a transcription stop signal (including a polyadenylation sequence), and (b) encoding one or more target heterologous polypeptide(s). In certain embodiments the heterologous TU is the $1^{st}$, $2^{nd}$, $3^{rd}$, $4^{th}$, $5^{th}$ or $6^{th}$ TU in the virus genome. In certain aspects the heterologous TU encodes two or more heterologous polypeptides. In other aspects two heterologous TUs are included in the virus genome, with one heterologous TU inserted into one position in the virus genome and the second heterologous TU inserted into a different position in the virus genome.

Another mechanism for expressing a heterologous polynucleotide sequence is to link the heterologous sequence to an ISF gene via a 2A peptide. The terms "2A", "2A peptide" or "2A-like peptide" refer to peptides that have been used successfully to generate multiple proteins from a single open reading frame. These peptides are small (18-22 amino acids) and have divergent amino-terminal sequences, but all contain a PGP motif at the C-terminus. Through a ribosomal skip mechanism, the 2A peptide prevents normal peptide bond formation between a glycine and a proline residue at the C-terminus of the peptide. These 2A and 2A-like sequences are known in the art and may be readily selected for such use. See, e.g., Szymczak-Workman et al, in Cold Spring Harbor Protocols 2012, doi 10.1101/pdb.ip067876; and Friedmann and Rossi (eds), Gene Transfer: Delivery and Expression of DNA and RNA, CSHL Press, Cold Spring Harbor, N.Y. USA, 2007, among others. One such 2A peptide is the peptide T2A, which is isolated from Thosea asigna virus and has the sequence EGRGSLLTCGDVEEN-PGP (SEQ ID NO:68). In further aspects an internal ribosome entry site (IRES) can be included in a gene encoding at least two polypeptides to enable cap independent transcription of the downstream coding region. A number of IRES sequence are known and can be selected from the IRESite database that is available on the worldwideweb at iresite.org.

In certain aspects the rISFV G gene encodes a G protein having a carboxy-terminal truncation, in particular a truncation of 20 to 25 amino acids. In certain aspects the rISFV genome comprises 3' to 5' an ISFV leader sequence, an ISFV P protein open reading frame (ORF), an ISFV M protein ORF, an ISFV G protein ORF, an ISFV N protein ORF, an ISFV L protein ORF, and an ISFV trailer sequence, together with the heterologous polynucleotide sequence or the heterologous TU at any position within the rISFV genome. In certain aspects the heterologous TU is located at position 5 of the rISFV genome. In certain aspects the heterologous polynucleotide encodes an immunogenic polypeptide. In other aspects the heterologous polynucleotide encodes one or more antigens. The antigen(s) can be a viral antigen, a bacterial antigen, a tumor-specific or cancer antigen, a parasitic antigen, or an allergen.

Certain embodiments are directed to a rISFV with a gene order, 3' to 5' relative to the (-) sense RNA, of N-P-M-G-L-(H), N-P-M-G-(H)-L, N-P-M-(H)-G-L, N-P-(H)-M-G-L, N-(H)-P-M-G-L, (H)-N-P-M-G-L, P-N-M-G-L-(H), P-N-M-G-(H)-L, P-N-M-(H)-G-L, P-N-(H)-M-G-L, P-(H)-N-M-G-L, (H)-P-N-M-G-L, P-M-N-G-L-(H), P-M-N-G-(H)-L, P-M-N-(H)-G-L, P-M-(H)-N-G-L, P-(H)-M-N-G-L, (H)-P-M-N-G-L, P-M-G-N-L-(H), P-M-G-N-(H)-L, P-M-G-(H)-N-L, P-M-(H)-G-N-L, P-(H)-M-G-N-L, (H)-P-M-G-N-L, P-M-G-L-N-(H), P-M-G-(H)-L-N, P-M-G-L(H)-N, P-M-(H)-G-L-N, P-(H)-M-G-L-N or (H)-P-M-G-L-N wherein (H) is a TU comprising at least one heterologous polynucleotide. In certain aspects the rISFV has a P-M-G-N-(H)-L gene order. In certain aspects the rISFV genome is encoded in an expression vector. In a further embodiment the expression vector is a DNA vector, e.g., a plasmid vector. The terms "gene shuffling", "shuffled gene", "shuffled", "shuffling", "gene rearrangement" and "gene translocation" are used interchangeably, and refer to an alteration in the order of the vesiculovirus genes in the viral genome.

Certain embodiments are directed to an expression vector encoding the recombinant negative sense RNA described above. In certain aspects the expression vector is a DNA vector.

Other embodiments are directed to a host cell comprising the expression vector described above. As used herein, the term "expression vector" is intended to include a plasmid or virus that is capable of synthesizing a heterologous polynucleotide sequence encoded by the vector. In certain aspects a vector can replicate and express an encoded nucleic acid.

Still other embodiments are directed to a virus particle comprising the recombinant RNA described above. As used herein a "virus particle" is an infective entity that provides a polynucleotide sequence encoding one or more polypeptides to be expressed in a host.

Immunogenic compositions can include virus particles comprising the recombinant nucleic acids described herein. Certain aspects are directed to methods of inducing an immune response in a subject comprising administering the immunogenic compositions described herein.

Methods and compositions of the invention can include a second therapeutic virus. A second virus can be selected from recombinant or oncolytic adenoviruses, vaccinia virus, Newcastle disease virus, herpes viruses, and rhabdoviruses. In other aspects, the composition is a pharmaceutically acceptable composition. In certain aspects the second therapeutic virus is an rVSV. In a further aspect the rVSV encodes the same antigen or a related antigen present in or on the same target cell or organism.

A recombinant vesiculovirus (e.g., rISFV as described herein) can be administered to a subject in need of a therapeutic or prophylactic immune response. Recombinant vesiculovirus compositions can be administered 1, 2, 3, 4, 5, 6, 7, 8, 9, 10 or more times with one or more recombinant vesiculoviruses. The composition administered can have 10, 100, 1000, $10^4$, $10^5$, $10^6$, $10^7$, $10^8$, $10^9$, $10^{10}$, $10^{11}$, $10^{12}$, $10^{13}$, $10^{14}$, or more viral particles or plaque forming units (pfu). Administration can be by the intraperitoneal, intravenous, intra-arterial, intratumoral (for solid tumors), intramuscular, intradermal, subcutaneous, oral, or intranasal route. In certain aspects, the compositions are administered systemically, particularly by intravascular administration, which includes injection, perfusion and the like.

The methods of the invention can further comprise administering a second anti-cancer or anti-microbial therapy. In certain aspects, a second anti-cancer agent is a chemotherapeutic, a radiotherapeutic, an immunotherapeutic, surgery or the like. In other aspects a second anti-microbial therapy is an antibiotic or an antiviral.

rISFV is serologically and phylogenetically distinct from rVSV. This distinction can be utilized to optimize the protective efficacy and immunogenicity of an immune stimulating regimen. rISFV and rVSV vectors can be employed in prime-boost regimens. A first recombinant vesiculovirus can be used in any number of combinations with a second recombinant vesiculovirus.

The term "providing" or "administering" is used according to its ordinary meaning "to supply or furnish for use." In some embodiments, an antigen is provided by direct administration (for example, by intramuscular injection), while in other embodiments, the antigen is effectively provided by administering a nucleic acid encoding the antigen. In certain aspects the invention contemplates compositions comprising various combinations of nucleic acid, antigens, peptides, and/or epitopes.

In certain aspects a viral particle, polypeptide, or nucleic acid can be an isolated viral particle, polypeptide, or nucleic acid. The term "isolated" can refer to a viral particle, nucleic acid, or polypeptide that is substantially free of cellular material, bacterial material, viral material, or culture medium (e.g., when produced by recombinant DNA techniques) of their source of origin, or chemical precursors or other chemicals (e.g., when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Other embodiments of the invention are discussed throughout this application. Any embodiment discussed with respect to one aspect of the invention applies to other aspects of the invention as well and vice versa. Each embodiment described herein is understood to be an embodiment of the invention that is applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one", but it is also consistent with the meaning of "one or more", "at least one", and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 1 is a maximum-likelihood phylogenetic tree of the genus *Vesiculovirus* based on nucleotide sequences of the N gene.

FIG. 2 depicts the restriction sites used in the cloning strategy for the generation of a complete Isfahan genomic cDNA clone.

FIG. 3A is a diagram of a rISFV vector [also designated rISFV-N4-G3-(VEEV ZPC E3-E1)5] encoding a Venezuelan equine encephalitis virus (VEEV) E3-E2-6K-E1 polyprotein; FIG. 3B is a Western blot depicting the expression of VEEV proteins (lane 3).

FIG. 4 is an alignment of the amino acid sequences of the N protein of various *vesiculoviruses*. (Isfahan, SEQ ID NO:71; VSV Indiana, SEQ ID NO:72; VSV New Jersey, SEQ ID NO:73; Chandipura, SEQ ID NO:74; Piry, SEQ ID NO:75; Cocal, SEQ ID NO:76; VSV Alagoas, SEQ ID NO:77; Spring viraemia, SEQ ID NO:78; vesiculo Pike, SEQ ID NO:79; and Sea trout Rhabdovirus, SEQ ID NO:80) Regions of amino acid homology are shaded.

FIG. 7 depicts the percent survival of mice immunized with rISFV-N4 [also designated rISFV-N4-G3-(VEEV ZPC E3-E1)5] expressing VEEV-strain ZPC E3-E1 proteins, followed by lethal challenge with VEEV-ZPC.

FIG. 8 depicts the percent survival of mice immunized with rISFV-N4 [also designated rISFV-N4-G3-(VEEV ZPC E3-E1)5] expressing VEEV-ZPC E3-E1 proteins at $10^8$ or $10^7$ pfu and rVSV Indiana serotype N4CT1 (rVSV$_{IN}$N4CT1) [also designated rVSV$_{IN}$-N4-G3-(VEEV ZPC E3-E1)5] expressing VEEV-ZPC E3-E1 proteins at $10^8$ or $10^7$ pfu, followed by lethal challenge with VEEV-ZPC.

FIG. 9 depicts the percent survival of mice immunized with rISFV-N4 expressing EEEV-FL93 E3-E1 proteins and rISFV-N4 expressing VEEV-ZPC E3-E1 proteins [together, also designated rISFV-N4G3-(VEEV ZPC E3-E1)5/rISFV-N4-G3-(EEEV FL93 E3-E1)5], followed by lethal challenge with EEEV-FL93.

FIG. 10 depicts the percent survival of mice immunized with rISFV-N4 expressing EEEV-FL93 E3-E1 proteins and rISFV-N4 expressing VEEV-ZPC E3-E1 proteins [together, also designated rISFV-N4G3-(VEEV ZPC E3-E1)5/rISFV-N4-G3-(EEEV FL93 E3-E1)5], followed by lethal challenge with VEEV-ZPC.

FIG. 11 illustrates the four amino acids that can be changed in the N protein sequence without negatively impacting biological function. A known epitope in BALB/c mice is underlined. The N protein sequences are from Chandipura, SEQ ID NO:81; Piry, SEQ ID NO:82; Cocal, SEQ ID NO:83; VSV Alagoas, SEQ ID NO:84; Spring viraemia, SEQ ID NO:85; Vesiculo Pike, SEQ ID NO:86; VSV New Jersey, SEQ ID NO:87; VSV Indiana, SEQ ID NO:88; Isfahan, SEQ ID NO:89; and mutant Isfahan, SEQ ID NO:90.

FIG. 12 illustrates recombinant viruses tested in the PBS-Mu-062a study.

FIG. 13 is a summary of the PBS-Mu-062a study design.

FIG. 14 illustrates interferon gamma (IFN-γ) ELISpot responses to an HIV-1 gag epitope in the PBS-Mu-062a study.

FIG. 15 illustrates rISFVs tested in the PBS-Mu-062b prime/boost study.

FIG. 16 is a summary of the PBS-Mu-062b study design.

FIG. 18 illustrates IFN-γ ELISpot responses to VSV-N in the PBS-Mu-062b study.

DESCRIPTION

Figure 5:
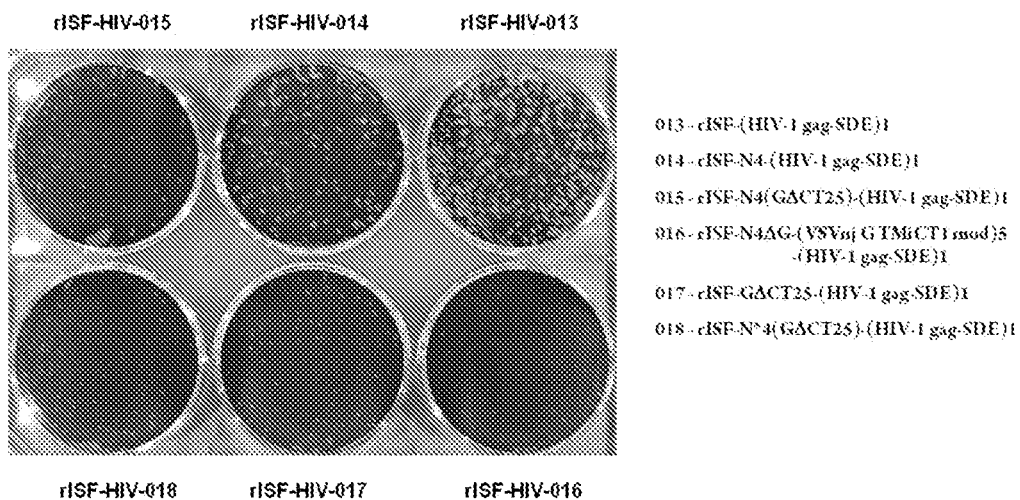
FIG. 5 is a photograph of observed plaque sizes generated by various rISFVs expressing a modified HIV-1 gag protein.

Isfahan virus (ISFV) and vesicular stomatitis virus (VSV) are members of the *Vesiculovirus* genus in the family Rhabdoviridae. The prototypical rhabdoviruses are rabies virus (RV) and VSV. The Rhabdoviridae is a family of bullet shaped viruses having single strand non-segmented (-) sense RNA genomes. There are more than 250 known Rhabdoviruses that infect mammals, fish, insects, or plants. The family comprises at least 5 genera: (1) Lyssavirus: including RV, other mammalian viruses, and some insect viruses; (2) Vesiculovirus: including VSV; (3) Ephemerovirus: including bovine ephemeral fever virus; (4) Cytorhabdovirus: including lettuce necrotic yellow virus; and (5) Nucleorhabdovirus: including potato yellow dwarf virus.

The rhabdovirus negative-sense viral RNA (vRNA) genome is approximately 11-15 kb in length with an approximately 50 nucleotide 3' leader sequence and an approximately 60 nucleotide non-translated 5' trailer sequence. Rhabdovirus viral genomic RNA (vRNA) generally contains 5 genes encoding 5 major proteins: nucleocapsid protein (N), phosphoprotein (P), matrix protein (M), glycoprotein (G), and large protein (L)(also known as the polymerase). Rhabdoviruses have a conserved polyadenylation signal at the 5' end of each gene and a short untranscribed intergenic region between each of the 5 genes. Typically these genes are in the order 3'-N-P-M-G-L-5' of the viral genome. The order of the genes dictates the levels of protein expression in the infected cell. Any manipulations of a Rhabdovirus genome to produce an infectious virus will typically include at least five transcription units (TU) encoding at least 4, and usually 5, of the major virus proteins to maintain the ability to infect and replicate at high levels.

I. Recombinant *Vesiculovirus*

*Vesiculovirus* genomes have been shown to accommodate more than one foreign gene spanning at least three kilobases (kb) of additional nucleotide sequence. *Vesiculovirus* vectors, which have been sufficiently attenuated (by, for example, gene shuffling and/or truncation of viral proteins), have demonstrated genetic stability, and the virus genome does not undergo detectable recombination. In addition, since viral replication is cytoplasmic, viral genomic RNA does not integrate into the host cell genome. Also, these negative-strand RNA viruses possess relatively simple, well-characterized transcriptional control sequences, which permit robust foreign gene expression. The level of foreign gene expression can be modulated by changing the position of the foreign gene relative to the single viral 3' transcription promoter (see, e.g., U.S. Pat. Nos. 6,136,585 and 8,287,878, among others). The 3' to 5' gradient of gene expression reflects the decreasing likelihood that the transcribing viral RNA-dependent RNA polymerase will successfully traverse each transcription stop/start signal encountered at gene junctions as it progresses along the genome template. Thus, foreign genes placed in proximity to the 3' terminal transcription promoter are expressed abundantly, while those inserted in more distal genomic positions, less so.

VSV replicates to high titers in a large array of different cell types, and viral proteins are expressed in great abundance. This not only means that VSV will act as a potent functional foreign gene expression vector, but also, that relevant rVSV vectors can be scaled to manufacturing levels in cell lines approved for the production of human biologicals. This replication-competent virus vector produces little to no disease symptoms or pathology in healthy humans, even in the face of substantial virus replication (Tesh, R. B. et al, 1969 *Am. J. Epidemiol.,* 90:255-61). Additionally human infection with, and thus pre-existing immunity to, VSV is rare. Therefore, rVSV is useful as a vector.

While a variety of rVSVs have been disclosed in the art with their genes "shuffled" to genome positions different from those of wild-type VSV (see U.S. Pat. Nos. 8,287,878; 6,596,529, and references cited therein), it may be useful for the N gene to be in the fourth position (N4) in the VSV gene order as part of a combination of mutations, so that the virus is sufficiently attenuated. In order to further attenuate rVSV, the cytoplasmic tail of the G protein may be truncated (G-CT).

Various embodiments of the rVSV described above employ VSV sequences derived from VSV serotype Indiana. However, other known vesiculoviruses (e.g., Isfahan virus) or VSV serotypes may be readily substituted for the exemplified sequences of the described embodiments given the teachings of this specification.

Suitable promoters for use in generating vectors described herein may be selected from constitutive promoters, inducible promoters, tissue-specific promoters and others. Examples of constitutive promoters that are non-specific in activity and employed in the expression of nucleic acid molecules of this invention include, without limitation, those promoters identified in International Patent Application No. WO2004/093906 and U.S. Pat. No. 8,287,878. The hCMV promoter is used to express VSV proteins for rVSV rescue purposes in a reverse genetics technique. Other pol II promoters that may be used include, inter alia, the ubiquitin C (UbiC) promoter, the phosphoglycerate kinase (PGK) promoter, the bovine cytomegalovirus (bCMV) promoter, a beta-actin promoter with an upstream CMV IV enhancer (CAGGS), and the elongation factor 1 alpha promoter (EF1A). In certain embodiments, the T7 RNA polymerase promoter is used.

Certain embodiments of the invention are directed to recombinant vesiculoviruses, including recombinant Isfahan virus (rISFV) alone or in combination with recombinant vesicular stomatitis virus (rVSV) for example in a prime/boost regimen, as well as vectors encoding recombinant vesiculoviruses and methods of using such recombinant vesiculoviruses and vectors. Recombinant vesiculoviruses can be produced (1) using cDNA transfections or (2) cDNAs transfected into a cell, which is further infected with a minivirus providing in trans the remaining components or activities needed to produce a recombinant vesiculovirus. Using any of these methods (e.g., minivirus, helper cell line, or cDNA transfection), the minimum components for producing a packaged RNA require an RNA molecule containing the cis-acting signals for (1) encapsidation of the genomic RNA by the N protein, and (2) replication of a genomic RNA equivalent.

A replicating element or replicon is a strand of RNA minimally containing at the 3' and 5' ends the leader sequence and the trailer sequence of a vesiculovirus; in the (-) sense genome, the leader is at the 3' end and the trailer is at the 5' end. RNA placed between these two replication signals can be replicated. The leader and trailer regions contain the minimal cis-acting elements for purposes of encapsidation by the N protein and for polymerase binding needed to initiate transcription and replication.

For any gene contained within a recombinant vesiculovirus genome, the gene can be flanked by the appropriate transcription initiation and termination signals that enable expression of those genes and production of encoded protein products. In particular, a heterologous polynucleotide is used, which is not encoded by the virus as isolated from nature or contains a coding region in a position, form, or context that is not naturally found in a virus.

A recombinant vesiculovirus for use as a therapeutic or an immunogenic composition can, in certain aspects, include rearranging the virus' gene order. In certain aspects the N gene is moved away from 3' promoter-proximal position, position 1. In a further aspect the N gene is moved to position 2, 3, 4, or 5. In certain aspects the N gene is at position 4 in the genome.

In certain embodiments the recombinant vesiculovirus comprises a heterologous polynucleotide. In certain aspects, a heterologous polynucleotide encodes an antigen. In other aspects the heterologous polynucleotide or polygene coding for the selected heterologous immune response-inducing antigen or antigens is located in position 1, 2, 3, 4, 5, or 6 of the gene order.

A. Recombinant *Vesiculovirus* Production

The transcription and replication of negative-sense, single stranded, non-segmented, viral RNA genomes are achieved through the enzymatic activity of a multimeric protein complex acting on the ribonucleoprotein core (nucleocapsid). The viral sequences are recognized when they are encapsidated by the N protein into the nucleocapsid structure. The genomic and antigenomic terminal promoter sequences of the nucleocapsid structure are recognized to initiate the transcriptional or replication pathways.

Thus, a genetically modified and attenuated recombinant vesiculovirus as described herein is produced according to rescue methods known in the art and more specifically as described in the examples below. Any suitable Isfahan virus, VSV strain or serotype may be used, including, but not limited to, VSV Indiana, VSV New Jersey, VSV Chandipura, VSV Glasgow, and the like. As described above, in addition to polynucleotide sequences encoding attenuated forms of Isfahan virus or VSV, the polynucleotide sequence also encodes heterologous polynucleotide sequences or open reading frames (ORFs) encoding a selected heterologous protein(s).

The typical (although not necessarily exclusive) circumstances for rescue include an appropriate mammalian cell in which T7 polymerase is present in the cell cytoplasm to drive transcription of the antigenomic (or genomic) single-stranded RNA from the viral genomic cDNA-containing transcription vector. Either co-transcriptionally or shortly thereafter, this viral anti-genome (or genome) RNA transcript is encapsidated into functional templates by the nucleoprotein and engaged by the required polymerase components produced concurrently from co-transfected plasmids expressing the required virus-specific trans-acting proteins. These events and processes lead to the prerequisite transcription of viral mRNAs, the replication and amplification of new genomes and, thereby, the production of novel vesiculovirus progeny, i.e., rescue.

The transcription and expression vectors are typically plasmid vectors designed for expression in the host cell. Expression vectors that comprise at least one isolated nucleic acid molecule encoding the trans-acting proteins necessary for encapsidation, transcription, and replication express these proteins from one expression vector or at least two different vectors.

A cloned DNA equivalent of a vesiculovirus genome can be placed between a suitable DNA-dependent RNA polymerase promoter (e.g., the T7 RNA polymerase promoter) and a self-cleaving ribozyme sequence (e.g., the hepatitis delta ribozyme), and inserted into a suitable transcription vector (e.g., a bacterial plasmid). This transcription vector provides a readily manipulable DNA template from which the RNA polymerase (e.g., T7 RNA polymerase) can faithfully transcribe a single-stranded RNA copy of the vesiculovirus cDNA with 5' and 3' termini. The orientation of the virus cDNA copy and the flanking promoter and ribozyme sequences determine whether anti-genome or genome RNA equivalents are transcribed. Also required for rescue of new vesiculovirus progeny are the vesiculovirus-specific trans-acting support proteins needed to encapsidate the naked, single-stranded anti-genome or genome RNA transcripts into functional nucleocapsid templates, and to start viral transcription and replication: the viral nucleocapsid (N) protein, the polymerase-associated phosphoprotein (P) and the polymerase (L) protein.

Briefly, one method of generating a recombinant vesiculovirus comprises introducing into a host cell a viral cDNA expression vector comprising a nucleic acid sequence described herein. In certain aspects, the expression vector comprises a T7 promoter upstream of position 1 ($P_1$), and a hepatitis delta virus ribozyme site (HDV Rz) and T7 terminator sequence downstream of the last position of a selected recombinant vesiculovirus nucleic acid sequence. The T7 promoter directs synthesis of viral RNA anti-genome transcripts from the expression vector when in the presence of the T7 RNA polymerase.

In some embodiments, the method further comprises transiently transfecting a host cell with a plasmid expressing the T7 RNA polymerase. In other embodiments, the method further involves co-transfecting the host cell with one or more plasmids expressing at least the viral proteins N, P, and L of a vesiculovirus (and optionally M and G). In some embodiments, these vesiculovirus proteins are expressed in the host cell using an RNA polII-dependent expression system. Other embodiments include steps such as heat-shocking the host cells containing the expression vector, T7 polymerase, and viral proteins of a recombinant vesiculovirus after plasmid DNA (pDNA) transfection. The transfected host cells or supernatant obtained from the transfected host cells may be transferred into a culture of fresh expansion cells. Assembled, infectious recombinant vesiculovirus can then be recovered from the culture.

In other aspects, a replication-competent recombinant vesiculovirus may be isolated and "rescued" using techniques known in the art (Ball, L. A. et al. 1999 *J. Virol.*, 73:4705-12; Conzelmann, 1998, *Ann. Rev. Genet.*, 32:123-162; Roberts and Rose, 1998, *Virol.*, 247:1-6). See, also, e.g., U.S. Pat. Nos. 8,287,878; 6,168,943; and 6,033,886; and International Patent Publication No. WO99/02657, each of which is incorporated herein by reference. Methods of producing recombinant RNA virus are referred to in the art as "rescue" or "reverse genetics" methods. Exemplary rescue methods for VSV are described in U.S. Pat. Nos. 6,033,886 and 6,596,529, and PCT publication WO 2004/113517, each incorporated herein by reference.

Additional techniques for conducting rescue of viruses such as VSV are described in U.S. Pat. No. 6,673,572 and U.S. publication number US2006/0153870, which are hereby incorporated by reference.

The host cells used in the rescue of vesiculoviruses are those that permit the expression from the vectors of the requisite constituents necessary for the production of recombinant vesiculovirus. Such host cells can be selected from a eukaryotic cell, such as a vertebrate cell. In general, host cells are derived from a human cell, such as a human embryonic kidney cell (e.g., 293). Vero cells, as well as many other types of cells are also used as host cells as described in the US patents and published application cited above. In certain embodiments, a transfection-facilitating reagent is added to increase DNA uptake by cells. Many of these reagents are known in the art (e.g., calcium phosphate, LIPOFECTAMINE® cationic lipid (Life Technologies, Gaithersburg, Md.) and EFFECTENE® cationic lipid (Qiagen, Hilden, Germany).

The rescued vesiculovirus is then tested for its desired phenotype (plaque morphology and transcription and replication attenuation), first by in vitro means. The vesiculovirus is also tested in vivo in an animal neurovirulence model. For example, mouse and/or ferret models are established for detecting neurovirulence. Briefly, groups of ten mice are injected intra-cranially (IC) with each of a range of virus concentrations that span the anticipated $LD_{50}$ dose (a dose that is lethal for 50% of animals). For example, IC inoculations containing virus at $10^2$, $10^3$, $10^4$ and $10^5$ pfu are used where the anticipated $LD_{50}$ for the virus is in the range $10^3$-$10^4$ pfu. Virus formulations are prepared by serial dilution of purified virus stocks in PBS. Mice are then injected through the top of the cranium with the requisite dose, in 25 µl of PBS. Animals are monitored daily for weight loss, morbidity and death. The $LD_{50}$ for a virus vector is then calculated from the cumulative death of mice over the range of concentrations tested.

To determine immunogenicity or antigenicity by detecting humoral immune responses, various immunoassays known in the art are used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immunoelectrophoresis assays, neutralization assays, etc. In one embodiment, antibody binding is measured by detecting a label on the primary antibody. In another embodiment, the primary antibody is detected by measuring binding of a secondary antibody or reagent to the primary antibody. In a further embodiment, the secondary antibody is labeled. In still another embodiment for detecting immunogenicity, T cell-mediated responses are assayed by standard methods, e.g., in vitro or in vivo cytoxicity assays, tetramer assays, ELISpot assays or in vivo delayed-type hypersensitivity assays.

The terms "isolation" or "isolating" a vesiculovirus means the process of culturing and purifying the virus particles from cellular debris and the like. One example would be to take the virus containing supernatant of a cell culture producing vesiculovirus and pass it through a 0.1-0.2 micron pore size filter (e.g., Millex-GS, Millipore) to remove cellular debris. Alternatively, virions can be purified using a gradient, such as a sucrose gradient. Recombinant virus particles can then be pelleted and resuspended in whatever excipient or carrier is desired. Titers can be determined by standard plaque assay or by indirect immunofluorescence using antibodies specific for particular proteins.

In certain aspects, vesiculoviruses that encode or contain one or more protein components (N, P, M, G, and/or L proteins) and a heterologous polynucleotide have been constructed with one or more mutations or variations as compared to a wild-type virus or viral proteins such that the virus has desirable properties for expressing heterologous polynucleotide(s), while having characteristics that are not present in the virus as originally isolated. The methods described herein provide various examples of protocols for implementing methods and compositions of the invention. They provide background for generating mutated or variant viruses through the use of recombinant DNA or nucleic acid technology.

B. Isfahan Virus (ISFV) Constructs

Isfahan virus (ISFV) is a member of the *Vesiculovirus* genus in the Rhabdoviridae family. ISFV was first isolated from sand flies in Iran in 1975 (Tesh et al. *The American journal of tropical medicine and hygiene.* 1977; 26(2):299-306). ISFV appears to be geographically restricted to Iran and some neighboring countries, where there is serological evidence for human infection (Tesh et al., *The American journal of tropical medicine and hygiene.* 1977, 26(2):299-306; Gaidamovich et al., *Voprosy Virusologii.* 1978, (5):556-60). Infection with ISFV has not been linked to human disease and, unlike the prototypical *Vesiculovirus*, vesicular stomatitis virus (VSV), ISFV does not appear to cycle in livestock and/or to cause vesicular lesions in experimentally inoculated animals (Wilks and House, *J Hyg (Lond).* 1986, 97(2):359-68). ISFV is morphologically similar to VSV (Tesh et al. *The American journal of tropical medicine and hygiene.* 1977; 26(2):299-306) and has a similar genomic organization, including highly conserved replication and transcription regulatory sequences (Marriott, *Arch Virol.* 2005, 150(4):671-80). However, both viruses are serologically distinct (Tesh et al. *The American journal of tropical medicine and hygiene.* 1977; 26(2):299-306) and a phylogenetic analysis of vesiculoviruses shows substantial evolutionary divergence (FIG. 1), based upon an amino acid alignment of virus proteins.

Isfahan virus comprises an approximately 11 kb non-segmented, negative-strand RNA genome that encodes five major viral proteins abbreviated N, P, M, G, and L. The nucleotide sequence of the complement (5' to 3') to the Isfahan viral genome is provided in SEQ ID NO:1. The 3' to 5' genomic order in the negative sense RNA genome encodes proteins designated as nucleocapsid (N), phosphoprotein (P), matrix protein (M), transmembrane glycoprotein (G) and polymerase (L), i.e., 3'-N-P-M-G-L-5'. The nucleocapsid is involved in genome encapsidation. An amino acid sequence of an example of the Isfahan virus N protein is provided as SEQ ID NO:2. The P protein is a phosphoprotein involved in RNA synthesis. The amino acid sequence of an example of the Isfahan virus P protein is provided as SEQ ID NO:3. The M protein is a matrix protein. The amino acid sequence of an example of the Isfahan virus M protein is provided as SEQ ID NO:4. The G protein is a glycoprotein. The amino acid sequence of an example of the Isfahan virus G protein is provided as SEQ ID NO:5. The L protein is a large polymerase involved in RNA synthesis. The amino acid sequence of an example of the Isfahan virus L protein is provided as SEQ ID NO:6.

The divergence of ISFV from VSV can be used to aid therapeutic and prophylactic regimens by (1) using rISFV as a vector in place of rVSV, and thus avoiding potential anti-vector immunity with repeated administration of VSV vector; and (2) providing a second *Vesiculovirus* vector so as to constitute a heterologous prime-boost regimen with rVSV.

C. Vesicular Stomatitis Virus (VSV) Constructs

Vesicular stomatitis virus (VSV) comprises an approximately 11 kb non-segmented, negative-strand RNA genome that encodes five major viral proteins abbreviated N, P, M, G, and L. The nucleotide sequences encoding VSV G, M, N, P, and L proteins are known in the art (Rose and Gallione, 1981, *J. Virol.* 39, 519-28; Gallione et al., 1981 *J. Virol.* 39:529-35). A number of VSV serotypes are known and have been sequenced. The genomic sequence of VSV (Indiana) is provided under Accession No. NC001560 in the NCBI database (see SEQ ID NO:7-12), which is incorporated herein as of the priority date of this application. Other sequences for VSV, including VSV (Chandipura) sequences, are available in that database; for example, see Accession Nos. Ay382603, Af128868, V01208, V01207, V01206, M16608, M14715, M14720 and J04350, all of which are incorporated herein as of the priority date of this application. VSV serotypes, such as New Jersey, are also available from depositories such as the American Type Culture Collection, Rockville, Md. (see, e.g., Accession Nos. VR-1238 and VR-1239, which are incorporated herein as of the priority date of this application). Other known VSV sequences and serotypes are described in the art or referenced in the documents cited throughout this specification, see, e.g., International Patent Application No. WO2004/093906 and U.S. Pat. No. 8,287,878, which are incorporated herein as of the priority date of this application.

II. Immunogenic Compositions

Certain embodiments are directed to recombinant vesiculovirus compositions and methods for inducing an antigen-specific immune response to an antigen when administered to a mammalian subject. An immunogenic composition useful in this invention is a replication-competent, attenuated, recombinant Isfahan virus (rISFV) or a vector encoding the same. In certain embodiments, the immunogenic composition contains a recombinant vesiculovirus described herein. Certain aspects are directed to rISFV as described herein. In a further aspect a rISFV comprises a heterologous polynucleotide encoding one or more antigens.

A. Antigens

In certain embodiments a vesiculovirus (e.g., rISFV alone, or in a prime/boost regimen with rVSV) encodes a heterologous antigen. As used herein, the term "antigen" or "targeted antigen" refers to any substance, including complex antigens (e.g. tumor cells, virus infected cells, etc.) that is capable of being the target of an immune response. An antigen may be the target of, for example, a cell-mediated and/or humoral immune response of a subject administered or provided an immunogenic composition described herein. The term "antigen" or "targeted antigen" encompasses for example all or part of viral antigens, bacterial antigens, tumor-specific or tumor-related antigens, parasitic antigens, allergens, and the like. An antigen is capable of being bound by an antibody or T-cell receptor. An antigen is additionally capable of inducing a humoral and/or cellular immune response leading to the production of B- and/or T-lymphocytes. The structural aspect of an antigen, e.g., three-dimensional conformation or modification (e.g., phosphorylation), giving rise to a biological response is referred to herein as an "antigenic determinant" or "epitope." The antigenic determinants or epitopes are those parts of an antigen that are recognized by antibodies, or in the context of an MHC, by T-cell receptors.

Viral antigens include for example antigens from rhabdoviruses (e.g., Lyssavirus including rabies virus), alphaviruses, hepatitis viruses A, B, C, D and E, HIV, herpes viruses, cytomegalovirus, varicella zoster, papilloma viruses, Epstein Barr virus, parainfluenza viruses, adenoviruses, Coxsakie viruses, picornaviruses, rotaviruses, pox viruses, rhinoviruses, rubella virus, papovavirus, mumps virus, measles virus; some non-limiting examples of known viral antigens include the following: antigens derived from alphaviruses such as nsP1-nsP4, capsid, E3, E2, 6K, and E1 proteins; HIV-1 such as tat, nef, gp120 or gp160, gp40, p24, gag, env, vif, vpr, vpu, rev or part and/or combinations thereof; antigens derived from human herpes viruses such as HSV-2 with antigens such as gH, gL, gM, gB, gC, gK, gE or gD, Immediate Early proteins such as ICP27, ICP47, ICP4, ICP36 and ICP0, VP16, US6, USB, UL7, UL19, UL21, UL25, UL46, UL47, UL48, UL49 and UL50, or part and/or combinations thereof; antigens derived from cytomegalovirus, especially human cytomegalovirus such as gB or derivatives thereof; antigens derived from Epstein Barr virus such as gp350 or derivatives thereof; antigens derived from Varicella Zoster Virus such as gp1, 11, 111 and IE63; antigens derived from a hepatitis virus such as hepatitis B, hepatitis C or hepatitis E virus antigen (e.g. env proteins E1 or E2, core protein, NS2, NS3, NS4a, NS4b, NS5a, NS5b, p7, or part and/or combinations thereof of HCV); antigens derived from human papilloma viruses (for example, proteins, e.g., L1, L2, E1, E2, E3, E4, E5, E6, E7, or part and/or combinations thereof); antigens derived from other viral pathogens, such as Respiratory Syncytial virus (e.g. F and G proteins or derivatives thereof), flaviviruses (e.g. Yellow Fever Virus, Dengue Virus, Tick-borne encephalitis virus, Japanese Encephalitis Virus) or Influenza viruses (e.g. HA, NP, NA, or M proteins, or part and/or combinations thereof).

Tumor-specific, tumor-related, or cancer antigens include but are not limited to, carcinoma, lymphoma, blastoma, sarcoma, and leukemia. Expression of such antigens by rISFV provides both the induction of a cell-mediated immune response against the cancer cell and direct cancer cell lysis by rISFV. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer, renal cancer, malignant melanoma, laryngeal cancer, prostate cancer. Cancer antigens are antigens that can potentially stimulate tumor-specific immune responses. Some of these antigens are encoded, although not necessarily expressed, by normal cells. These antigens can be characterized as those that are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens are encoded by viral genes, such as those carried on RNA and DNA tumor viruses. Some non-limiting examples of tumor-specific or tumor-related antigens include MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MACE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUG family (e.g. MUC-1), HER2/neu, p21ras, RCAS1, alpha-fetoprotein, E-cadherin, alpha-catenin, beta-catenin and gamma-catenin, p120ctn, gp100Pme1117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2.

In another embodiment, an attenuated rISFV is utilized per se, that is without the inclusion of a heterologous polynucleotide sequence, as an anti-cancer (oncolytic) therapeutic. ISFV possesses tumor cell killing properties in vitro and in vivo. The term "oncolytic" typically refers to an agent that is capable of killing, lysing, or halting the growth of a cancer cell. In terms of an oncolytic virus the term refers to a virus that can replicate to some degree in a cancer cell, cause the death, lysis, or cessation of cancer cell growth and typically have minimal toxic effects on non-cancer cells. The rISFV is attenuated using any of the methods described herein.

Bacterial antigens include for example antigens from Mycobacteria causing TB and leprosy, pneumococci, aerobic gram-negative bacilli, *mycoplasma, staphylococcus, streptococcus*, salmonellae, chlamydiae, or neisseriae.

Other antigens include for example antigens from parasites such as malaria, leishmaniasis, trypanosomiasis, toxoplasmosis, schistosomiasis, filariasis, as well as antigens that are allergens.

In another aspect the ISFV G gene may be replaced in its entirety by one or more of the heterologous polynucleotide sequences described above. In still another aspect the ISFV G gene may be replaced by a heterologous G gene of a second vesiculovirus, i.e., pseudotyped. In certain aspects a rISFV can be pseudotyped with a G gene from VSV. The VSV G gene can be selected from among the VSV serotypes listed above.

According to variants of the invention, the immunogenic composition comprises at least two targeted antigens, or a heterologous nucleotide sequence encoding at least two targeted antigens, or at least two heterologous nucleotide sequences encoding at least two targeted antigens, or any combination thereof.

In certain embodiments the heterologous antigen is an alphavirus antigen. Most alphaviruses infect terrestrial vertebrates via mosquito-borne transmission and exhibit a broad host range (Strauss et al., 1994 *Microbiol Rev.* 58(3): 491-562). Occasionally, these cycles spill over into humans and domesticated animals to cause disease. Human infections with Old World viruses such as Ross River virus, chikungunya virus, and SINV are typically characterized by fever, rash, and polyarthritis, whereas infections with the New World viruses Venezuelan Equine Encephalitis virus (VEEV), Eastern Equine Encephalitis virus (EEEV), and Western Equine Encephalitis virus (WEEV) can cause fatal encephalitis (Strauss et al., 1994 *Microbiol Rev.* 58(3):491-562). As a consequence the latter viruses were developed as biological weapons during the cold war, and recent aerosol infections of primates confirm their highly debilitating and/or lethal properties (Reed et al., 2007 *The Journal of Infectious Diseases* 196:441-450; Reed et al., 2005 *The Journal of Infectious Diseases* 192:1173-1182; Reed et al., 2004 *The Journal of Infectious Diseases* 189:1013-1017; Smith et al., 2009 Alphaviruses, p. 1241-1274. In D. D. Richman, R. J. Whitley, and F. G. Hayden (ed.), Clinical Virology. ASM Press, Washington, D.C.). EEEV is uniformly lethal for cynomolgus macaques after high dose aerosol infection and causes one of the highest natural human case-fatality rates (>50%) of any viral infection (Reed et al., 2007 *The Journal of Infectious Diseases* 196:441-450). VEEV infection of humans is not typically fatal, but this virus is one of the most infectious viruses by aerosol and is highly debilitating as well as immunosuppressive (Reed et al., 2004 *The Journal of Infectious Diseases* 189:1013-1017; Smith et al., 2009 *Alphaviruses*, p. 1241-1274. In D. D. Richman, R. J. Whitley, and F. G. Hayden (ed.), Clinical Virology. ASM Press, Washington, D.C.; Weaver et al., 2004. *Annu. Rev. Entomol.* 49:141-174). Furthermore, it causes extensive endemic disease throughout Latin America, and its intentional introduction could result in equine amplification and mosquito transmission to infect hundreds of thousands of persons. These traits have resulted in the assignment of the encephalitic alphaviruses to the NIAID category B pathogen list.

Because there are no licensed antiviral treatments or immunogenic compositions for alphaviral diseases, the U.S. population remains vulnerable to a biological attack as well as to natural infections with the 3 encephalitides. Development of an effective antiviral treatment is particularly challenging because diagnoses generally occur only after the prodromal illnesses have progressed to encephalitis about one week after infection. Therefore, immunization is the best approach to protecting against fatal disease.

To address this unmet need, rISFV has been modified to express the E3-E1 glycoproteins of VEEV and EEEV for use as a stand-alone immunogenic composition for both alphaviruses, and/or for use in heterologous prime-boost immunization regimens with rVSV vectors expressing VEEV and EEEV E3-E1 glycoproteins, should such a immunization modality be necessary for optimal efficacy.

B. Formulation of Recombinant *Vesiculoviruses*

The immunogenic compositions useful in this invention, e.g., rISFV alone or in a prime/boost regimen with rVSV compositions, further comprise an immunologically or pharmaceutically acceptable diluent, excipient or carrier, such as sterile water or sterile isotonic saline. The immunogenic compositions may also be mixed with such diluents or carriers in a conventional manner. As used herein the language "pharmaceutically acceptable carrier" is intended to include any and all solvents, dispersion media, coatings, antibacterial and antifungal agents, isotonic and absorption delaying agents, and the like, compatible with administration to humans or other vertebrate hosts. The appropriate carrier is evident to those skilled in the art and will depend in large part upon the route of administration. Thus, the immunogenic compositions useful in this invention may comprise a recombinant replicable ISFV comprising one or more of an N protein gene, a P protein gene, an M protein gene, a G protein gene, and an L protein gene; and further comprising a heterologous polynucleotide sequence, wherein said heterologous polynucleotide sequence (a) is flanked by a transcription start signal and a transcription stop signal, and (b) encodes a heterologous polypeptide; and a pharmaceutically acceptable diluent, excipient or carrier.

Additional components may be present in the immunogenic compositions, including, but not limited to preservatives, surface-active agents, and chemical stabilizers, suspending or dispersing agents. Typically, stabilizers, adjuvants, and preservatives are optimized to determine the best formulation for efficacy in the target human or animal. Suitable exemplary preservatives include chlorobutanol, potassium sorbate, sorbic acid, sulfur dioxide, propyl gallate, the parabens, ethyl vanillin, glycerin, phenol, and parachlorophenol.

Suitable stabilizing ingredients that may be used include, for example, casamino acids, sucrose, gelatin, phenol red, N-Z amine, monopotassium diphosphate, lactose, lactalbumin hydrolysate, and dried milk. Suitable surface-active substances include, without limitation, Freund's incomplete adjuvant, quinone analogs, hexadecylamine, octadecylamine, octadecyl amino acid esters, lysolecithin, dimethyl-dioctadecylammonium bromide, methoxyhexadecylgylcerol, and pluronic polyols; polyamines, e.g., pyran, dextran sulfate, poly IC, carbopol; peptides, e.g., muramyl peptide and dipeptide, dimethylglycine, tuftsin; oil emulsions; and mineral gels, e.g., aluminum phosphate, etc. and immune stimulating complexes (ISCOMS). The rISFVs and rVSVs or any of their polypeptide components may also be incorporated into liposomes for use as an immunogenic composition. The immunogenic compositions may also contain other additives suitable for the selected mode of administration of the composition. The compositions of the invention may also involve lyophilized formulations, which can be used with other pharmaceutically acceptable excipients for developing powder, liquid or suspension dosage forms. See, e.g., Remington: The Science and Practice of Pharmacy, Vol. 2, $19^{th}$ edition (1995), e.g., Chapter 95 Aerosols; and International Patent Publication No. WO99/45966, the teachings of which are hereby incorporated by reference.

These immunogenic compositions can contain additives suitable for administration via any conventional route of administration. In some embodiments, the immunogenic composition of the invention is prepared for administration to human subjects in the form of, for example, liquids, powders, aerosols, tablets, capsules, enteric-coated tablets or capsules, or suppositories. Thus, the immunogenic compositions may also include, but are not limited to, suspensions, solutions, emulsions in oily or aqueous vehicles, pastes, and implantable sustained-release or biodegradable formulations. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Other useful parenterally-administrable formulations include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

The immunogenic compositions described herein are not limited by the selection of the conventional, physiologically acceptable carriers, adjuvants, or other ingredients useful in pharmaceutical preparations of the types described above. The preparation of these pharmaceutically acceptable compositions, from the above-described components, having appropriate pH isotonicity, stability and other conventional characteristics is within the skill of the art.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards required by governments of the countries in which the compositions are being used.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" or "pharmacologically acceptable" refers to molecular entities and compositions that do not produce an allergic or similar untoward reaction when administered to a human. The preparation of an aqueous composition that contains a virus particle as an active ingredient is well understood in the art. Typically, such compositions are prepared as injectables, either as liquid solutions or suspensions; solid forms suitable for solution in, or suspension in, liquid prior to injection can also be prepared.

As described above, any of the embodiments of the recombinant vesiculoviruses may be used in these methods of treatment. Desirably, this composition is admixed with a pharmaceutically acceptable diluent or other components as described above. In one embodiment, the treatment or prevention of an infection caused by a pathogen involves administration of one or more effective amounts of one or a combination of the recombinant vesiculoviruses described herein.

C. Administration of Recombinant *Vesiculovirus*

The antigenic or immunogenic compositions of this invention are administered to a human or to other mammalian subjects by a variety of routes including, but not limited to, intramuscular, intratumoral, intraperitoneal, subcutaneous, intravenous, intraarterial, intranasal, oral, sublingual, buccal, vaginal, rectal, parenteral, intradermal, and transdermal (see, e.g., International patent publication No. WO 98/20734, which is hereby incorporated by reference). The appropriate route is selected depending on the nature of the immunogenic composition used, and an evaluation of the age, weight, sex and general health of the patient and the antigens present in the immunogenic composition, and similar factors by an attending physician.

In the examples provided below, both the immunogenic rISFV compositions and rVSV compositions are administered intramuscularly (i.m.) either individually or in combination in a prime/boost regimen. In other embodiments, it is desirable to administer the rISFV compositions and rVSV compositions by different routes. For example, the rISFV composition may be administered by conventional means, including intramuscular and intranasal administration. However, the selection of dosages and routes of administration are not limitations upon this invention.

The order of immunogenic composition administration and the time periods between individual administrations may be selected by the attending physician or one of skill in the art based upon the physical characteristics and precise responses of the host to the application of the method. Such optimization is expected to be well within the skill of the art.

In general, selection of the appropriate "effective amount" or dosage for the components of the immunogenic composition(s) of the present invention will also be based upon whether the administration is rISFV only or prime/boost with an rVSV composition, as well as the physical condition of the subject, most especially including the general health, age and weight of the immunized subject. The method and routes of administration and the presence of additional components in the immunogenic compositions may also affect the dosages and amounts of the rISFV and rVSV compositions. Such selection and upward or downward adjustment of the effective dose is within the skill of the art. The amount of rISFV and rVSV required to induce an immune response, such as a protective response, or produce a therapeutic effect in the patient without significant adverse side effects varies depending upon these factors.

A suitable dose is formulated in a pharmaceutical composition, as described above (e.g., dissolved in about 0.1 ml to about 2 ml of a physiologically compatible carrier) and delivered by any suitable means. The treatments may include various "unit doses." Unit dose is defined as containing a predetermined quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) or viral particles for viral constructs. Unit doses range from $10^3$, $10^4$, $10^5$, $10^6$, $10^7$, $10^8$, $10^9$, $10^{10}$, $10^{11}$, $10^{12}$, $10^{13}$ pfu or infectious viral particles (vp) and higher. Alternatively, depending on the virus and the titer attainable, one will deliver 1 to 100, 10 to 50, 100-1000, or up to about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$ or higher vp to the patient or to the patient's cells. A suitable dose is formulated in a pharmaceutical composition as described (for example, dissolved in about 0.1 ml to about 2 ml of a physiologically compatible carrier) and delivered by any suitable means.

In one embodiment, the single or boosting dosages for rISFV are the same. Such dosages are generally between $1\times10^7$ pfu (or measured as viral particles) and $1\times10^9$ pfu/viral particles/ml. However, any suitable dose is readily determined by persons skilled in the art.

In the second embodiment of the methods described herein, the administration of a recombinant vesiculovirus (e.g., rISFV) is preceded by administering to a mammalian subject an effective amount of a priming composition comprising a second recombinant vesiculovirus (e.g., rVSV) comprising one or more open reading frames encoding the same or heterologous antigens as those encoded by the first virus. Alternatively, the administration of the first virus is followed by the administration of the second virus. In either regimen, more than one dose of the first virus and/or the second virus may be administered.

According to the present invention, for example, the rVSV immunogenic composition may be administered as a boosting composition subsequent to the administration of the priming rISFV immunogenic composition that presents the selected heterologous antigen or antigens to the host. The mammalian subject is administered an effective amount of a priming composition comprising a rISFV comprising one or more open reading frames encoding one or more heterologous proteins under the control of regulatory sequences directing expression thereof and a pharmaceutically acceptable diluent prior to the immunogenic rVSV composition.

When used as a priming composition, this rISFV composition is administered once or more than once prior to the boosting rVSV composition.

In another embodiment of the prime/boost method, the priming rISFV composition is administered at least once prior to the immunogenic rVSV composition, or administered both prior to and after the rVSV immunogenic composition.

In still further embodiments of the prime/boost regimen, multiple rVSV compositions are administered as later boosters. In one embodiment at least two rVSV compositions are administered following the priming compositions.

Each subsequent vesiculovirus composition may have a different serotype selected from known serotypes and from among any synthetic serotypes provided by manipulation of the vesiculovirus G protein. For example, one rVSV may be the Indiana serotype and the other may be the Chandipura serotype or the New Jersey serotype. In another embodiment, additional rVSV boosters are of the same serotype. When used as a boosting composition, the rVSV compositions are administered serially, after the priming rISFV immunogenic compositions. rISFVs and rVSVs displaying a desired balance of attenuation and immunogenicity are useful in this invention.

In still another embodiment, administration of one or more of the rISFV immunogenic compositions is followed by one or more administrations of the rVSV immunogenic compositions, and then followed by one or more additional administrations of the rISFV immunogenic compositions.

In yet another embodiment, administration of one or more of the rISFV immunogenic compositions is preceded or followed by administration of one or more plasmid DNA immunogenic compositions, wherein the plasmid DNA(s) encode the same or different heterologous polypeptides as the rISFV immunogenic compositions.

III. Proteinaceous Compositions

Proteinaceous compositions of the invention include viral particles and compositions including the viral particles. In certain embodiments, vesiculoviruses will be engineered to include polypeptide variants of viral proteins N, P, M, G, and/or L; and/or heterologous polynucleotides. As used herein, a "protein" or "polypeptide" refers to a polymer of amino acid residues. In some embodiments, a wild-type version of a protein or polypeptide are employed, however, in many embodiments, all or part of a viral protein or polypeptide is absent or altered so as to render the virus more useful for therapy.

A "modified protein" or "modified polypeptide" or "variant protein" or "variant polypeptide" refers to a protein or polypeptide whose chemical structure or amino acid sequence is altered with respect to the wild-type or a reference protein or polypeptide. In some embodiments, a modified protein or polypeptide has at least one modified activity or function (recognizing that proteins or polypeptides may have multiple activities or functions). The modified activity or function may be reduced, diminished, eliminated, enhanced, improved, or altered in some other way with respect to that activity or function in a wild-type protein or polypeptide, or the characteristics of virus containing such a polypeptide. It is contemplated that a modified protein or polypeptide may be altered with respect to one activity or function yet retain wild-type or unaltered activity or function in other respects. Alternatively, a modified protein may be completely nonfunctional or its cognate nucleic acid sequence may have been altered so that the polypeptide is no longer expressed at all, is truncated, or expresses a different amino acid sequence as a result of a frame-shift or other modification.

It is contemplated that polypeptides may be modified by truncation, rendering them shorter than their corresponding unaltered form or by fusion or domain shuffling which may render the altered protein longer.

Amino acid sequence variants of the polypeptides of the present invention can be substitutional, insertional, or deletion variants. A mutation in a gene encoding a polypeptide may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500 or more non-contiguous or contiguous amino acids (i.e., segment) of a polypeptide, as compared to a wild-type or unaltered polypeptide or other reference polypeptide. Various polypeptides encoded by vesiculoviruses may be identified by reference to sequence listing filed with this application or GenBank Accession Numbers and related public database entries provided herein.

Deletion variants lack one or more residues of the native, unaltered, or wild-type protein. Individual residues can be deleted, or all or part of a domain (such as a catalytic or binding domain) can be deleted. The cytoplasmic tail of the vesiculovirus G protein may be truncated so as to attenuate the virus. For example, the rISFV G protein may have a carboxy-terminal truncation of 20 to 25 amino acids, while the rVSV G protein may have a carboxy-terminal truncation of 20 to 28 amino acids. Further attenuation may be achieved by also shuffling the N gene away from its native first position in the vesiculovirus genome, or by a non-cytopathic (ncp) M gene mutation at amino acid positions 33 and 51, as described in U.S. Pat. No. 8,287,878. A stop codon may be introduced (by substitution or insertion) into an encoding nucleic acid sequence to generate a truncated protein. Insertional mutants typically involve the addition of material at a non-terminal point in the polypeptide, a specific type of insert is a chimeric polypeptide that include homologous or similar portions of a related protein in place of the related portion of a target protein. This may include the insertion of an immunoreactive epitope or simply one or more residues. Terminal additions, typically called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

The term "functionally equivalent codon" is used herein to refer to codons that encode the same amino acid, such as the six codons for arginine or serine, and also refers to codons that encode biologically equivalent amino acids. Amino acids codons include: Alanine (Ala, A) GCA, GCC, GCG, or GCU; Cysteine (Cys, C) UGC or UGU; Aspartic acid (Asp, D) GAC or GAU; Glutamic acid (Glu, E) GAA or GAG; Phenylalanine (Phe, F) UUC or UUU; Glycine (Gly, G) GGA, GGC, GGG or GGU; Histidine (His, H) CAC or CAU; Isoleucine (Ile, I) AUA, AUC, or AUU; Lysine (Lys, K) AAA or AAG; Leucine (Leu, L) UUA, UUG, CUA, CUC, CUG, or CUU; Methionine (Met, M) AUG; Asparagine (Asn, N) AAC or AAU; Proline (Pro, P) CCA, CCC, CCG, or CCU; Glutamine (Gln, Q) CAA or CAG; Arginine (Arg, R) AGA, AGG, CGA, CGC, CGG, or CGU; Serine (Ser, S) AGC, AGU, UCA, UCC, UCG, or UCU; Threonine (Thr, T) ACA, ACC, ACG, or ACU; Valine (Val, V) GUA, GUC, GUG, or GUU; Tryptophan (Trp, W) UGG; and Tyrosine (Tyr, Y) UAC or UAU.

It also will be understood that amino acid and nucleic acid sequences may include additional residues, such as additional N- or C-terminal amino acids, or 5' or 3' sequences, and yet still be essentially as set forth herein, including having a certain biological activity. The addition of terminal sequences particularly applies to nucleic acid sequences that may, for example, include various non-coding sequences flanking either the 5' or 3' portions of the coding region or may include various internal sequences, i.e., introns, which are known to occur within genes.

The following is a discussion based upon changing of the amino acids of a protein described herein to create an equivalent, or even an improved, molecule. For example, certain amino acids may be substituted for other amino acids in a protein structure without appreciable loss of interactive binding capacity with structures such as, for example, antigen-binding regions of antibodies or binding sites on receptor molecules. Since it is the interactive capacity and nature of a protein that defines that protein's biological functional activity, certain amino acid substitutions can be made in a protein sequence, and in its underlying polynucleotide sequence, and nevertheless produce a protein with like properties. It is thus contemplated by the inventors that various changes may be made in the nucleic acid sequences of vesiculovirus or an encoded heterologous polynucleotide without appreciable loss of biological utility or activity of interest.

In making such changes, the hydropathic index of amino acids may be considered. The importance of the hydropathic amino acid index in conferring a biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0);

lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine *−0.5); cysteine (−1.0); methionine (−1.3); valine (−1.5); leucine (−1.8); isoleucine (−1.8); tyrosine (2.3); phenylalanine (−2.5); tryptophan (−3.4). It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Examples of substitutions that take into consideration the various foregoing characteristics are well known to those of skill in the art and include: arginine and lysine; glutamate and aspartate; serine and threonine; glutamine and asparagine; and valine, leucine and isoleucine. In making such changes, the phylogenetic analysis of functionally related proteins may be considered (see FIG. 11 and the four amino acid changes made in the rISFV N protein, as depicted therein).

IV. Nucleic Acid Molecules

Certain embodiments are directed to compositions and methods that include polynucleotides that are capable of expressing all or part of a heterologous protein or polypeptide. In some embodiments all or parts of a viral genome are mutated or altered to generate a virus, viral polypeptide, heterologous polynucleotide, or heterologous polypeptide with certain properties and/or characteristics. The polynucleotides may encode a peptide or polypeptide containing all or part of a viral or heterologous amino acid sequence, or be engineered so they do not encode a viral polypeptide or encode a viral polypeptide having at least one function or activity added, increased, reduced, or removed.

As used herein, the term an isolated "RNA, DNA, or nucleic acid segment" refers to a RNA, DNA, or nucleic acid molecule that has been isolated from total genomic DNA or other contaminants. In certain embodiments the polynucleotide has been isolated free of other nucleic acids. A "vesiculovirus genome" or a "VSV genome," or a "ISFV genome" refers to a polynucleotide that can be provided to a host cell to yield a viral particle, in the presence or absence of a helper virus or complementing coding regions supplying other factors in trans.

The term "complementary DNA" or "cDNA" refers to DNA prepared using RNA as a template. There may be times when the full or partial genomic sequence is preferred.

Similarly, a polynucleotide encoding a polypeptide refers to a nucleic acid segment including coding sequences and, in certain aspects, regulatory sequences, isolated substantially away from other naturally occurring genes or protein encoding sequences. In this respect, the term "gene" is used for simplicity to refer to a nucleic acid unit encoding a protein, polypeptide, or peptide (including any sequences required for proper transcription, post-translational modification, or localization). As will be understood by those in the art, this functional term includes genomic sequences, cDNA sequences, and smaller engineered nucleic acid segments that express, or may be adapted to express, proteins, polypeptides, domains, peptides, fusion proteins, and mutants.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol.

It is contemplated that the nucleic acid constructs of the present invention may encode full-length polypeptide(s) from any source or encode a truncated or modified version of the polypeptide(s), for example a heterologous peptide fragment. A nucleic acid sequence may encode a full-length polypeptide sequence with additional heterologous coding sequences, for example to allow for purification of the polypeptide, transport, secretion, post-translational modification, or for therapeutic benefits such as targeting or efficacy. A tag or other heterologous polypeptide may be added to a polypeptide-encoding sequence. The term "heterologous" refers to a polypeptide, polynucleotide, or segment thereof that is not the same as the modified polypeptide, polynucleotide, or found associated with or encoded by the naturally occurring virus.

In a non-limiting example, one or more nucleic acid constructs may be prepared that include a contiguous stretch of nucleotides identical to or complementary to a particular viral segment, such as a vesiculovirus N, P, M, G, or L gene.

The nucleic acid segments used in the present invention encompass modified nucleic acids that encode modified polypeptides. Such sequences may arise as a consequence of codon redundancy and functional equivalency. Functionally equivalent proteins or peptides may be created via the application of recombinant DNA technology, in which changes in the protein structure may be engineered, based on considerations of the properties of the amino acids being exchanged. Changes designed by humans may be introduced through the application of site-directed mutagenesis techniques, e.g., to introduce improvements to the antigenicity or lack thereof. A protein can be modified to reduce toxicity effects of the protein in vivo, or to increase the efficacy of any treatment involving the protein or a virus comprising such a protein.

Recombinant vesiculovirus vectors can be manipulated using a variety of techniques including insertional mutations, point mutations, deletions, and gene shuffling.

A recombinant vesiculovirus may be designed to reduce the N mRNA synthesis in cells infected with virus by shuffling the N (nucleocapsid protein) gene to a position in the genome that is further away (distal) from the native 3' transcription promoter. Because VSV is not considered a human pathogen, and pre-existing immunity to VSV is rare in the human population, the development of VSV-derived vectors has been a focus in areas such as immunogenic compositions and gene therapy. For example, studies have established that VSV can serve as an effective vector for immunogenic compositions, expressing influenza virus hemagglutinin (Roberts et al., 1999 *J. Virol*, 73:3723-3732), measles virus H protein (Schlereth et al., 2000 *J. Virol*, 74:4652-57) and HIV-1 env and gag proteins (Rose et al., 2001 *Cell*, 106:539-549).

In certain other embodiments, the invention concerns isolated nucleic acid segments and recombinant vectors that include within their sequence a contiguous nucleic acid sequence from that shown in sequences identified herein (and/or incorporated by reference).

It also will be understood that this invention is not limited to the particular nucleic acid and amino acid sequences of these identified sequences. Recombinant vectors and isolated nucleic acid segments may therefore variously include vesiculovirus-coding regions, coding regions bearing selected alterations or modifications in the basic coding region, or they may encode larger polypeptides that nevertheless include vesiculovirus-coding regions, or may encode biologically functional equivalent proteins or peptides that have variant amino acids sequences.

In various embodiments, the vesiculovirus polynucleotide and/or a heterologous polynucleotide may be altered or mutated. Alterations or mutations may include insertions, deletions, substitutions, rearrangement, inversions, and the like and may result in the modulation, activation, and/or inactivation of certain proteins or molecular mechanisms, as well as altering the function, location, or expression of a gene product. Where employed, mutagenesis of a polynucleotide can be accomplished by a variety of standard, mutagenic procedures (Sambrook et al, 2001). Mutation is the process whereby changes occur in the function or structure of an organism or molecule. Mutation can involve modification of the nucleotide sequence of a single gene, blocks of genes or whole genomes. Changes in single genes may be the consequence of point mutations that involve the removal, addition, or substitution of a single nucleotide base within a DNA sequence, or they may be the consequence of changes involving the insertion or deletion of large numbers of nucleotides.

Insertional mutagenesis is based on the modification of a gene via insertion of a known nucleotide or nucleic acid fragment. Because it involves the insertion of some type of nucleic acid fragment, the mutations generated are generally loss-of-function, rather than gain-of-function mutations. However, there are examples of insertions generating gain-of-function mutations. Insertional mutagenesis may be accomplished using standard molecular biology techniques.

Structure-guided site-specific mutagenesis represents a powerful tool for the dissection and engineering of protein-ligand interactions (Wells, 1996; Braisted et al., 1996). The technique provides for the preparation and testing of sequence variants by introducing one or more nucleotide sequence changes into a selected DNA.

As used herein, "G-CT" refers to a mutated VSV G gene wherein the encoded G protein is truncated or deleted of some of the amino acids in its cytoplasmic domain (carboxy-terminus), also referred to as the "cytoplasmic tail region" of the G protein. G-CT1 is truncated of its last carboxy terminal 28 amino acids, resulting in a protein product that retains only one amino acid from the twenty-nine amino acid wild-type cytoplasmic domain. Other G gene truncations are identified in U.S. Pat. No. 8,287,878, e.g., G-CT9, having the last twenty carboxy-terminal amino acid residues of the cytoplasmic domain deleted, relative to the wild-type. Among known methods for altering the G protein of rVSV are the technologies described in International Publication No. WO99/32648 and Rose, N. F. et al. 2000 *J. Virol.*, 74:10903-10.

The term "expression vector" refers to a vector containing a nucleic acid sequence coding for at least part of a gene product capable of being transcribed. In some cases, RNA molecules are translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements that bind regulatory proteins and molecules, such as RNA polymerase and other transcription factors. The phrases "operatively positioned," "operatively coupled," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A specific initiation signal also may be required for efficient translation of coding sequences. These signals include the ATG initiation codon or adjacent sequences. Heterologous translational control signals, including the ATG initiation codon, may need to be provided. The translational control signal and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonnenberg, 1988). IRES elements from two members of the picornavirus family (polio and encephalomyocarditis) have been described (Pelletier and Sonnenberg, 1988), as well as an IRES from a mammalian message (Macejak and Sarnow, 1991). By virtue of the IRES element, each open reading frame is accessible to ribosomes for efficient translation.

Vectors can include a multiple cloning site (MCS), which is a nucleic acid region that contains multiple restriction enzyme sites any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. A vector can be linearized or fragmented using a restriction enzyme that cuts within the MCS to enable heterologous sequences to be ligated to the vector. "Ligation" refers to the process of forming phosphodiester bonds between two nucleic acid fragments, which may or may not be contiguous with each other.

The vectors or constructs can comprise at least one termination signal. A "termination signal" or "terminator" is comprised of the nucleic acid sequences involved in specific termination of an RNA transcript by an RNA polymerase. Thus, in certain embodiments a termination signal that ends the production of an RNA transcript is contemplated. A terminator may be necessary in vivo to achieve desirable message levels. Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

A polyadenylation signal can be used to effect proper polyadenylation of a transcript. The nature of the polyadenylation signal is not believed to be crucial to the successful practice of the invention. Embodiments include the SV40 polyadenylation signal and/or the bovine growth hormone polyadenylation signal. Polyadenylation may increase the stability of the transcript or may facilitate cytoplasmic transport.

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker. Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

V. Kits Related to Recombinant *Vesiculovirus*

In still another embodiment, the present invention provides a pharmaceutical kit for ready administration of an immunogenic, prophylactic, or therapeutic regimen. This kit is designed for use in a method of inducing a high level of antigen-specific immune response in a mammalian or vertebrate subject. The kit may contain at least one immunogenic composition comprising a rISFV composition as described herein. For example, multiple prepackaged dosages of the rISFV immunogenic composition are provided in the kit for multiple administrations. The kit also contains at least one immunogenic composition comprising a rVSV immunogenic composition as described herein. In one embodiment, multiple prepackaged dosages of the rVSV immunogenic composition are provided in the kit for multiple administrations.

The kit also contains instructions for using the immunogenic compositions in a prime/boost method as described herein. The kits may also include instructions for performing certain assays, various carriers, excipients, diluents, adjuvants and the like above-described, as well as apparatus for administration of the compositions, such as syringes, electroporation devices, spray devices, etc. Other components may include disposable gloves, decontamination instructions, applicator sticks or containers, among other compositions.

VI. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Analysis and Recovery of Isfahan Virus (ISFV)

A system has been developed for recovery of recombinant Isfahan virus (rISFV) from plasmid DNA encoding ISFV genomic cDNA. The safety of wild-type (wt) rISFV and the attenuated variant rISFVN4ΔCT25gag1 was studied in a highly sensitive 4-5-week-old NIH Swiss Webster mouse intracranial neurovirulence model. Unmodified rISFV wt exhibited an $LD_{50}>10^3$ PFU, in contrast to wtVSV$_{IN}$ with an $LD_{50}$ of <10 PFU. rISFVN4ΔCT25gag1 exhibited an $LD_{50}>10^7$, in contrast to rVSV$_{IN}$N2CT1 with an $LD_{50}$ of $10^4$. These results indicate that rISFV is fundamentally less pathogenic than VSV$_{IN}$ and may not require the utilization of multiple attenuation strategies (N-shuffle, truncation of cytoplasmic tail of G-protein) to achieve similar safety and immunogenicity as rVSV$_{IN}$ vectors.

Isfahan phylogenetic analysis. Available sequences of the genus *Vesiculovirus* were downloaded from GenBank. N gene sequences were aligned in SeaView (PBIL (Pôle Bio-Informatique Lyonnais), France) utilizing the MUSCLE algorithm (Gouy et al., 2010, *Molecular Biology and Evolution* 27:221-24; Edgar, 2004. *Nucleic Acids Research* 32:1792-97). The sequences were aligned by deducing amino acid sequences from open reading frames (ORFs) and then returning to nucleotide sequences for subsequent analyses (Gouy et al., 2010, *Molecular Biology and Evolution* 27:221-24; Edgar, 2004. *Nucleic Acids Research* 32:1792-97). Maximum-likelihood (ML) analysis was performed utilizing the PHYLIP package (Felsenstein, 1989, *Cladistics* 5, 164-1663). The robustness of ML phylogeny was evaluated by bootstrap re-sampling of 100 replicates. The analysis revealed two main clusters within the genus (FIG. 1). The first cluster consists of VSV$_{IN}$ and its subtypes, and VSV$_{NJ}$, whereas the second cluster is comprised of ISFV, Chandipura, and Piry viruses. These data are in congruence with previous serological analyses to determine the relationship of ISFV within the genus, and taken together indicate that ISFV is distantly related to VSV$_{IN}$ (Tesh et al., *Am J Trop Med Hyg.* 1977, March 26(2):299-306).

Generation of Isfahan cDNA clone. A low tissue culture passaged ISFV isolate was obtained from the World Reference Center for Emerging Viruses and Arboviruses at the University of Texas Medical Branch. Viral genomic RNA was isolated from culture supernatants and cDNA fragments spanning the complete ISFV genome were generated by reverse transcription (RT) and PCR amplification (RT-PCR) (FIG. 2). RT-PCR products (fragments 3-5) were cloned step-wise into a plasmid containing the full-length genomic cDNA of VSV New Jersey (pVSV$_{NJ}$N4CT1 HIVgag1) (FIG. 2). The remaining fragments (1-2) were cloned into the pBlueScript plasmid (Invitrogen).

Support plasmids for rescue, expressing individual ISFV proteins (N, P, M, G and L), were generated by cloning the respective open reading frames (ORF) into the Nco I and Sac I sites of the pVSV$_{IN}$ P plasmid (Witko et al., *J Virol Methods.* 2006 July, 135(1):91-101). Cohesive ends compatible with Nco I were generated via BspH I (N and M genes), Pci I (P gene) and BsmB I (G and L genes). The L gene ORF was assembled by joining two cDNA fragments: fragment #1 (BsmB I to Avr II), and fragment #2 (Avr II to Sac I). All resulting rescue support plasmids were verified by nucleotide sequence analysis.

rISFV and rVSV$_{IN}$ constructs encoding Alphavirus envelope genes. The envelope genes (encompassing E3-E2-6K-E1) of EEEV strain FL93 and VEEV strain ZPC738 were cloned into pPBS-ISFV-38 (whose construction is described below). In addition, VEEV-ZPC E3-E1 genes were cloned into pVSV$_{IN}$ N4CT1 HIVgag5. In each case the alphavirus genes were inserted at the fifth position of the vector genome using restriction sites Xho I and Not I in such a way as to place the inserted genes under control of the rISFV or rVSV transcriptase (FIG. 3A). All vectors were verified by full-length nucleotide sequence analysis and expression of alphavirus proteins was confirmed by Western blot (FIG. 3B).

A 3' to 5' gradient in gene expression has been well documented for the vesiculoviruses (Ball and White, *PNAS.* 1976, 73(2):442-6; Villarreal et al., *Biochemistry.* 1976, 15(8):1663-7) and other negative sense RNA viruses (Conzelmann, *Annual review of genetics.* 1998, 32:123-62). Therefore, maximal expression of a target antigen is achieved by insertion of the transgene in the first position of the genome, immediately adjacent to the single strong 3' transcription promoter. However, high expression levels of some antigens can be toxic to rVSV replication, leading to transgene instability and loss of antigen expression (unpublished). Down regulation of expression of toxic antigens, such as HIV-1 Env proteins, by moving the trans gene(s) further away from the 3' transcription promoter has been successful in maintaining genetic stability of Env expression and all target antigens from a range of different pathogens tested thus far in the rVSV platform. To take into account the possibility that the E2/E1 glycoproteins could be toxic to rVSV and rISFV replication if expressed at very high levels, attenuated rVSV and rISFV vectors were generated which expressed E2/E1 from the fifth position in the genome.

Generation of Full Length Recombinant Isfahan Virus pDNA.

Starting material for constructing full length Isfahan virus (ISFV) consisted of two subcloning plasmids that encoded the following:

UTMB Plasmid #1 (renamed pPBS-ISFV-001): The nucleic acid sequences of T7 promoter, VSV Leader, ISFV Leader, N, M, P, G and a partial sequence of L inserted into pBlueScript II SK+ via the XhoI/KpnI sites. The sequences were inserted in a 3' to 5'direction.

UTMB Plasmid #2 (renamed pPBS-ISFV-002): Nucleic acid sequence of partial 3' sequence of ISFV L and terminator inserted into VSV$_{NJ}$ N4CT1 backbone via XhoI/RsrII sites.

In addition to the above, support plasmids encoding individual ISFV genes (M, P, N, G, and L) under the control of a T7 promoter were provided.

Construction of pPBS-ISFV-008 Containing Full-Length ISFV Genomic cDNA

Insertion of ISFV L Deleted Sequence. The missing 2.4 kb nucleic acid sequence of ISFV L was inserted into pPBS-ISFV-001 and pPBS-ISFV-002. The missing fragment was generated by PCR using primers ISF_59-GTGCGTG-GAAGACCGGTACCTCCCATTTGG (SEQ ID NO:13)/ISF_60-TAATGTTATTGCCGGCGAATTCGAAACT-GAATAAATC (SEQ ID NO:14) with pT7-IRES-ISFV L support plasmid as the template. The PCR cycle used was: 95° C., 2 min; (95° C., 30 sec denaturation/50° C., 30 sec annealing/72° C., 2.5 min elongation) at 40 cycles; 72° C., 2 min. To ensure the highest fidelity of the sequence, Pfx50 DNA polymerase (Invitrogen) was used. Next, the PCR product was digested with restriction enzymes KpnI and NgoMIV alongside pPBS-ISFV-001. This restriction digest product was ligated to generate pPBS-ISFV-003. The 2.4 kb was also generated by PCR using primers ISF_62-AATAACATTACTCGAGTTCGGTACCTCCCATTTGG (SEQ ID NO:15)/ISF_63-CAACTTTAAATTCGAAACT-GAATAAATCTATC (SEQ ID NO:16) with pT7-IRES-L support plasmid as the template and inserted into pPBS-ISFV-002 via XhoI and BstBI, respectively, to generate pPBS-ISFV-005. Full length ISFV L was restored by combining pPBS-ISFV-001 and pPBS-ISFV-005 via XhoI/KpnI restriction sites to generate pPBS-ISFV-006.

Construction of T7 promoter adjacent to ISFV Leader. In order to generate a suitable construct for ISFV rescue, the T7 promoter (TAATACGACTCACTATAGG (SEQ ID NO:17)) had to be placed immediately upstream of the ISFV leader sequence (ACGGAGAAAAACAAACCAATTCACGC (SEQ ID NO:18)). Therefore, the PCR amplification of the T7 promoter adjacent to the ISFV leader sequence was achieved using primers ISF_65-TTGAGCACCTGGTACA-GGTATGAATTGATGTGACAC (SEQ ID NO:19)/ISF_66-GCGTGAATTGGTTTGTTTTTCTCCGTCCTATAGT-GAGTCGTATTAGCCGGCCTCGAGTAAATTAATT (SEQ ID NO:20) with pPBS-ISFV-001 as the template. The resulting PCR amplification generated a fragment that served as a template for a second round of amplification using primers ISF_65-TTGAGCACCTGGTACAGGTAT-GAATTGATGTGACAC (SEQ ID NO:21)/ISF_67-CGT-ATTAGCCGGCCTCGAGTAAATTAATT (SEQ ID NO:22) to create EcoNI/NgoMIV restriction sites. The PCR product was then inserted into pPBS-ISFV-001 via EcoNI/NgoMIV restriction sites to generate pPBS-ISFV-007.

Construction of a pDNA Containing a Full Length Isfahan Virus cDNA. A pDNA containing full length ISFV genomic cDNA was generated by digesting pPBS-ISFV-006 and pPBS-ISFV-007 with restriction enzymes NgoMIV/SanDI to construct pPBS-ISFV-008 with the nucleic acid sequence 5'-N$_1$-P$_2$-M$_3$-G$_4$-L$_5$-3' and the T7 promoter adjacent to ISFV leader sequence.

rISFV Rescue Procedure

Preparation of pDNA. For each electroporation, the following plasmid DNAs as listed in Table 1 were combined in a microfuge tube under sterile conditions:

TABLE 1

| Plasmids * | Amounts ** |
|---|---|
| pCMV-Neo-T7 | 50 µg |
| pT7-IRES-ISFV-N | 10 µg |
| pT7-IRES-ISFV-P | 4 µg |
| pT7-IRES-ISFV-L | 1 µg |
| pT7-IRES-ISFV-M | 1 µg |
| pT7-IRES-ISFV-G | 2 µg |
| pPBS-ISFV full genome | 12 µg |

* All viral proteins were expressed from wild type nucleotide sequences and transcription was under control of a T7 promoter
** The pDNA amounts are calculated for one electroporation.

The DNA volume was adjusted to 300 µL with sterile, nuclease-free water. Next, 60 µl of 3M sodium acetate and 900 µL 100% ethanol were added and the mixture was stored overnight at −20° C. The DNA was pelleted by centrifugation at 14000 rpm for 30 minutes at 4° C. The supernatant was aspirated and the DNA pellet was air dried and resuspended in 50 µL sterile, nuclease-free water for each electroporation.

Preparation of Vero Cells. The following media as listed in Table 2 were used for the rescue of ISFV:

TABLE 2

| Rescue Medium #1 | Rescue Medium #2 |
|---|---|
| Dulbecco's Modified Eagle Medium (DMEM) | Iscove's Modified Dulbecco's Medium (IMDM) |
| 10% Fetal Bovine Serum (FBS) | 1% DMSO |
| 0.22 mM β-Mercaptoethanol | 0.22 mM β-Mercaptoethanol |
| 1% Nonessential Amino Acid | 1% Nonessential Amino Acid |
| 1% Sodium Pyruvate | 1% Sodium Pyruvate |

Each electroporation requires cells from approximately 1.3 near-confluent T-150 flasks or one confluent flask. The cell monolayers of each T150 flask were washed with Dulbecco's Phosphate Buffered Saline (DPBS) without $Ca^{2+}$ or $Mg^{2+}$. DPBS was aspirated and trypsinized with 5 ml of trypsin-EDTA solution, and then incubated at 37° C. for up to 5 minutes. After dislodging the cells by tapping the flask, 10 mL of Rescue Medium 1 were added to each flask to suspend the cells and 2 flasks each were transferred to a 50 mL conical tube containing 10 mL Rescue Medium 1. The cells were centrifuged at 1200 rpm for 5 minutes at 4° C. The supernatant was aspirated and the cells resuspended with 10 mL of Rescue Medium 2 per 50 mL conical tube, followed by centrifugation at 1200 rpm for 5 minutes at 4° C. The wash was discarded and the cell pellet resuspended in 0.7 mL of Rescue Medium 2. The cell suspension was transferred to a microfuge tube aliquoted with 50 µl of the plasmid DNA solution and gently mixed, followed by transferring the cells/DNA to an electroporation cuvette.

Electroporation. Cells were electroporated in a BTX820 Electroporator as follows:

| Mode: | Low Voltage |
|---|---|
| Voltage: | 140 V |
| Number of Pulses: | 4 |
| Pulse Length: | 70 msec |
| Pulse Interval: | 500 msec |

After electroporation, all samples were left at room temperature for 10 minutes, then 1 mL of Rescue Medium 1 was added to the cuvette with gentle mixing to resuspend electroporated cells. The cell suspension was then transferred from the cuvette to a 15 mL centrifuge tube containing 10 mL of Rescue Medium 1 and centrifuged at 1200 rpm for 5 minutes at 4° C. The medium was aspirated and cells resuspended in 10 mL Rescue Medium 1 and transferred to T-150 flasks containing 20 mL Rescue Medium 1. The flasks were incubated at 37° C. (5% $CO_2$) for 3 hours, followed by heat-shock at 43° C. (5% $CO_2$) for 3-5 hours and then returned to 32° C. for long-term incubation. After overnight incubation supernatant was replaced with 25 ml of fresh Rescue Medium 1. Positive rISFV rescues showed a cytopathic effect (CPE), characterized by regions of rounded up cells, after 5-10 days. Rescue supernatant was collected; flash frozen in an ethanol/dry ice bath and a single virus clone(s) was isolated by plaque picking followed by two rounds of amplification in Vero cells to generate a virus working stock.

ISFV/*Vesiculovirus* Nucleoprotein Amino Acid Alignment

The amino acid sequence of ISFV nucleoprotein was aligned with other vesiculovirus nucleoprotein sequences (Table 3). The percent matches are based on amino acid identities to the ISFV nucleoprotein sequence. Detailed homology in the sequences can be seen in FIG. 4. Regions of amino acid homology are shaded.

TABLE 3

| Nucleoprotein Sequence from | % Match Compared to ISFV |
|---|---|
| VSV Indiana serotype | 51 |
| VSV NJ serotype | 51 |
| Chandipura | 58 |
| Piry | 60 |
| Cocal | 50 |
| Alagoas | 51 |
| Spring viraemia of carp virus | 43 |
| vesiculo_Pike Fry | 45 |

EXAMPLE 2

Construction of Attenuated rISFV Vectors Using Gene Shuffles and Truncations of the Cytoplasmic Tail of ISFV G Construction of rISFV-N4G5-MCS1. Plasmid pPBS-ISFV-008 comprises the nucleic acid sequence 5'-$N_1$-$P_2$-$M_3$-$G_4$-$L_5$-3' [anti-genome of rISFV]. The subscript numbers indicate the genomic position of each ISFV gene, P (encoding the phosphoprotein), M (encoding the matrix protein), G (encoding the attachment protein), N (encoding the nucleocapsid protein) and L (encoding the polymerase protein).

Plasmid pPBS-ISFV-009 comprises the nucleic acid sequence 5'-$MCS_1$-$N_2$-$P_3$-$M_4$-$G_5$-$L_6$-3' (anti-genome of an rISFV with an additional transcriptional cassette in position 1). According to this formula, MCS (multiple cloning site) is an empty transcriptional unit (TU) in the rISFV anti-genome at position 1 immediately upstream of ISFV N. The subscript numbers indicate the anti-genomic position of each ISFV gene, P (encoding the phosphoprotein), M (encoding the matrix protein), G (encoding the attachment protein), N (encoding the nucleocapsid protein) and L (encoding the polymerase protein).

First, the internal NheI site in ISFV L was removed for cloning purposes: A PCR fragment was generated with primers ISF_68-AATCTGGAcgcgtctcGCTAGtCAGGCT-GATTATTTGAGG (SEQ ID NO:23)/ISF_48-TTGAT-ATTTCCCCAACTCTAC (SEQ ID NO:24) and using pPBS-ISFV-008 as a template and was inserted into pPBS-ISFV-008 via AfeI/BsmBI and AfeI/NheI-restriction sites, respectively, to generate pPBS-ISFV-010.

A second PCR fragment containing partial ISFV M-ISFV G-partial ISFV L sequence was generated with primers ISF_73-CGCATGCCGTCTCCTTATGTTGATTG (SEQ ID NO:25)/ISF28-AGCATTCATTATAAGTATGAC (SEQ ID NO:26) and using pPBS-ISFV-008 as a template. This fragment was inserted into a modified pT7Blue cloning vector (Novagen) via SphI/AgeI restriction sites to generate pPBS-ISFV-011.

Starting from pPBS-ISFV-011, two consecutive mutagenesis reactions were performed using primer pairs ISF_71-

GCTTTTCACAGATGAAGCTAGCTGAAAGTAT-GAAAAAAACG (SEQ ID NO:27)/ISF_72-GTTTTTTTCATACTTTCAGCTAGCTTCATCTGTGAA-AAGCTTG (SEQ ID NO:28) and ISF_69-AACAGAGGT-CAAACGCGTGTCAAAATGACTTCAGTTTTATTCATG (SEQ ID NO:29)/ISF_70-GAATAAAACTGAAGT-CATTTTGACACGCGTTTGACCTCTGTTAAT (SEQ ID NO:30) to generate pPBS-ISFV-013. pPBS-ISFV-013 was then digested using BsmBI/AgeI restriction enzymes and the isolated insert was ligated with a corresponding vector fragment derived from pPBS-ISFV-009. The resulting construct pPBS-ISFV-014 comprised therefore the nucleic acid sequence 5'-$MCS_1$-$N_2$-$P_3$-$M_4$-$G_5$-$L_6$-3', but unlike pPBS-ISFV-009 the ISFV G gene is flanked by MluI/NheI restriction sites allowing the easy exchange with ISFV G variants comprising, for example, truncations of the cytoplasmic tail of ISFV G.

In order to shuffle the N-gene into position 4 and therefore to attenuate rISFV as a vector, a PCR fragment was generated with primers ISF_84-CAGCTGGCGGCCGCTAG-GAATTCAAATCAACATATATGAAAAAAATCAACA-GAGATACAACAATG (SEQ ID NO:31)/ISF20-ACATAGTGGCATTGTGAACAG (SEQ ID NO:32) and using pPBS-ISFV-008 as a template and was inserted into a modified pT7Blue cloning vector (Novagen) via HindIII/NotI restriction sites to generate pPBS-ISFV-017. pPBS-ISFV-017 and pPBS-ISFV-014 were combined by swapping the BsmBI/NotI-insert from pPBS-ISFV-017 into the corresponding vector fragment of pPBS-ISFV-014 to generate pPBS-ISFV-019.

At the same time, pPBS-ISFV-015 was generated by PCR amplification of a fragment with primers ISF_73-CGCAT-GCCGTCTCCTTATGTTGATTG (SEQ ID NO:33)/ISF_82-AGTCATACCGGTCTCGT-TAATTTTTTTCATATCTTTCTTCTGCATGTTATAATTC (SEQ ID NO:34) and using pPBS-ISFV-008 as a template and inserting it into a modified pT7Blue cloning vector (Novagen) via SphI/AgeI-restriction sites. A second PCR fragment was generated with ISF_80-TCGA-GAACGCGTTTGACCTCTGTTAATTTTTTTCATATAT-GTTGATTTGAATTC (SEQ ID NO:35)/ISF_81-ATTC-CAACGCGTCTCGTTAACAGGGATCAAAATGACT-TCTGTAGTAAAG (SEQ ID NO:36) and using pPBS-ISFV-008 as a template and inserted into pPBS-ISFV-015 via BsmBI/MluI and BsaI/MluI-restriction sites, respectively, to generate pPBS-ISFV-016.

Finally, pPBS-ISFV-016 and pPBS-ISFV-019 were combined by swapping the BsmBI/MluI-insert from pPBS-ISFV-016 into the corresponding vector fragment of pPBS-ISFV-019. The resulting construct pPBS-ISFV-020 comprises therefore the nucleic acid sequence 5'-$MCS_1$-$P_2$-$M_3$-$N_4$-$G_5$-$L_6$-3', where compared to pPBS-ISFV-014 the N gene has been shuffled to position 4 of the rISFV.

Construction of rISFV-N4G3-MCS5. Starting from pPBS-ISFV-013, a mutagenesis reaction was performed with primers ISF_90-GCTTTTCACAGAT-GAAGCTAGCGCATGCGGCCGCTGAAAGTAT-GAAAAAAACG (SEQ ID NO:37)/ISF_91-GTTTTTTTCATACTTTCAGCGGCCGCATGCGCTAG-CTTCATCTGTGAAAAGCTTG (SEQ ID NO:38) to generate pPBS-ISFV-022. An oligonucleotide linker generated from ISF_92-CTAGCTGAAAGTATGAAAAAAAT-TAACAGAGGTCAAACTCGAGGATATCGGTAC-CGAAGGCGCGCCCAGCTGTGCGGCC (SEQ ID NO:39) and ISF_93-GGCCGCACAGCTGGGCGCGCCT-TCGGTACCGATATCCTCGAGTTTGACCTCTGT-TAATTTTTTTCATACTTTCAG (SEQ ID NO:40) was then ligated with the NheI/NotI-vector fragment of pPBS-ISFV-022 to generate pPBS-ISFV-023. A PCR fragment was generated with primers ISF_98-GAATTCCTCGAGTT-GACCTCTGTTAATTTTTTTCATATATGTTGATTT-GAATTC (SEQ ID NO:41) and ISF_99-GAT-GAAGCTAGCTGAAAGTATGAAAAAAATTAACAG-GGATCAAAATGACTTCTGTAG (SEQ ID NO:42) and using pPBS-ISFV-016 as a template and inserted into pPBS-ISFV-023 via XhoI/NheI restriction sites to generate pPBS-ISFV-024.

In addition, a PCR fragment was generated with primers ISF16-ATCATTCCTTTATTTGTCAGC (SEQ ID NO:43) and ISF_100-TATATGGCTAGCGAAGACAGAGGGAT-CAAAATGTCTCGACTCAACCAAAT (SEQ ID NO:44) and using pPBS-ISFV-017 as a template and inserted into pPBS-ISFV-017 via BsmBI/NheI restriction sites to generate pPBS-ISFV-025.

Two oligonucleotide linkers generated from ISF_101-CTAGCCCGGCTAATACGACTCACTATAGGACGGA-GAAAAACAAA (SEQ ID NO:45)/ISF_102-TTGGTTT-GTTTTTCTCCGTCCTATAGTGAGTCGTATTAGCCG-GCG (SEQ ID NO:46) and ISF_103-CCAATTCACG-CATTAGAAGATTCCAGAGGAAAGTGCTAAC (SEQ ID NO:47)/ISF_104-CCCTGTTAGCACTTTCCTCTG-GAATCTTCTAATGCGTGAA (SEQ ID NO:48), respectively, were then ligated with the NheI/BbsI-vector fragment of pPBS-ISFV-025 (to generate pPBS-ISFV-026). To generate pPBS-ISFV-030, a plasmid comprising the nucleic acid sequence 5'-$P_1$-$M_2$-$N_3$-$G_4$-$L_5$-3', pPBS-ISFV-026 was digested using BsmBI/NgoMIV restriction enzymes and the isolated insert was ligated with a corresponding vector fragment derived from pPBS-ISFV-020.

Finally, pPBS-ISFV-024 and pPBS-ISFV-030 were combined by swapping the BsmBI/AgeI-insert from pPBS-ISFV-024 into the corresponding vector fragment of pPBS-ISFV-030. The resulting construct pPBS-ISFV-031 comprises therefore the nucleic acid sequence 5'-$P_1$-$M_2$-$G_3$-$N_4$-$MCS_5$-$L_6$-3', where compared to pPBS-ISFV-014 the N gene has been shuffled to position 4 of the rISFV.

Construction of rISFV-N*4G5-MCS1. Although an amino acid sequence alignment of rISFV and rVSV N proteins revealed only an overall 52% homology, the alignment demonstrated a very close homology for a strong, known H2d restricted epitope (MPYLIDFGL; see FIG. 11). Further alignments with additional N proteins from other vesiculoviruses were therefore used to ablate or at least to reduce the homology between rISFV and rVSV for this stretch of amino acids. Starting from pPBS-ISFV-016, a mutagenesis reaction was performed with primers ISF_127-GAAAGACAAGAAGTGGACCAGAGCGATTCCTA-CATGCCTTACATGATTGATATGGGGATCTCAAC-CAAATC (SEQ ID NO:49)/ISF_128-GGTTGAGATCCCCATATCAATCATGTAAGGCATG-TAGGAATCGCTCTGGTCCACTTCTTGTCTTTCTTTC (SEQ ID NO:50) to generate pPBS-ISFV-033 containing the following amino acid changes in ISFV N: K271Q, A272S, L279M, F282M (ISFV N*) (see FIG. 11). pPBS-ISFV-033 was digested using SanDI/BsrGI restriction enzymes and the isolated insert was ligated with a corresponding vector fragment derived from pPBS-ISFV-024 to generate pPBS-ISFV-037. Finally, pPBS-ISFV-037 and pPBS-ISFV-031 were combined by swapping the NheI/AgeI-insert from pPBS-ISFV-037 into the corresponding vector fragment of pPBS-ISFV-031. The resulting construct pPBS-ISFV-038 comprises therefore—like pPBS-ISFV-031—the antigenomic nucleic acid sequence 5'-$P_1$-$M_2$-$G_3$-$N_4$-$MCS_5$-$L_6$-3', however, the encoded ISFV N protein carries the four amino acids changes K271Q, A272S, L279M, F282M (ISFV N*).

Attenuated rISFV N vectors expressing model antigen HIV-1 gag SDE. Plasmid pPBS-HIV-055 is a standard cloning vector comprising a truncated HIV-1 gag gene called HIV-1 gag SDE (single dominant epitope). The amino acid sequence of HIV-1 gag SDE is as follows: [1]MVARASV-LGGELDRWEKEEERPGGKKKYKLKE-EEWASRELERFAVNPGLETSEGCRQ[60]I-[192]GGHQA AMQMLKETINEEA[210]A-[333]ILKALGPAATLEEMM-TACQGVGGYPYDVPDYAPGHKARV[363]L (SEQ ID NO:51) The numbers indicate the amino acid positions in the native HIV-1 gag protein. The peptide "AMQMLKETI" (SEQ ID NO:52) was found to be a strong inducer of a T-cell response in BALB/c mice and HIV-1 gag SDE was therefore used a model antigen testing immunogenicity of different vector designs.

First, pPBS-HIV-055 was digested using XhoI/NotI restriction enzymes and the isolated insert was ligated with a corresponding vector fragment derived from pPBS-ISFV-014. The resulting construct pPBS-ISFV-HIV-013 comprises therefore the nucleic acid sequence 5'-(HIV-1 gag SDE)$_1$-N$_2$-P$_3$-M$_4$-G$_5$-L$_6$-3' and was used to create the corresponding rISFV.

Plasmid pPBS-HIV-055 was digested using XhoI/NotI restriction enzymes and the isolated insert was ligated with a corresponding vector fragment derived from pPBS-ISFV-020. The resulting construct pPBS-ISFV-HIV-014 comprises therefore the nucleic acid sequence 5'-(HIV-1 gag SDE)$_1$-P$_2$-M$_3$-N$_4$-G$_5$-L$_6$-3'. Therefore the corresponding rISFV virus comprises a single attenuation marker—an ISFV N shuffle into position 4 of the rISFV.

A PCR fragment was generated with primers ISF_83-TTTTTTGCTAGCTTCACCTGCATAATAGTGGCAAC (SEQ ID NO:53)/ISF_69-AACAGAGGTCAAACGCGT-GTCAAAATGACTTCAGTTTTATTCATG (SEQ ID NO:54) and using pPBS-ISFV-HIV-014 as a template and was inserted into pPBS-ISFV-HIV-014 via MluI/NheI to generate pPBS-ISFV-HIV-015, now comprising the nucleic acid sequence 5'-(HIV-1 gag SDE)$_1$-P$_2$-M$_3$-N$_4$-(GΔCT25)$_5$-L$_6$-3'. Therefore the corresponding rISFV virus comprises two attenuation markers: (1) shuffling of ISFV N into position 4 of the rISFV antigenome and (2) truncating the distal end of the cytoplasmic tail (CT) of ISFV G by 25 amino acids. The precise length of the CT and transmembrane (TM) domains of ISFV G protein have not been as well characterized as those of VSV$_{IN}$, but an approximate 18 amino acid (aa) hydrophobic domain near the carboxyl terminus is predicted as the ISFV G protein TM anchor. The remaining downstream 33 aa residues represent the G protein CT.

In addition, pPBS-ISFV-033 was digested using BsmBI/MluI restriction enzymes and the isolated insert was ligated with a corresponding vector fragment derived from pPBS-ISFV-HIV-015. The resulting construct pPBS-ISFV-HIV-018 comprised therefore the nucleic acid sequence 5'-(HIV-1 gag SDE)$_1$-P$_2$-M$_3$-N*$_4$-(GΔCT25)$_5$-L$_6$-3'. Compared to rISFV-HIV-015, the encoded ISFV N gene in the corresponding rISFV-HIV-003 carried the four amino acids changes K271Q, A272S, L279M, F282M within the known, strong T cell epitope for BALB/c mice.

Plasmid pPBS-ISFV-HIV-015 was digested using MluI/NheI restriction enzymes and the isolated insert was ligated with a corresponding vector fragment derived from pPBS-ISFV-HIV-013. The resulting construct pPBS-ISFV-HIV-017 comprised therefore the nucleic acid sequence 5'-(HIV-1 gag SDE)$_1$-N$_2$-P$_3$-M$_4$-(GΔCT25)$_5$-L$_6$-3'. Therefore the corresponding rISFV virus comprises a single attenuation marker—the truncation of the ISFV G cytoplasmic tail.

Finally, an attenuated rISFV vector was generated in which the truncated ISFV GΔCT25 gene was replaced by VSV$_{NJ}$ GCT1 gene, which encoded a modified VSV G from the NJ serotype with similar truncation at the cytoplasmic tail of 28 amino acids. To generate pPBS-ISFV-HIV-016 [comprising the nucleotide sequence 5'-(HIV-1 gag SDE)$_1$-P$_2$-M$_3$-N$_4$-(VSV$_{NJ}$ GCT1)$_5$-L$_6$-3'], pPBS-VSV-HIV-054 (rVSV cloning vector containing a VSV$_{NJ}$ GCT1 gene flanked by MluI/NheI restriction enzyme sites) was digested using MluI/NheI restriction enzymes. The isolated insert was then ligated with a corresponding vector fragment derived from pPBS-ISFV-HIV-015. The resulting construct pPBS-ISFV-HIV-016 comprised therefore the nucleic acid sequence 5'-(HIV-1 gag SDE)$_1$-N$_2$-P$_3$-M$_4$-(VSV$_{NJ}$ G CT1)$_5$-L$_6$-3' and was used to rescue the corresponding rISFV.

The attenuation of all the rISFVs expressing HIV-1 gag SDE was tested in vitro by plaque assay. The observed plaque sizes were as follows (FIG. 5): rISFV-HIV-013=rISFV-HIV-14>rISFV-HIV-15=rISFV-HIV-017≥rISFV-HIV-018=rISFV-HIV-016.

In addition to the rISFV constructs described above, two attenuated rVSV vectors generated from the following plasmids were used in the prime-boost immunization experiments:

pPBS-VSV-HIV-106 comprises the nucleic acid sequence 5'-(HIV-1 gag SDE)$_1$-P$_2$-M$_3$-N$_4$-(G CT1)$_5$-L$_6$-3' and all vector genes (P, M, N, G CT1 and L) are derived from VSV Indiana serotype. The rVSV$_{IN}$ derived from this plasmid was used in the study depicted in FIG. 16.

pPBS-VSV-HIV-122 comprises the nucleic acid sequence 5'-(HIV-1 gag SDE)$_1$-P$_2$-M$_3$-N$_4$-(G CT1)$_5$-L$_6$-3', vector genes (P, M, N, and L) are derived from VSV Indiana serotype, and vector gene G CT1 is derived from VSV NJ serotype. The rVSV$_{NJ}$ derived from this plasmid was used in the study depicted in FIG. 16.

Stabilizing the truncation of the cytoplasmic tail of ISFV G. Numerous attenuated rISFVs comprising an ISFV GΔCT25 gene (e.g. rISFV-HIV-015 and rISFV-HIV-018) were extensively passaged in Vero cell culture to determine the stability of this attenuation marker. At passage 10 virtually all rISFVs extended the cytoplasmic tail by two amino acids to contain essentially a rISFV GΔCT23 gene. Thereby, the tested rISFVs changed the stop codon of the ISFV GΔCT25 gene into a codon for an amino acid and then used an alternative in frame stop codon two codons further downstream. Two manipulations of ISFV GΔCT25-L gene junction were therefore examined for their ability to stabilize the attenuation marker ISFV GΔCT25 in rISFV:

A) Combining the transcriptional (underscored) and translational (bold) stop signal for the transcriptional cassette containing ISFV GΔCT25:

(SEQ ID NO: 55)

```
...gtgcgtatga aaaaaacgaa tcaacagagt tcatcatgga tgagtactct gaagaaaagt ggggcgattc...
...cacgcatact tttttttgctt agttgtctca agtagtacct actcatgaga cttcttttca ccccgctaag...
>.......>> ISF G deltaCT25
    l   c   v   -
```

-continued (SEQ ID NO: 56)
```
>>..............ISF L................>
   m   d   e   y   s   e   e   k   w   g   d
```

The last amino acid of ISFV GΔCT25 changes from arginine to valine.

B) Using the 3'-NCR of VSV$_{IN}$ G CT1 present in prototypical rVSV$_{IN}$-N4CT1 vectors as 3'-NCR for the ISFV GΔCT25 expressing cassette:

```
           NheI
          -+----
gtgcaggtga gctagccgcc tagccagatt cttcatgttt ggaccaaatc aacttgtgat accatgctca
cacgtccact cgatcggcgg atcgtctaa gaagtacaaa cctggtttag ttgaacacta tggtacgagt
>........>> ISF G CTdelta25
 l  c   r  -
```

(SEQ ID NO: 57)
```
aagaggcctc aattatattt gagttttttaa tttttatgaa aaaaacgaat caacagagtt catcatggat
ttctccggag ttaatataaa ctcaaaaatt aaaaatactt tttttgctta gttgtctcaa gtagtaccta
                                                              ISF L >>...>
                                                                     m   d
```

Results showed that only approach (B) stabilized the ISFV GΔCT25 attenuation marker during extensive passage of corresponding rISFV viruses (e.g. rISF-HIV-020) in Vero cell culture.

Approach A—Construction

In order to manipulate the ISFV GΔCT25-L gene junction, pPBS-ISFV-HIV-018 was digested using MluI/NheI restriction enzymes and inserted into a corresponding vector fragment derived from a modified pT7Blue cloning vector (Novagen) to generate pPBS-ISFV-049.

First, a mutagenesis reaction was performed on pPBS-ISFV-049 with primers ISF_140-CTATTATGCGTATGC-GAGACGCGTCTCGTATGAAAAAAACGAATCAACA-GAG (SEQ ID NO:58)/ISF_141-CTGTTGATTCGTTTTTTTCATACGAGACGCGTCT-CGCATACGCATAATAGTG (SEQ ID NO:59) to generate pPBS-ISFV-051. In addition, a PCR fragment was generated with primers ISF_146-AATTAACGTCTCAGAGATT-GCAGCGAACCCCAGTGCGGGCTGCTGTTTCTTTC (SEQ ID NO:60)/ISF_69-AACAGAGGTCAAACGCGT-GTCAAAATGACTTCAGTTTTATTCATG (SEQ ID NO:61) and using pPBS-ISFV-031 as a template. Together with an oligonucleotide linker generated from ISF_144-TCTCTGTGATCCTGATCATCGGACTGATGAGGCT-GCTGCCACTACTGTGCAGGTGAG (SEQ ID NO:62) and ISF_145-CTAGCTCACCTGCACAGTAGTGGCA-GCAGCCTCATCAGTCCGATGATCAGGATCACA (SEQ ID NO:63) the PCR fragment (MluI/BsmBI) was then inserted into pPBS-ISFV-049 via MluI/NheI to generate pPBS-ISFV-056. Compared to pPBS-ISFV-049, the nucleotide sequence encoding the transmembrane region of ISFV GΔCT25 in pPBS-ISFV-056 has been silently modified to reduce A/T richness. A PCR fragment was generated with primers ISF_147-CTAGGCGCGTCTCGCATACGCACA-GTAGTGGCAG (SEQ ID NO:64)/ISF_69-AACAGAGGT-CAAACGCGTGTCAAAATGACTTCAGTTTTATTCATG (SEQ ID NO:65) and using pPBS-ISFV-056 as a template and inserted into pPBS-ISFV-051 via MluI/BsmBI to generate pPBS-ISFV-059.

Plasmid pPBS-ISFV-059 was digested using MluI/AgeI restriction enzymes and the isolated insert was ligated with a corresponding vector fragment derived from pPBS-ISFV-HIV-018. The resulting construct pPBS-ISFV-HIV-021 comprises therefore the nucleic acid sequence 5'-(HIV-1 gag SDE)$_1$-N*$_2$-P$_3$-M$_4$-G$_5$-L$_6$-3', has silent nucleotide changes in the transmembrane region of ISFV GΔCT25 to reduce A/T richness compared to the native sequence, and the Stop codon of ISFV GΔCT25 is part of the transcriptional stop in the ISFV GΔCT25-L gene junction.

Approach B—Construction

Plasmid pPBS-ISFV-056 was digested using MluI/NheI restriction enzymes and the isolated insert was ligated with a corresponding vector fragment derived from pPBS-VSV-HIV-020, which contains an anti-genomic sequence of an attenuated rVSV vector (N4CT1) expressing HIV-1 gag from the first transcriptional cassette. The resulting construct pPBS-ISFV-057 therefore comprises the nucleic acid sequence 5'-(HIV-1 gag)$_1$-VSV P$_2$-VSV M$_3$-VSV N$_4$-ISFV GΔCT25$_5$-VSV L$_6$-3' and thereby the 3'-NCR of VSV G CT1 is linked to the open reading frame encoding ISFV GΔCT25.

A PCR fragment was generated with primers ISF_148-TGTTAGCGTCTCTCATAAAAATTAAAAACT-CAAATATAATTG (SEQ ID NO:66) and ISF_69-AACA-GAGGTCAAACGCGTGTCAAAATGACTTCAGTTT-TATTCATG (SEQ ID NO:67) and using pPBS-ISFV-057 as a template and inserted into pPBS-ISFV-051 via MluI/BsmBI to generate pPBS-ISFV-058.

Finally, pPBS-ISFV-058 was digested using MluI/AgeI restriction enzymes and the isolated insert was ligated with a corresponding vector fragment derived from pPBS-ISFV-HIV-018. The resulting construct pPBS-ISFV-HIV-021 comprises therefore the nucleic acid sequence 5'-(HIV-1 gag SDE)$_1$-N*$_2$-P$_3$-M$_4$-G$_5$-L$_6$-3', has silent nucleotide changes in the transmembrane region of ISFV GΔCT25 to reduce A/T richness compared to the native sequence, and comprises the 3'-NCR of VSV GCT1 in the ISFV GΔCT25-L gene junction.

EXAMPLE 3

Animal Studies

A series of mouse studies was performed to investigate the relative safety and efficacy of immunogenic compositions comprising rISFV vectors expressing alphavirus proteins. The mouse intra-cranial (IC) LD$_{50}$ model was used for a primary assessment of vector safety due to the known neurovirulence properties of vesiculoviruses and related viruses (Olitsky et al., *Journal of Experimental Medicine*. 1934, 59:159-71; Frank et al., *Am J Vet Res*. 1945, January: 28-38; Sabin et al., *Journal of Experimental Medicine*. 1937, 66:15-34; Rao et al., *Lancet*. 2004, 364(9437):869-74). Efficacy was assessed in stringent VEEV and EEEV challenge models.

Neurovirulence of rISFV vectors. A pilot study was performed to investigate the neurovirulence properties of unmodified rISFV and a highly attenuated variant expressing HIV-1 gag (rISFV-N4 GΔCT25 HIVgag1). An rVSV$_{IN}$ N2CT1 vector with a known LD$_{50}$ from previous studies was utilized as a positive control (Clarke et al., *J Virol.* 2007, February; 81(4):2056-64). Groups of 10 five-week-old, female Swiss Webster mice were inoculated IC with 25 μL of serial 10-fold dilutions of each virus via the intracerebral (IC) route and animals were observed for lethality for 21 days. PBS was used as a control for the injection process (Table 4).

Limited lethality was observed in animals injected with rISFV vectors and consequently an LD$_{50}$ could not be determined (Table 4). In contrast, rVSV$_{IN}$ N2CT1 did cause lethality and an LD$_{50}$ (10$^4$ pfu) similar to that determined in previous studies was determined (Table 4). These data suggest that rISFV is inherently less neurovirulent than rVSV$_{IN}$, which demonstrated an LD$_{50}$ of 5-10 plaque forming units (PFU) in its unmodified form (Clarke et al., *J Virol.* 2007, February; 81(4):2056-64).

Protective Efficacy of rISFV vectors. A series of studies was performed to investigate the potential of rISFV as a vector for protection against alphavirus infection and disease. For these studies, 4-6-week-old female CD-1 mice were immunized by the intramuscular route using a 50 μL dose volume. Mice were then challenged with 10$^4$ PFU of either VEEV-ZPC or EEEV-FL93 injected subcutaneously. All animal care and procedures conformed to Institutional Animal Care and Use Committee guidelines.

Figure 6:
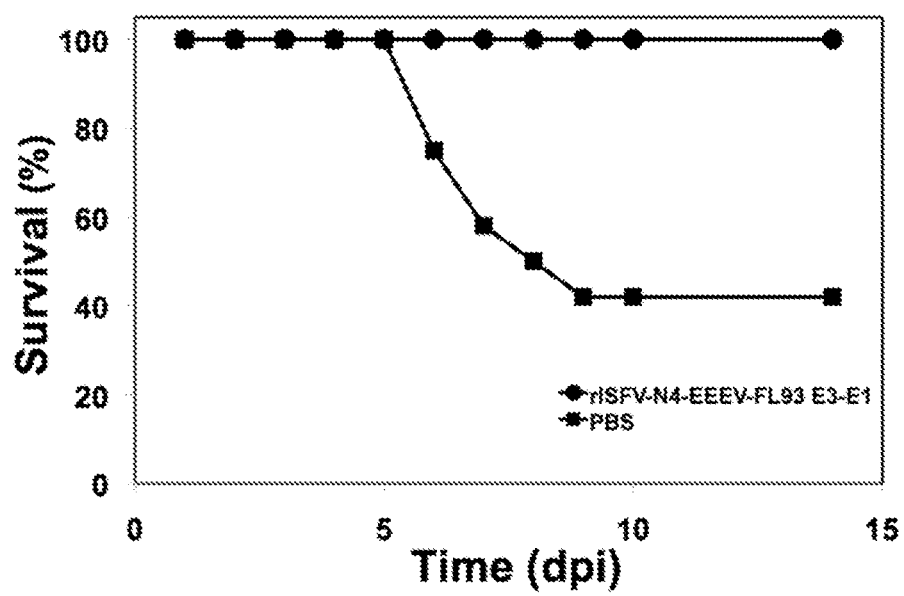
FIG. 6 depicts the percent survival of mice immunized with rISFV-N4 [also designated rISFV-N4-G3-(EEEV FL93 E3-E1)5] expressing eastern equine encephalitis virus (EEEV)-strain FL93 E3-E1 proteins, followed by lethal challenge with EEEV-FL93.

Short term protection against VEEV and EEEV challenge. To determine whether rISFV-N4G3 vectors encoding E3-E1 of VEEV-ZPC or EEEV-FL93 in the fifth position could protect against lethal challenge with VEEV and EEEV, cohorts of CD-1 mice were immunized with 10$^8$ PFU of the vectors and then challenged 3-4 weeks post-immunization (Table 5). Following immunization, a neutralizing antibody response was readily detected in mice immunized with rISFV-N4G3-(EEEV-FL93 E3-E1)5, whereas little neutralizing antibody was detected in animals immunized with rISFV-N4G3-(VEEV-ZPC)5 (Tables 6, 7). Regardless of the antibody response, all animals were protected against lethal EEEV-FL93 and VEEV-ZPC challenge (FIG. 6 and FIG. 7).

TABLE 5

Study design for VEEV-ZPC and EEEV-FL93 challenge studies

| | | Immunization | | | Challenge | | |
|---|---|---|---|---|---|---|---|
| Group | Immunization Construct | Dose (pfu) | Route | Number of Animals | Virus | Dose (pfu) | Route |
| 1 | rISF-N4G3-(VEEV ZPC E3-E1)5 | 10$^8$ | IM | 10 | VEEV ZPC | 10$^4$ | SC |
| 2 | PBS | | IM | 10 | VEEV ZPC | 10$^4$ | SC |
| 3 | rISF-N4G3-(EEEV FL93 E3-E1)5 | 10$^8$ | IM | 10 | EEEV FL93 | 10$^4$ | SC |
| 4 | PBS | | IM | 12 | EEEV FL93 | 10$^4$ | SC |

TABLE 6

Neutralizing antibody response in mice immunized with rISFV-N4G3-(EEEV-FL93 E3-E1)5

| | PRNT$_{80}$ | |
|---|---|---|
| Animal # | Day 14 | Day 21 |
| 1 | 40 | 80 |
| 2 | 0 | 0 |
| 3 | 40 | 20 |
| 4 | 40 | 320 |
| 5 | 40 | 160 |
| 6 | 40 | 80 |
| 7 | 80 | 80 |
| 8 | 0 | 80 |
| 9 | 160 | 40 |
| 10 | 40 | 160 |
| Mean | 48 | 102 |
| SD | 45 | 93 |

TABLE 4

LD$_{50}$ titer of rISFV and rVSV$_{IN}$ vectors in Swiss Webster mice

| Viral Construct | N | Dose (pfu) | Survival (%) | LD$_{50}$ (pfu) |
|---|---|---|---|---|
| rISFV N4ΔCT25 HIVgag1 | 10 | 10$^7$ | 100 | >10$^7$ |
| | 10 | 10$^6$ | 100 | |
| | 10 | 10$^5$ | 100 | |
| | 10 | 10$^4$ | 100 | |
| | 10 | 10$^3$ | 100 | |
| rVSV$_{IN}$ N2CT1 | 10 | 10$^4$ | 50 | 10$^4$ |
| | 10 | 10$^3$ | 90 | |
| | 10 | 10$^2$ | 90 | |
| rISFV | 10 | 10$^3$ | 80 | >10$^3$ |
| | 10 | 10$^2$ | 100 | |
| | 10 | 10$^1$ | 100 | |
| PBS | 10 | | 100 | |

TABLE 7

Neutralizing antibody response in mice immunized with rISFV-N4G3-(VEEV-ZPC E3-E1)5

| | PRNT$_{80}$ | |
|---|---|---|
| Animal # | Day 21 | Day 28 |
| 1 | 0 | 0 |
| 2 | 0 | 0 |
| 3 | 0 | 0 |
| 4 | 0 | 40 |
| 5 | 0 | 0 |
| 6 | 0 | 0 |
| 7 | 0 | 0 |
| 8 | 0 | 0 |
| 9 | 0 | 0 |
| 10 | 0 | 0 |

Dose Titration and Long-term Immunity study. Animals were immunized with either 10$^8$ or 10$^7$ PFU of rISFV-N4G3-(VEEV-ZPC E3-E1)5 or rVSV$_{IN}$ N4G$_{(CT-1)}$3-(VEEV-ZPC E3-E1)5 (Table 8). Following immunization, a VEEV neutralizing antibody response could be detected in most rISFV-N4G3-(VEEV-ZPC E3-E1)5-immunized animals at both doses (Table 9). More robust neutralizing antibody responses were detected in all animals immunized with rVSV$_{IN}$ N4G$_{(CT-1)}$3-(VEEV-ZPC E3-E1)5 (Table 10). However, as observed in the previous study, regardless of neutralizing antibody response to VEEV, all animals were protected following lethal challenge (FIG. 8).

TABLE 8

Dose Titration and Long-term Immunity study design

| | Immunization | | | | Challenge (4 & 30 weeks post-infection) | | |
|---|---|---|---|---|---|---|---|
| Group | Immunization Construct | Dose (pfu) | Route | No. of Animals | Virus | Dose (pfu) | Route | No. of Animals |
| 1 | rISF-N4G3-(VEEV ZPC E3-E1)5 | $10^8$ | IM | 10 | VEEV ZPC | $10^4$ | SC | 5 |
| 2 | rISF-N4G3-(VEEV ZPC E3-E1)5 | $10^7$ | IM | 10 | VEEV ZPC | $10^4$ | SC | 5 |
| 3 | rVSV$_{IN}$N4G$_{(CT-1)}$3-(VEEV-ZPC E3-E1)5 | $10^8$ | IM | 10 | VEEV ZPC | $10^4$ | SC | 5 |
| 4 | rVSV$_{IN}$N4G$_{(CT-1)}$3-(VEEV-ZPC E3-E1)5 | $10^7$ | IM | 10 | VEEV ZPC | $10^4$ | SC | 5 |
| 5 | PBS | | IM | 10 | VEEV ZPC | $10^4$ | SC | 5 |

TABLE 9

Neutralizing antibody response in mice immunized with rISFV-N4G3-(VEEV-ZPC E3-E1)5

| | $10^7$ PFU | | | $10^8$ PFU | |
|---|---|---|---|---|---|
| | PRNT$_{80}$ | | | PRNT$_{80}$ | |
| Animal # | Day 25 | Day 35 | Animal # | Day 25 | Day 35 |
| 1 | 80 | 80 | 1 | 80 | 640 |
| 2 | 80 | 640 | 2 | 80 | 20 |
| 3 | 80 | 0 | 3 | 80 | 0 |
| 4 | 40 | 0 | 4 | 40 | 0 |
| 5 | 40 | 80 | 5 | 20 | 20 |
| 6 | 20 | 20 | 6 | 20 | 20 |
| 7 | 80 | 320 | 7 | 20 | 40 |
| 8 | 40 | 20 | 8 | 20 | 20 |
| 9 | 80 | 320 | 9 | 0 | 0 |
| 10 | 0 | 80 | 10 | 20 | 20 |
| Mean | 54 | 156 | Mean | 38 | 78 |
| SD | 30 | 208 | SD | 30 | 198 |

TABLE 10

Neutralizing antibody response in mice immunized with rVSV$_{IN}$-N4G$_{(CT-1)}$3-(VEEV-ZPC E3-E1)5

| | $10^7$ PFU | | | $10^8$ PFU | |
|---|---|---|---|---|---|
| | PRNT$_{80}$ | | | PRNT$_{80}$ | |
| Animal # | Day 25 | Day 35 | Animal # | Day 25 | Day 35 |
| 1 | 640 | 640 | 1 | 80 | 20 |
| 2 | 640 | 640 | 2 | 40 | 640 |
| 3 | 640 | 320 | 3 | 0 | 20 |
| 4 | 640 | 640 | 4 | 640 | 640 |
| 5 | 640 | 640 | 5 | 640 | 40 |
| 6 | 320 | 160 | 6 | 640 | 640 |
| 7 | 640 | 640 | 7 | 80 | 160 |
| 8 | 640 | 320 | 8 | 640 | 40 |
| Mean | 600 | 500 | Mean | 344 | 288 |
| SD | 113 | 199 | SD | 313 | 306 |

Efficacy of blended immunogenic compositions. Since an immunogenic composition should provide protection from more than one alphavirus, a study was designed to investigate if animals simultaneously immunized with rISFV-N4G3-(VEEV-ZPC E3-E1)5 and rISFV-N4G3-(EEEV-FL93 E3-E1)5 could be protected against lethal challenge against both EEEV-FL93 and VEEV-ZPC (Table 11). As in previous studies, neutralizing antibodies to both EEEV-FL93 and VEEV-ZPC were detected in almost all mice (Tables 12 and 13) and all immunized animals were protected against lethal EEEV-FL93 (FIG. 9) or VEEV-ZPC (FIG. 10) challenge. These results demonstrate that blended immunogenic compositions can provide protection against lethal challenge from multiple alphaviruses.

TABLE 11

Blended Immunization study design

| | Immunization | | | | Challenge VEEV-ZPC | | | Challenge EEEV-FL93 | | |
|---|---|---|---|---|---|---|---|---|---|---|
| Group | Immunization Construct | Dose* (pfu) | Route | Number of Animals | Dose (pfu) | Route | No. of Animals | Dose (pfu) | Route | No. of Animals |
| 1 | rISF-N4G3-(VEEV ZPC E3-E1)5 & rISF-N4G3-(EEEV FL93 E3-E1)5 | $10^8$ | IM | 20 | $10^4$ | SC | 10 | $10^5$ | IP | 10 |
| 2 | PBS | | IM | 20 | $10^4$ | SC | 10 | $10^5$ | IP | 11 |

*Group 1 animals were immunized with $10^8$ pfu of each virus

TABLE 12

Neutralizing antibody response against EEEV-FL93 in mice immunized with rISFV-N4G3-(EEEV-FL93 E3-E1)5 and rISFV-N4G3-(VEEV ZPC E3-E1)5

| Animal # | PRNT$_{80}$ | |
|---|---|---|
| | Day 14 | Day 21 |
| 1 | 80 | 160 |
| 2 | 40 | 80 |
| 3 | 80 | 80 |
| 4 | 80 | 320 |
| 5 | 40 | 80 |
| 6 | 80 | 160 |
| 7 | 80 | 80 |
| 8 | 40 | 80 |
| 9 | 80 | 160 |
| 10 | 40 | 320 |
| Mean | 64 | 152 |
| SD | 21 | 96 |

TABLE 13

Neutralizing antibody response against VEEV-ZPC in mice immunized with rISFV-N4G3-(EEEV-FL93 E3-E1)5 and rISFV-N4G3-(VEEV ZPC E3-E1)5

| Animal # | PRNT$_{80}$ | |
|---|---|---|
| | Day 14 | Day 21 |
| 1 | 0 | 20 |
| 2 | 0 | 20 |
| 3 | 20 | 40 |
| 4 | 40 | 20 |
| 5 | 40 | 20 |
| 6 | 20 | 20 |
| 7 | 80 | 80 |
| 8 | 0 | 0 |
| 9 | 80 | 80 |
| 10 | 0 | 20 |
| Mean | 28 | 32 |
| SD | 32 | 27 |

EXAMPLE 4

Prime/Boost Study PBS-MU-062 with rVSV and rISFV Vectors in Balb/C Mice

A series of mouse studies was performed to assess a prime/boost regimen using rVSV and rISFV encoding an HIV Gag single dominant epitope (SDE) in Balb/c mice. These studies were designed to meet two study objectives: (a) PBS-Mu-062a: to study the immunogenicity of two new rISFV-HIV gag SDE vectors in mice, and to select the preferred candidate for a future prime/boost study with rVSV$_{IN}$ N4CT1Gag, and (b) PBS-Mu-062b: to compare the immune responses elicited using the prime/boost combination of rVSV$_{NJ}$/rVSV$_{IN}$ and rISFV/rVSV$_{IN}$.

PBS-Mu-062a: For this study, the relative immunogenicity of two candidate rISFV-based HIV gag expressing vectors were compared with the goal of advancing the most immunogenic construct into future prime/boost studies with rVSV$_{IN}$ based HIV gag-expressing vectors. A summary of the PBS-Mu-062a study design is provided in FIG. 13. For this study, BALB/c mice (n=5/group) were immunized by intramuscular injection with 10$^7$ pfu of the HIV gag-expressing vectors outlined in FIG. 12 and ten days later, splenocytes were collected and tested for HIV gag SDE and rVSV$_{IN}$ N peptide pool-specific IFN-γ secretion by ELISpot analysis (FIG. 14). In this study, immunization with rISFV-HIV-016 (rISFV) resulted in a mean HIV gag SDE-specific interferon-γ ELISpot response of 236±74 SFC/10$^6$ splenocytes, a response which was not significantly different than the HIV gag SDE-specific ELISpot response (147±32 SFC/10$^6$ splenocytes) elicited by the other rISFV-HIV gag candidate rISFV-HIV-018 (rISFVN*)(FIG. 14, left). Importantly, the vector rISFV-HIV-018, which encodes a viral N protein with a series of mutations in a known H2d-restricted epitope, showed a reduced tendency to elicit anti-vector rVSV$_{IN}$ N peptide-pool specific ELISpot responses (45±15 SFC/10$^6$ splenocytes) compared to the rISFV-HIV gag candidate rISFV-HIV-016 (140±59 SFC/10$^6$ splenocytes) which encodes a wild-type viral N gene (FIG. 14, right). Based on these results, rISFVN* (rISFV-HIV-018) was chosen for use in subsequent rVSV/rISFV prime/boost experiments.

Figure 17:
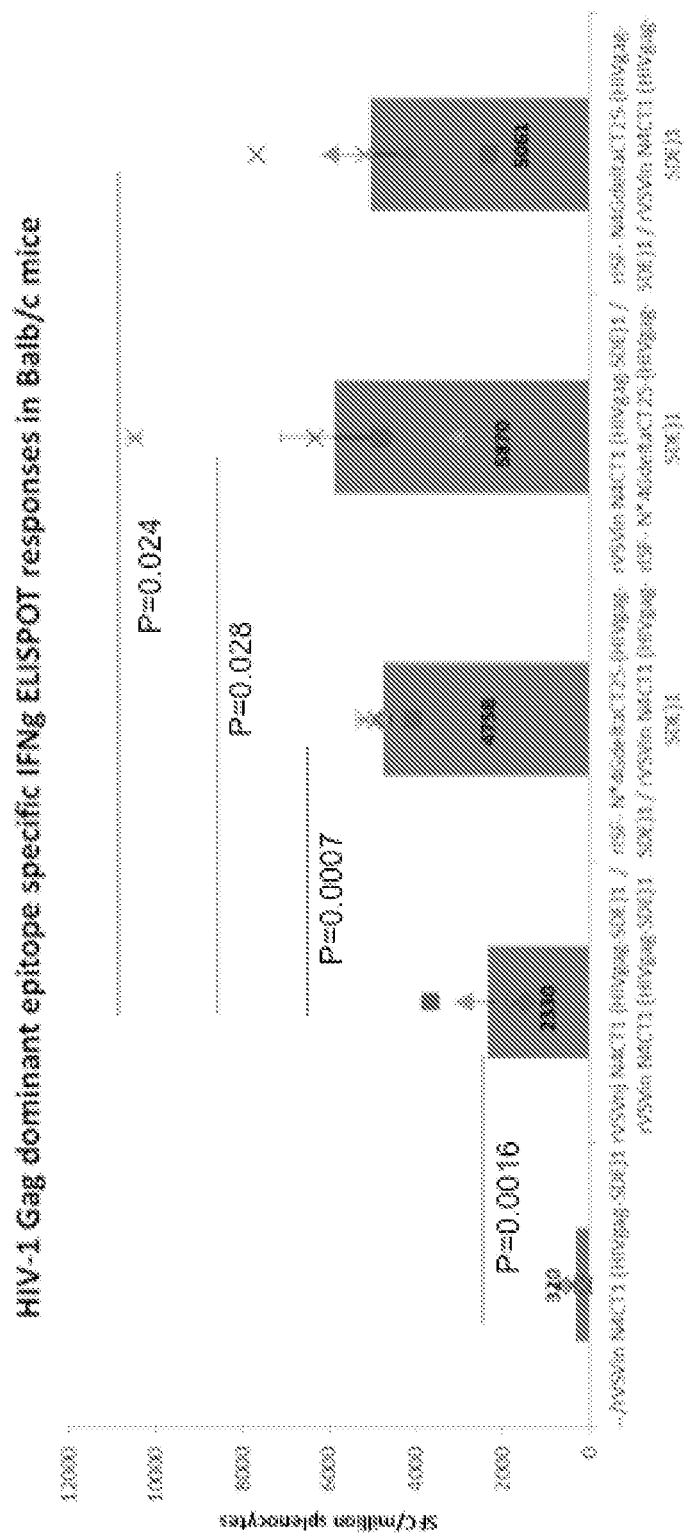
FIG. 17 illustrates IFN-γ ELISpot responses to an HIV-1 Gag single dominant epitope in the PBS-Mu-062b study.

PBS-Mu-062b: For this experiment, the relative immunogenicity was compared of various prime/boost immunization regimens using rVSV based vectors exclusively versus a combination of rISFV and rVSV based vectors. A summary of the PBS-Mu-062b study design is provided in FIG. 16. For this experiment, BALB/c mice (n=5/group) were immunized by intramuscular injection with 10$^7$ pfu of the rISFV HIV gag SDE expressing vectors outlined in FIG. 15 in combination with the rVSV$_{IN}$ HIV gag SDE construct (FIG. 12). Mice were immunized on a schedule of 0 and 4 weeks. One week after the final immunization, splenocytes were collected and tested for HIV gag SDE-specific (FIG. 17) and rVSV$_{IN}$ N peptide pool-specific (FIG. 18) IFN-γ secretion by ELISpot analysis. In this study, mice immunized with the rVSV$_{NJ}$/rVSV$_{IN}$ prime/boost regimen demonstrated an HIV gag SDE-specific ELISpot response (2,330±412 SFC/10$^6$ splenocytes) which was significantly lower (p<0.05) than the response seen in mice immunized with the heterologous rISFVN*/rVSV$_{IN}$ prime/boost regimen (4,758±183 SFC/10$^6$ splenocytes)(FIG. 17). This significant two-fold increase in the HIV gag SDE-specific IFN-γ ELISpot response compared to the rVSV$_{NJ}$/rVSV$_{IN}$ immunized mice was unaffected by switching the order of the heterologous regimen (rVSV$_{IN}$/rISFVN*; 5,870±1,258 SFC/10$^6$ splenocytes) or by the presence of a wild-type viral N gene in the rISFV vector (rISFV/rVSV$_{IN}$; 5,061±890 SFC/10$^6$ splenocytes) (FIG. 17). As shown in FIG. 18, the heterologous rISFVN*/rVSV$_{IN}$ and rVSV$_{IN}$/rISFVN* prime/boost regimens elicited significantly lower (p<0.05) mean rVSV$_{IN}$ N peptide pool-specific IFN-γ ELISpot responses (451±67 and 408±55 SFC/10$^6$ splenocytes, respectively) compared to the rVSV$_{NJ}$/rVSV$_{IN}$ (2,794±456 SFC/10$^6$ splenocytes) or the rISFV/rVSV$_{IN}$ (1,459±238 SFC/10$^6$ splenocytes) regimen.

The above mentioned studies clearly demonstrate that the heterologous rISFV/rVSV$_{IN}$ and rVSV$_{IN}$/rISFV prime/boost immunization regimens elicited significantly higher IFN-γ ELISpot responses than did the rVSV$_{NJ}$/rVSV$_{IN}$ immunization regimen in mice. Furthermore, the rISFV N* mutation reduced cross-reactive responses to rVSV N, although this did not result in an increase in the HIV gag SDE-specific IFN-γ ELISpot response.

EXAMPLE 5

Study of rISFV Vector Expressing Chikungunya Virus Glycoprotein in A129 Mice

Chikungunya virus (CHIKV) is a mosquito borne virus of the Alphavirus genus in the Togaviridae family. CHIKV infection in humans results in high fever, headache, vomiting, skin rash and painful arthritis. Arthritis, which can persist for months or even years (Powers and Logue. *J. Gen. Virol.* 2007, 88:2363-2377), is the hallmark of a generally self-limiting CHIKV infection. However, in recent epidemics in the Indian subcontinent and Indian Ocean islands, which affected over 1.5 million people, some people have displayed more severe symptoms including encephalitis, hemorrhagic disease, and mortality (Schwartz and Albert. *Nature Rev. Microbiol.* 2010, 8:491-500). The more recent and rapid spread of CHIKV into the Caribbean islands and the Americas (Powers. *J. Gen. Virol.* 2015, 96:1-5) has generated an even more urgent need for immunogenic compositions against CHIKV.

CHIKV has a single, positive sense, 11.8 kb RNA genome, which encodes four non-structural proteins (nsP 1-4) and five structural proteins (C, E3-E2-6K-E1). The structural proteins are cleaved from a precursor to generate the capsid and envelope glycoproteins (Strauss and Strauss. *Microbiol. Rev.* 1994, 58:491-562). The E2 and E1 proteins form a stable heterodimer and E2-E1 heterodimers interact to form the spike that is found on the virus surface. E2 is formed as a precursor called PE2 or p62 that is cleaved into E2 and E3. There is a small hydrophobic peptide called 6K that is produced as a linker between E2 and E1. When the E3-E2-6K-E1 polyprotein is processed, the E2 and E1 glycoproteins are produced, which then form the E2-E1 glycoprotein heterodimers (Strauss and Strauss. pages 497-499).

The starting point for constructing an attenuated rISFV vector expressing the E2-E1 glycoprotein was the plasmid designated pVSVΔG-CHIKV, which was received from Dr. John Rose (Yale University) (Chattopadhyay et al. *J. Virol.* 2013, 87:395-402). This plasmid contained an optimized Chikungunya E3-E2-6K-E1 genetic sequence (Genscript, Inc.) in place of the VSV G gene within the rVSV genomic cDNA. The CHIKV-E3-E2-6K-E1 sequence was amplified by PCR using the following primers:

```
Primer Alpha 001:
                                (SEQ ID NO: 69)
GGGCCCACTCGAGAACATGAGCCTGGCCATCCCCGTG
(contains XhoI site and Kozak sequence)

Primer Alpha 002:
                                (SEQ ID NO: 70)
61/
(Contains NotI site and NheI site)
```

The resultant PCR product was digested with Xho/NotI restriction enzymes and cloned into rVSVN4CT1 vector cDNA. This vector cDNA was then amplified and digested with XhoI/NotI restriction enzymes and the released insert encoding CHIKV-E3-E2-6K-E1 proteins was cloned into XhoI/NotI digested pPBS-ISFV-HIV-015 (described above in Example 2). Recombinant ISFV (rISFV) encoding CHIKV-E3-E2-6K-E1 proteins was then rescued from this pDNA as described above in Example 1. The result was a rISFV-N4 G-CTΔ25(CHIKV GP)1 designated pPBS-ISF-Alpha-003 virus expressing CHIKV-GP from the first position in the rISFV genome, and where CHIKV-GP represents CHIKV-E3-E2-6K-E1.

Rescued virus was plaque purified and amplified on Vero E6 cell monolayers (ATCC CCL-81). For animal studies, virus vectors were purified from infected BHK-21(ATCC CCL-10) cell supernatants by centrifugation through a 10% sucrose cushion. Purified virus was resuspended in PBS, pH 7.0, mixed with a sucrose phosphate (SP) stabilizer (7 mM $K_2HPO_4$, 4 mM $KH_2PO_4$, 218 mM Sucrose), snap frozen in ethanol/dry ice and stored at −80° C. until ready for use.

A study was performed to investigate the safety and efficacy of an immunogenic composition comprising the rISFV-N4G-CTΔ25(CHIKV GP)1 vector described above that expressed CHIKV-GP from the first position. Mice numbered 11-21 lacking the receptor for type 1 interferon (A129 mice) were immunized with $1\times10^7$ pfu of rISFV-N4G-CTΔ25(CHIKV GP)1 in their left footpad. The right footpad was not injected in order to serve as a control. A129 mice numbered 1-10 were not immunized as further controls. All 21 mice were injected in the left footpad with a 10 µl dose of $1\times10^4$ pfu of the LaReunion isolate of CHIKV and swelling was measured. The right footpad height was also measured as an internal control. The footpad heights of the left foot were not taken on the day of injection. Previous data showed that the sizes of the left and right feet were identical.

Figure 19:
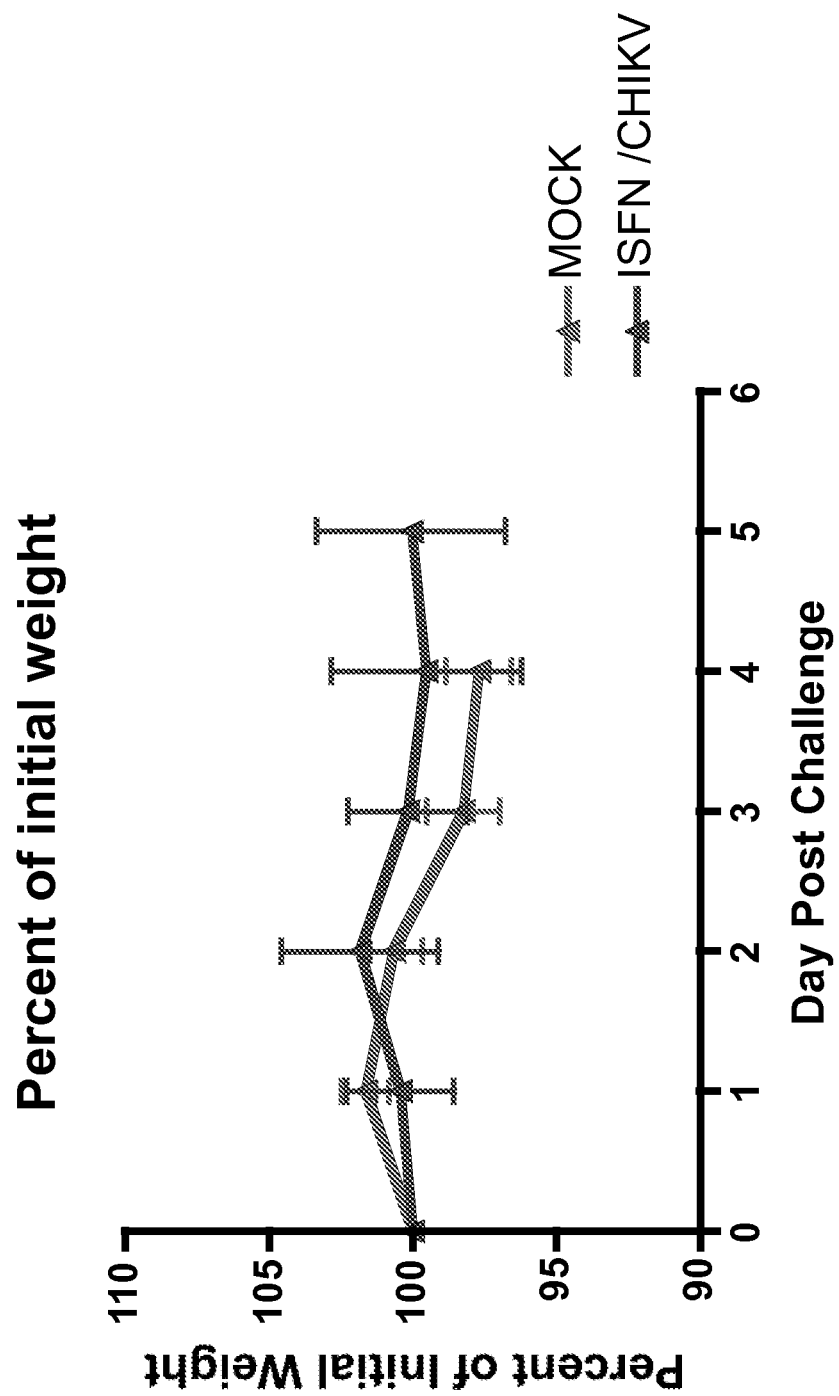
FIG. 19 depicts body weights of mice immunized with rISFV-N4G-CTΔ25(CHIKV GP)1 versus unimmunized mice after challenge with the LaReunion isolate of CHIKV.

As shown in FIG. 19, mice 11-21 immunized with rISFV-N4G-CTΔ25(CHIKV GP)1 maintained their body weights after challenge, while unimmunized mice lost weight through day 4 post-challenge.

Figure 20:
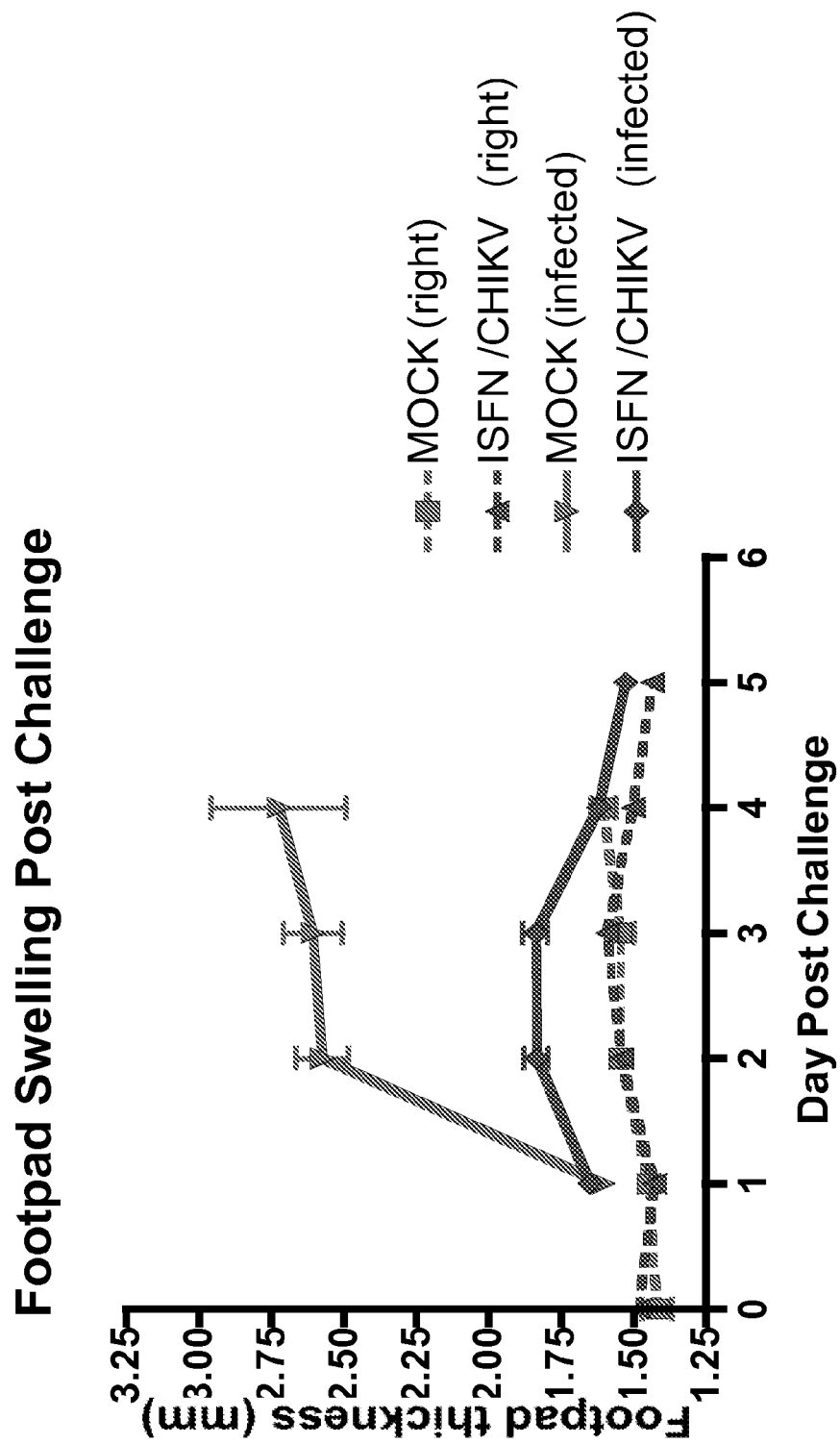
FIG. 20 depicts footpad swelling of mice immunized with rISFV-N4G-CTΔ25(CHIKV GP)1 versus unimmunized mice after challenge with the LaReunion isolate of CHIKV.

As shown in FIG. 20, immunized mice 11-21 had minor left footpad swelling by day 3 which resolved by day 5. In contrast, unimmunized mice 1-10 had left footpad swelling which continued to increase through day 4. Both groups of mice had no right footpad swelling.

Figure 21:
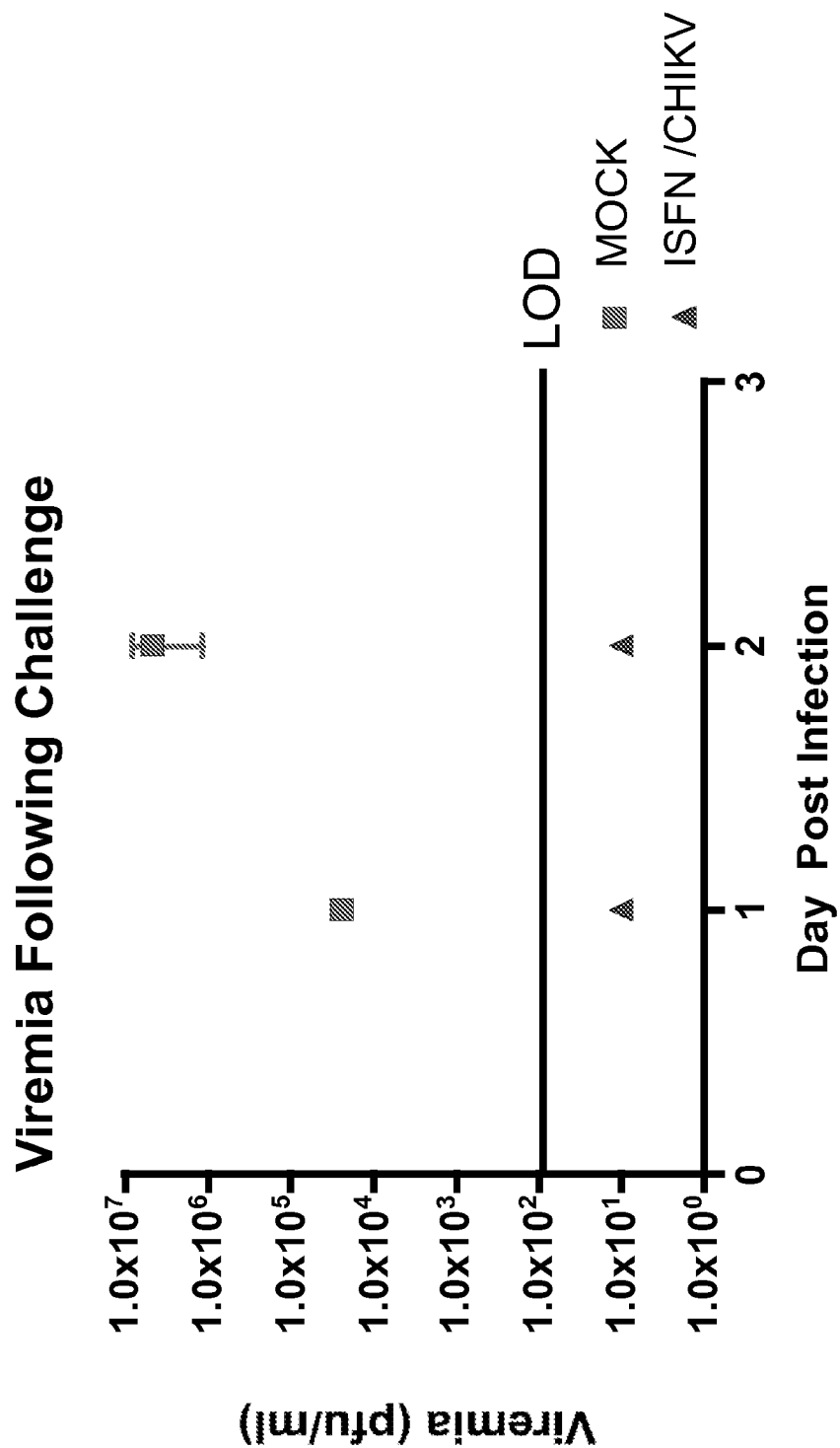
FIG. 21 depicts viremia of mice immunized with rISFV-N4G-CTΔ25(CHIKV GP)1 versus unimmunized mice after challenge with the LaReunion isolate of CHIKV.

As shown in FIG. 21, immunized mice 11-21 demonstrated no viremia in the blood on days 1 or 2 [below limit of detection of 100 pfu/ml]. In contrast, unimmunized mice 1-10 had signs of viremia on day 1, which increased to almost $1\times107$ pfu/ml by day 2.

Figure 22:
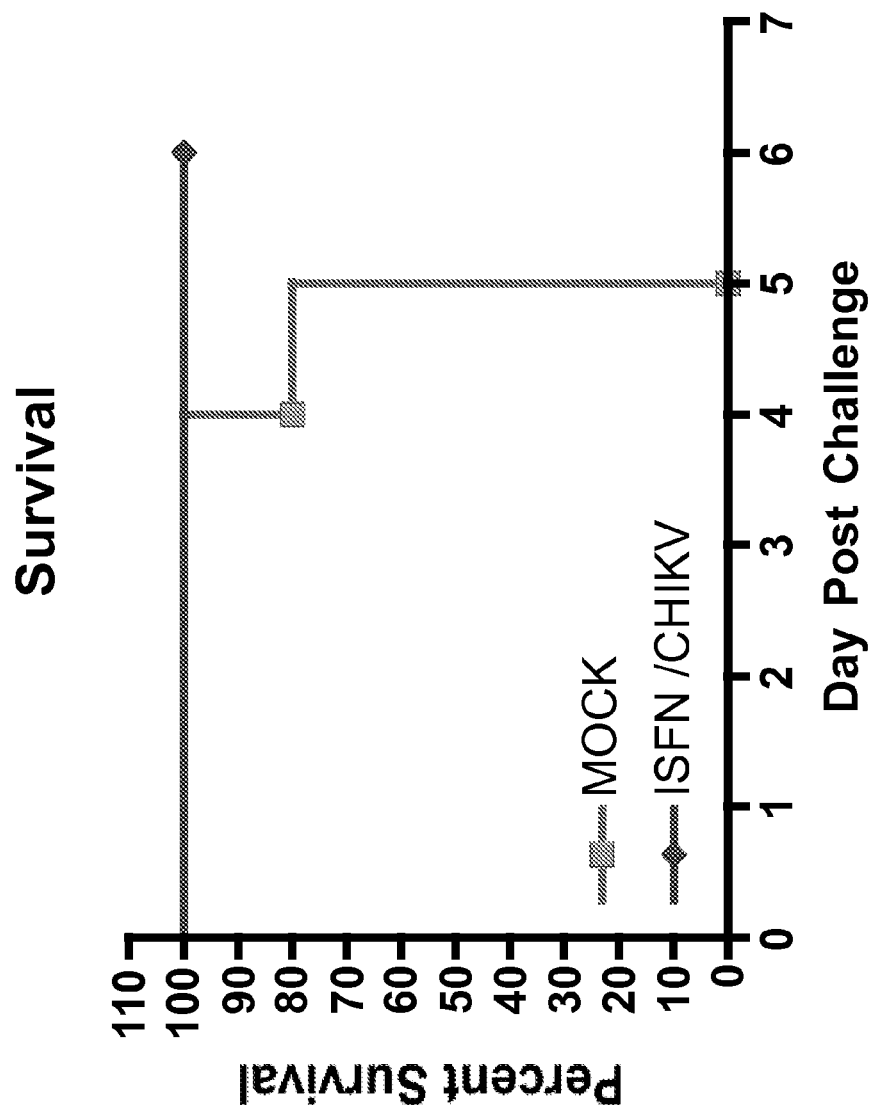
FIG. 22 depicts the survival of mice immunized with rISFV-N4G-CTΔ25(CHIKV GP)1, followed by lethal challenge with the LaReunion isolate of CHIKV.

By day 3, all unimmunized mice showed signs of illness, including footpad swelling, ruffled fur and lethargy. In contrast, all immunized mice were normal in appearance and behavior. As shown in FIG. 22, by day 5, all 10 unimmunized mice succumbed to illness. In contrast, all 11 immunized mice survived with no signs of illness.

All mice immunized with rISFV-N4G-CTΔ25(CHIKV GP)1 seroconverted by day 21 as determined by plaque reduction neutralization titers (PRNT80) from sera taken on days 1, 7 and 21 post-immunization as shown in Table 14 (bolded numbers indicate a positive result):

TABLE 14

Neutralizing antibody response against CHIKV in mice immunized with rISFV expressing Chikungunya glycoprotein

| Mouse Number | Day 1 | Day 7 | Day 21 |
| --- | --- | --- | --- |
| 11 | 1/20 | 1/20 | 1/40 |
| 12 | 1/160 | 1/40 | 1/80 |
| 13 | 1/20 | 1/40 | 1/40 |
| 14 | 1/40 | 1/20 | 1/40 |
| 15 | <1/20 | <1/20 | 1/40 |
| 16 | <1/20 | 1/20 | 1/40 |
| 17 | 1/40 | <1/20 | 1/40 |
| 18 | 1/20 | 1/20 | 1/40 |
| 19 | 1/40 | 1/40 | 1/80 |
| 20 | 1/320 | 1/80 | 1/80 |
| 21 | 1/40 | 1/40 | 1/40 |

The invention claimed is:

1. A recombinant replication competent Isfahan virus comprising an N protein gene, a P protein gene, an M protein gene, a G protein gene, and an L protein gene; and further comprising a heterologous polynucleotide sequence encoding a heterologous polypeptide.

2. The Isfahan virus of claim 1, wherein the heterologous polynucleotide sequence is flanked by a transcription start signal and a transcription stop signal.

3. The Isfahan virus of claim 1, wherein the heterologous polynucleotide encodes an immunogenic polypeptide.

4. The Isfahan virus of claim 1, wherein the heterologous polynucleotide encodes one or more antigens.

5. The Isfahan virus of claim 4, wherein the antigen is a viral antigen, a bacterial antigen, a tumor-specific or cancer antigen, a parasitic antigen or an allergen.

6. The Isfahan virus of claim 5, wherein the antigen is a viral antigen.

7. The Isfahan virus of claim 1, wherein the heterologous polynucleotide sequence is located at position 1, 2, 3, 4, 5 or 6 of the Isfahan virus genome.

8. The Isfahan virus of claim 1, wherein the N protein gene is located at position 1, 2, 3, 4 or 5 of the Isfahan virus genome.

9. The Isfahan virus of claim 1, wherein the G protein gene encodes a G protein having a carboxy-terminal truncation.

10. The Isfahan virus of claim 9, wherein the G protein has a carboxy-terminal truncation of 20 to 25 amino acids.

11. The Isfahan virus of claim 1, wherein the heterologous polynucleotide sequence is located at position 5 and the N protein gene is located at position 4 of the Isfahan virus genome.

12. An isolated host cell comprising the Isfahan virus of claim 1.

13. An immunogenic composition comprising a recombinant replication competent Isfahan virus comprising an N protein gene, a P protein gene, an M protein gene, a G protein gene, and an L protein gene; and further comprising a heterologous polynucleotide sequence, wherein said heterologous polynucleotide sequence encodes a heterologous polypeptide; and a pharmaceutically acceptable diluent, excipient or carrier.

14. The immunogenic composition of claim 13, wherein the heterologous polynucleotide sequence is flanked by a transcription start signal and a transcription stop signal.

15. A method of inducing an antigen-specific immune response to an antigen in a mammalian subject comprising administering the immunogenic composition of claim 14.

16. An immunization kit for inducing an antigen-specific immune response in a mammalian subject, said kit comprising:
(a) a priming composition comprising a recombinant replication competent Isfahan virus encoding an N protein gene, a P protein gene, an M protein gene, a G protein gene, an L protein gene, and a heterologous polynucleotide sequence, wherein said heterologous polynucleotide sequence encodes a heterologous polypeptide, wherein said heterologous polynucleotide sequence (i) is flanked by a transcription start signal and a transcription stop signal, and (ii) encodes a heterologous polypeptide; and a pharmaceutically acceptable diluent, excipient or carrier; and
(b) a boosting composition comprising a recombinant replication competent vesicular stomatitis virus encoding an N protein gene, a P protein gene, an M protein gene, a G protein gene, an L protein gene, and a heterologous polynucleotide sequence, wherein said heterologous polynucleotide sequence (i) is flanked by a transcription start signal and a transcription stop signal, and (ii) encodes a heterologous polypeptide; and a pharmaceutically acceptable diluent, excipient or carrier.

17. A method of inducing an antigen-specific immune response in a mammalian subject comprising administering the immunogenic compositions of claim 16.

18. An immunization kit for inducing an antigen-specific immune response in a mammalian subject, said kit comprising:
(a) a priming composition comprising a recombinant replication competent vesicular stomatitis virus (VSV) encoding an N protein gene, a P protein gene, an M protein gene, a G protein gene, an L protein gene, and a heterologous polynucleotide sequence, wherein said heterologous polynucleotide sequence encodes a heterologous polypeptide, wherein said heterologous polynucleotide sequence (i) is flanked by a transcription start signal and a transcription stop signal, and (ii) encodes a heterologous polypeptide; and a pharmaceutically acceptable diluent, excipient or carrier; and
(b) a boosting composition comprising a recombinant replication competent Isfahan virus (ISFV) encoding an N protein gene, a P protein gene, an M protein gene, a G protein gene, an L protein gene, and a heterologous polynucleotide sequence, wherein said heterologous polynucleotide sequence encodes a heterologous polypeptide, wherein said heterologous polynucleotide sequence (i) is flanked by a transcription start signal and a transcription stop signal, and (ii) encodes a heterologous polypeptide; and a pharmaceutically acceptable diluent, excipient or carrier.

19. A method of inducing an antigen-specific immune response in a mammalian subject comprising administering the immunogenic compositions of claim 18.

20. A recombinant replication competent Isfahan virus comprising an N protein gene, a P protein gene, an M protein gene, a heterologous viral surface protein gene(s), and an L protein gene.

21. The recombinant replication competent Isfahan virus of claim 20, further comprising a second heterologous polynucleotide sequence, wherein said heterologous polynucleotide sequence encodes a second heterologous polypeptide.

22. The recombinant replication competent Isfahan virus of claim 20, wherein the heterologous viral surface protein gene replaces the Isfahan virus G protein gene.

23. The recombinant replication competent Isfahan virus of claim 20, wherein the heterologous viral surface protein gene is a G protein gene of vesicular stomatitis virus.

24. An oncolytic viral composition comprising a recombinant replication competent Isfahan virus comprising an N protein gene, a P protein gene, an M protein gene, a G protein gene, and an L protein gene, wherein said Isfahan virus is used as an anti-cancer therapeutic.

25. The Isfahan virus of claim 6, wherein the viral antigen is from Chikungunya virus.

* * * * *

SEQUENCE LISTING

<160> NUMBER OF SEQ ID NOS: 90

<210> SEQ ID NO 1
<211> LENGTH: 11088
<212> TYPE: DNA
<213> ORGANISM: Isfahan Virus

<400> SEQUENCE: 1

| | | | | | |
|---|---|---|---|---|---:|
| acggagaaaa | acaaaccaat | tcacgcatta | aagattcca | gaggaaagtg | ctaacaggga | 60 |
| tcaaaatgac | ttctgtagta | aagaggattg | ctactggctc | aagtgtgttg | gcagtactac | 120 |
| ccgccaatga | agaccctgta | gagtttccag | gggactattt | tttgcaaaat | ccgggaaaaa | 180 |
| taagggtgtg | catcaacaga | aaattagacg | ttgccacact | ccgccaatac | gtctacgagg | 240 |
| gactaaaaaa | tggggatgtc | catgtgtgtc | acatcaattc | atacctgtac | caggtgctca | 300 |
| aagacaccag | agatgaggcc | caaagtgatt | ggatatcttt | cggagtgtcc | cttgcagtca | 360 |
| aaggtggcat | tgtcagtgta | tttgacaccc | ttatgattga | ggattacagg | ggagaggctc | 420 |
| cggatgggag | gaaatgcgat | ggaagaacca | tcgacgatga | caaatggctg | ccaatgttaa | 480 |
| tcctcggcct | atacagggtg | tcgagagcga | cacaagaaga | ctacaaaaag | tcactactgc | 540 |
| agaaactcta | cgctcagtgc | aagctgagga | gtcctcaagc | tgaagaatta | gttgaagacg | 600 |
| cagcagaatt | ttatgaagtt | tggtccaatg | attcaaactt | cctaaaattg | gttgcagcaa | 660 |
| ttgacatgtt | ctttcacaaa | ttcaaaaacc | atgcagatgc | aggcttgaga | tggggaacca | 720 |
| ttgtgtcacg | atttaaagat | tgtgccgcct | tggcaacatt | gtctcatgta | cagaaagtga | 780 |
| ctggcctgtc | aatcaaagaa | gtgttcacct | gggttctgaa | caaatcagtt | aagatgagt | 840 |
| tgtgcagaat | gatgaaagaa | agacaagaag | tggacaaagc | tgattcctac | atgccttacc | 900 |
| tgattgattt | cgggatctca | acaaaatccc | cctattcatc | agtaaagaac | ccgtgttttc | 960 |
| atttctgggg | acaactgaca | gcactgctgg | tccactctca | cagagctaaa | aacgcaaggg | 1020 |
| tcccagaaga | catcccttat | aatgagctga | ctacagcagc | atggctgttc | gcttatgcaa | 1080 |
| tgggaagatc | atccggattg | gaacagcggt | tcacgacgga | tgacagttat | tatcaggaag | 1140 |
| atgaggatat | caacaaagga | ctcggagtca | aagctcccac | cacaagagat | gtgcaaatgt | 1200 |
| ggttggcctg | gtggagtgac | atcggtaagg | ttccaacaca | ggacatggaa | acattcgcaa | 1260 |
| gacgtgaggt | attgggcctc | acagagatca | gatcaaaaac | tattggtgag | tatgccaaga | 1320 |
| agacattcag | tgtctaagaa | ttcaaatcaa | catatatgaa | aaaaatcaac | agagatacaa | 1380 |
| caatgtctcg | actcaaccaa | attttgaagg | attaccctct | gttagaggcc | acaacatctg | 1440 |
| agattgagag | tatggaatcc | tcattggctg | atgatgttat | cacctcgaat | gacgatgaaa | 1500 |
| ttcaaagtgt | gtcctctcaa | tattacctcc | gtgatatgtt | taaggcgagc | atcacggaag | 1560 |
| gtcctgatga | tgacttccct | ccggtgccag | aggtcgagaa | tgacatcatc | ttagatgacg | 1620 |
| atgaggaata | tgatggatat | aaagtggatt | ttgcagaagc | cagaccctgg | actgcactga | 1680 |
| cccagaagaa | tatagatgga | aggatgaacc | tggaattgat | ggctccggaa | aacctcactg | 1740 |
| acgctcagta | caaacaatgg | gtggaaagtg | tttcttccat | catgacaatt | tcccgtcaga | 1800 |
| tccgattgca | tcaggcagag | atcatggaca | cttcatcagg | gcttctaatc | attgagaaca | 1860 |
| tgattccatc | cataggcagg | acatcagagt | tcaaatccat | tccagagcat | attcctccga | 1920 |
| gcccgacgtc | agatcacacc | actccaccct | cgagcttacg | gtcagatacc | ccgagtcaaa | 1980 |
| catcatctag | cagcatgggg | ttacctgatg | tcagttctgc | ttcagattgg | agcggaatga | 2040 |
| tcaacaaaaa | gatccggatc | ccgcccgttg | tcagttcaaa | atctccgtat | gaattcaccc | 2100 |

```
tttctgatct gtatggatca aatcaggctg ctcttgatta cttaagtgga tcagggatgg      2160
acctgaggac agctgtgtgc tcagggctca acagagagg gatctacaat cgaattagga      2220
ttcagtacaa gataacccca gaattcgtat gattttgatc aaagaaactg actgaggctc      2280
aaactacaat atagctgcaa caattgcaat tgtttcgtga ttgaaatgta tgaaaaaat      2340 taacagaggt caaatctgtt tcacaaccat gaagagctta agagactga ttaagtcgaa       2400 caaaagaag ggagacaaga aaaatgtctc cttcatggat tgggatgagc ctcctagtta      2460
ctcagactct agatatggat gctatccttc tgctcctttg tttggagtgg atgaaatgat     2520
ggaaacactt cccactctgg ggatccaatc attaaagatt cagtataaat gcagcctaca     2580
ggtcagggct gagactcctt tcactagctt caatgatgcc gcccggtgca ttagcctctg     2640
ggagactgat tatcgaggct acgctgggaa gaaacccttc tatcgtctcc ttatgttgat     2700
tgctacaaaa aaactcagag cagctccgat gagtctaatg gatggcaaca ggcctgaata     2760
tagctctatg attcaaggtc aatcaattgt ccaccacagt ctgggagtca ttcctcctat     2820
gatgcatgtg cctgaaacat tcacaagaga atggaatttg ctgacaaata aaggaatgat    2880
cacagctcaa atctggctag ggatcacaga tgttgtagat gatctcaatc cattgatcaa    2940
tccagcactc ttctcagatg agaaagaaat gactcttacg agtcagatgt tcgggttgga   3000
gctcaaaaag aggaatgata atacatggtt gatcagtaag agctattgat caactgaaga   3060
gttggtgatc gaattataac atgcagaaga aagatatgaa aaaaattaac agaggtcaaa    3120
atgacttcag tcttattcat ggttggtgtg ctcttggggg cctttggttc aacccattgt    3180
agtattcaaa tcgttttccc cagtgaaaca aaactcgtat ggaagccagt attaaaaggg   3240
accaggtact gtccacaaag tgcagaatta aatctggaac ccgacttgaa aactatggct    3300
tttgacagca agttccaat tggcataacg ccttccaact cggatggcta cctgtgtcat    3360
gctgccaaat gggtcacaac atgtgatttt cgatggtatg gaccgaagta cataactcac   3420
tctgtccaca gcttgagacc aacagtttct gattgtaaag cggccgtaga agcttacaat   3480
gctggtactc tcatgtaccc gggttttcct cctgaatctt gtggatatgc atctatcacg   3540
gattctgaat tttatgtcat gctagtaact ccgcatcctg ttggagtgga tgattacaga   3600
ggacactggg tggatccatt gttttcctact agcgagtgca attccaattt ttgtgagact   3660
gttcacaatg ccactatgtg gatcccgaaa gatcttaaaa ctcatgatgt tgttctcag   3720 gacttccaga cgattagggt ttccgtgatg tatcctcaaa ccaaacccac caaggggggca   3780 gacttgacac tgaaaagtaa gttccatgct cacatgaaag gtgacagagt ctgcaagatg    3840
aaattctgca acaaaatgg gttgcgactg ggaaacggag aatggattga agttgggat    3900 gaggtcatgc tcgataactc gaaactcttg agtttattcc cagattgttt ggttggttct    3960
gtggtaaaat ccactttgct ctcggaagga gttcaaacag cactgtggga gaccgacaga   4020
ctattagatt actcattgtg ccagaacaca tgggaaaaaa tcgatcgaaa agagccgctg   4080
tctgctgtgg acctgagcta tcttgcacct agatcacccg gaagggggat ggcatacatc   4140
gttgccaatg gatctttgat gtctgctcct gctagataca tcagagtttg gattgacagt   4200
cccatactta aggagataaa aggaaagaaa gagtcagcct ccggaattga cactgtcctt   4260
tgggaacaat ggctcccctt caatggaatg gagttaggac ctaatggatt gatcaagacg   4320
aagtcaggtt acaaatttcc gctatatctt cttggaatgg gcattgtaga tcaagatctt   4380
caagagttgt cctcagtgaa ccctgtagac cacccacatg taccaattgc ccaggctttc   4440
```

```
gtttcagagg gagaagaagt cttctttggg gatacaggag tctctaaaaa cccaatcgag    4500
ctgatatctg gctggttctc agattggaaa gaaacagcag ccgcattagg gttcgctgca    4560
atatctgtga tcttaattat tggactaatg aggctgttgc cactattatg caggaggaga    4620
aagcaaaaaa aagttatcta caaagacgta gaattaaatt cttttgatcc tagacaagct    4680
tttcacagat gaaagtatga aaaaaacgaa tcaacagagt tcatcatgga tgagtactct    4740
gaagaaaagt ggggcgattc tgatgaagaa tcttttggca cagggaaata ttctgacgag    4800
tctagaataa gaggattaaa ttctgttgac tataatctaa actctcccct aattcaagat    4860
gatctgtact atctaatgga acgagtgcgt ggaagaccgg tacctcccat ttggaaagca    4920
aaaaattgga ccgaaactat acatctggtt caagaaagta gattagatta tttaccaaca    4980
cagaagctac acagttggta tgcggaatgg ctcatggagg agagtcatga ctcctctcaa    5040
ggactagcat tcttgaagga agtggacaaa gacagtttgg aaacatacga agttgttatg    5100
tcattcctaa ggggctggtg tggtggtgct ccggcgtata aaagaaaga agggcgacac    5160 atagcaaaga taggatcatt atgccagaaa ttcttggatc tccaccgagt catacttata    5220
atgaatgctt ctacccagat ggagttgtca aatttggcag agacatttca ggcctcttct    5280
gtgtcaaaga aaattattac aacaccctca atgggaaaga tggagatgag tggacaattt    5340
gcacttgcat accagcaaaa agtcatactt gatagaaact tcttattaat gatgaaagat    5400
gttgtgattg aaggatgca acattgttg tccatggttt ctcgaacaga tgacaagttc    5460
tctgatgggg acattagtta cttaatcaag atttatcaat tgggtgataa aatcattcaa    5520
tcgctaggaa atgatggata tgagctgatt aaaacaatag agcccatgtg caacttgaga    5580
ctgtctgatt tagccagaga atatcggcct ctcataccgg agttccctca ctttcgccag    5640
catatcgagg gaaccgtgtc agagctcaga aaaaagactg cgttgattgt agacatgttc    5700
aagatgatag atcggacacc aggagtggat ataacattag taatatacgg atctttccgt    5760
cattggggcc atcccttcat tgattatttt gcggggttga caaaattgaa ttcccaagtc    5820
actatgggga aacagattga tgatgagtat gtggcctgcc tggcaagtga cttggcaaga    5880
attgtgctca ctaaggaatt caatgagaaa aagagatgga gtgtgaacta caatttagtt    5940
cctcaggatc atccttttca tgaacacatc cgagacaata catggcctac tccagccgtg    6000
atacaagatt tggggacaa atggcatgag ttaccactca ctcaatgctt tgaaattcct    6060
gatttgatag acccttctat catctactcg gataaaagtc actccatgaa tcgacaagat    6120
gtactaaatc atgtaaagag aaaaccagat caacctatac ctagcaggaa agttttgcaa    6180
actatgatag atacacctgc cactaactgg ttggagtttt tggaagaaat tgacaaaaat    6240
gggttgagtg atgatgacct ggtgattggg ctaaaaggga aggaaagaga attgaagata    6300
gccgggagat ttttctcact aatgtcgtgg aagctgagag aatattttgt gatcacggaa    6360
tatctaatta agacacactt tgtaccactt ttccacggct tgacaatggc agatgacatg    6420
acggctgtaa taagaaaat gttggaaagt tcaagtggac agggtctaaa agattattcg    6480
gcagtatgca ttgcaaacca cattgactat gagaaatgga acaaccatca gaggaaacgg    6540
tcaaatgaac caatttttaa agtcatgggt caattcttgg ggtttcccaa ccttatatcg    6600
aggactcatg aattctttga gaaaagtctc atctattata tggaaggcc tgatttgatg    6660 aaggtgcaag atggaagact tgtgaacaca acgaagcaat ggtttgttg ggaaggacag    6720 gcaggcggat tagaggggtt aagacagaag ggatggagca tcttaaactt attggttatt    6780
caaagggaat ccaagattcg gaacacagca gttaaagtcc ttgcacaagg tgataatcaa    6840
```

| | | | | | |
|---|---|---|---|---|---|
| gtaatatgca | cacagtacaa | gacaaaacaa | cacagaaatg | aaacagaatt | gcgatctgct | 6900 |
| cttactcaaa | tgaaattgaa | taatgatgca | gttatgaaag | ccattgaatc | tggaacaaac | 6960 |
| aaactaggtt | tgttgatcaa | ccaagatgaa | acaatgcaat | cagctgacta | cctgaattac | 7020 |
| ggtaaagttc | ccatatttag | aggagtgata | cgaggtttag | aaacaaaaag | gtggtcacga | 7080 |
| gtgacttgtg | taacaaatga | ccaacttccc | acctgtgcaa | acttgatgtc | atcagtgtct | 7140 |
| actaatgccc | ttactgttgc | tcattttgat | gtgacaccct | tgaatgcgat | gatacagtac | 7200 |
| aattatttcg | gaaattttc | tagattgctc | ctcaacatgc | atgatcctgc | tgtgagatgt | 7260 |
| tcactctttc | agctctctca | aaaacacaag | atagatttat | tcagtttcga | atttaaagtt | 7320 |
| ggggtgttgt | atttggatcc | ttctatcgga | ggtgtttgtg | gaaccgcatt | atccagattc | 7380 |
| ttaattcgcg | gatttccaga | tccggtgacc | gaaagcatat | cattctggaa | agtaatttat | 7440 |
| aacaataccc | aagacaacag | attgaagaag | ttgtgtacag | cattcggaaa | tcccaaaatt | 7500 |
| gctcaattcc | gctattcgca | catagagaaa | ttgttggaag | atcctacgag | cttgaatata | 7560 |
| tcgatgggca | tgagtgcagc | caacctgttg | aagagcgaaa | ttaagaagaa | ccttctgcgg | 7620 |
| aaaagaagga | ctattgggaa | tagcattgtt | agggacgccg | taacctatat | acactctgaa | 7680 |
| gacgaaaaga | tcagatctta | cttgtggagt | ataaatcctc | tattccccag | atttttgagt | 7740 |
| gaattcaaat | caggcacttt | catgggagtt | gcatctagtg | tggtcagcct | atttcagaac | 7800 |
| tccagaacca | ttagaaatgt | ttttaaagat | tatatgagtt | ctgcgattga | tgagttgatt | 7860 |
| accaaaagtg | aagtgaactc | cttggagcat | ttgtgtaaat | ataagggtgt | ccgcaatttc | 7920 |
| gatcaagtct | ggaaatgttc | tgctagccag | gctgattatt | tgaggagatt | atcctggggt | 7980 |
| agaaaagttc | ttgggactac | aatccctcat | ccattagaaa | tgcttggagc | gggcacaatc | 8040 |
| aagaataatt | cctccacttg | ttgtgagcat | tccggccagg | attacatctc | ggtattttgt | 8100 |
| cccaaaggaa | taagcaatgt | gctcatagaa | agaggcccta | tggcagcata | cctagggtca | 8160 |
| aaaacatctg | agtctacttc | tattcttcaa | ccatgggaga | agagagcaa | atcccgatc | 8220 |
| atcaaaagag | ctactcgatt | aagagatgcc | attcattggt | ttgtggagcc | aagctccaac | 8280 |
| ttggcaaaga | gcatcttgca | aaacatcaca | gcactaacag | gagaagagtg | gggatcatca | 8340 |
| ctagaaggat | ttaagagaac | ggggtctgct | ctccatagat | ttaccacatc | acgaatgagc | 8400 |
| catggaggct | tttgtgccca | aagcccggct | gcattgacaa | ggatgatggc | aaccacagat | 8460 |
| acaatgagcg | actatgcaaa | agacaattat | gattttatgt | tccaggcttg | tctcctcttt | 8520 |
| tctcagataa | ccacttcggt | tttactcctt | gaaaccacaa | tttcaaatac | tgtacatttt | 8580 |
| cacactcggt | gtataaattg | tgtgagaaag | atagaggagc | cgtggctgga | aagtccaagt | 8640 |
| gtactccaga | gcaaggacgt | atcaaacgta | ttagcaagct | ggagaaatgg | aggaggatca | 8700 |
| tggggtgaac | agctgcatca | attaaaacct | ctcaaaggag | attgggagat | attaactcct | 8760 |
| gcggagaaat | cataccatgt | cgggagaact | ctaggatttt | tgtttggcga | tctaacaggt | 8820 |
| cagtcatcga | ttagagccga | tgatagttcc | ttattcccct | taagcataca | aaaacggctg | 8880 |
| cgaggacgag | ggtttcttag | aggagttttg | gatgggttgg | tgagggcaag | tgcatgccaa | 8940 |
| gttatccata | gaagaagcct | gacacaactg | aagagacctg | ccaatgccgt | gtacggagga | 9000 |
| ttgatattct | tgattgacaa | aatcagcgct | tcatccacct | tcatcaattt | atgccgagat | 9060 |
| ggaccaataa | gagaagaact | ctccagtatc | ccacataaaa | ttcctacatc | atatcctaca | 9120 |
| tctaatgcgg | atcgaggact | gcatataagg | aattacttca | aatttcagtg | taagtctgta | 9180 |

```
gagttgggga aatatcaatc agatttggaa gatttatggc ttttctctga cttgctatct    9240
tcaggattcg ccggacctta tgctttatca tcaaaagttt taaagagcct atataaaccc    9300
tccctatcta gaagggatag aacaatatc cgaaaattgg gtgctttgtc tcggttattg     9360
agatcacatg agaactggtc agaattgcat aaagaattct taacatcgca attgttattg    9420
tgccaagagg aggtgcgcca cgcatgcaaa tttggtatcc caaaaaatgt ctccgccaaa    9480
tcatcaatgg tatggggaa agaagcagtg tcgtatgtac tagacattcc agttgagttc     9540
acatcccaaa aacagaccaa acatttgaac gcttgcccgc gtattcagga cccgacaatt    9600
tctggattaa ggcttggaca gttgcccacc ggggctcact acaagattag gacaattctc    9660
aatgcttaca atattaagtg tcgggatgtc ctatgtggag gtgatggatc cggaggaatg    9720
actgctgcat gcctgcgata ttattctaat tcaagggcaa tatttaatag cattcttgag    9780
ttcgatggat caagcatgaa agggtcatca cctgatcctc caagtgcatt ggaaacagta    9840
gatcaaggga tggtacgctg tgttaatgct acaacatgtt gggagaatcc atccgacttg    9900
agtcaagagc ggacatggga ttattttttg catttgaaga agagttttaa catgaagatc    9960
gatcttatca ttcttgatat ggaagttaga gacttccaaa tttcaaagct gatagaagga   10020
aatttaagat tgaaaatctc aaaactgctg aaaagaatg tactttaat ctataaaacg      10080
tatggcacaa tcatctgctc agagacctca aatgtattaa caaccttggg tccactcttt   10140
cactctgttt atatcgtcca aactgggtat agcagctcat tcacttctga ggtttatgta   10200
ctgttttcta agcaaaagtc ttttgttgat tctccatatg tagattgggg atcattacaa   10260
tataattggg agaagctggc ctgttttagg aacccaagac aagaattcaa gagggcctta   10320
agaattagaa gtagtagatc tttgatggga ataccctcat ccttcttgcc tgatccattg   10380
gtgaatctgg aaacccttct tcaaatatca ggtgttccct ctggagtgtc tcaccaactg   10440
gtcactgacg ttaaaagttc tggggcatcc ggcttgtctt cagctatagg gttgctagga   10500
ttaatttctc acttcacttt agacgtgacc aaattatacg tacaagagta tcgaccacct   10560
tctgacaatc gcctaataaa aatggctagt gcaatcaccg ggattagtta ttggatttca   10620
atagcctacc atgatcaaca attaaatcaa gcactaacct cagtaatcaa gaaatcattt   10680
cctatacgtt ggggacttat aaatcatcga ctccactgga gtgtttctga tagatttcac   10740
cgatcgaaag acgttcgatt atctgattgc ctagcaggta taggaaactg gatccgaggc   10800
atggagttga tgaagctgcc tgcaggcatg ttttcacaca aggaagtcaa tatgatcttg   10860
tcaaaatata ttcgcggttt aaattatcat acaatatcaa gcaggacagg aattcttgag   10920
attttgaaat ctcaattctc tattattgat cgatctttga tgaccattac cacagacaac   10980
attcagtcgt cagattggac agattaatca tatgaaaaaa actaaaaatc ggactaagca   11040
cgctcacttg ttttactata atacgttagc tggttttgtt gtctccgt                11088
```

<210> SEQ ID NO 2
<211> LENGTH: 423
<212> TYPE: PRT
<213> ORGANISM: Isfahan Virus

<400> SEQUENCE: 2

Met Thr Ser Val Val Lys Arg Ile Ala Thr Gly Ser Ser Val Leu Ala
1               5                   10                  15

Val Leu Pro Ala Asn Glu Asp Pro Val Glu Phe Pro Gly Asp Tyr Phe
            20                  25                  30

Leu Gln Asn Pro Gly Lys Ile Arg Val Cys Ile Asn Arg Lys Leu Asp

```
            35                  40                  45
Val Ala Thr Leu Arg Gln Tyr Val Tyr Glu Gly Leu Lys Asn Gly Asp
 50                  55                  60
Val His Val Cys His Ile Asn Ser Tyr Leu Tyr Gln Val Leu Lys Asp
65                  70                  75                  80
Thr Arg Asp Glu Ala Gln Ser Asp Trp Ile Ser Phe Gly Val Ser Leu
                85                  90                  95
Ala Val Lys Gly Gly Ile Val Ser Val Phe Asp Thr Leu Met Ile Glu
            100                 105                 110
Asp Tyr Arg Gly Glu Ala Pro Asp Gly Arg Lys Cys Asp Gly Arg Thr
        115                 120                 125
Ile Asp Asp Asp Lys Trp Leu Pro Met Leu Ile Leu Gly Leu Tyr Arg
    130                 135                 140
Val Ser Arg Ala Thr Gln Glu Asp Tyr Lys Lys Ser Leu Leu Gln Lys
145                 150                 155                 160
Leu Tyr Ala Gln Cys Lys Leu Arg Ser Pro Gln Ala Glu Glu Leu Val
                165                 170                 175
Glu Asp Ala Ala Glu Phe Tyr Glu Val Trp Ser Asn Asp Ser Asn Phe
            180                 185                 190
Leu Lys Leu Val Ala Ala Ile Asp Met Phe Phe His Lys Phe Lys Asn
        195                 200                 205
His Ala Asp Ala Gly Leu Arg Trp Gly Thr Ile Val Ser Arg Phe Lys
    210                 215                 220
Asp Cys Ala Ala Leu Ala Thr Leu Ser His Val Gln Lys Val Thr Gly
225                 230                 235                 240
Leu Ser Ile Lys Glu Val Phe Thr Trp Val Leu Asn Lys Ser Val Glu
                245                 250                 255
Asp Glu Leu Cys Arg Met Met Lys Glu Arg Gln Glu Val Asp Lys Ala
            260                 265                 270
Asp Ser Tyr Met Pro Tyr Leu Ile Asp Phe Gly Ile Ser Thr Lys Ser
        275                 280                 285
Pro Tyr Ser Ser Val Lys Asn Pro Cys Phe His Phe Trp Gly Gln Leu
    290                 295                 300
Thr Ala Leu Leu Val His Ser His Arg Ala Lys Asn Ala Arg Val Pro
305                 310                 315                 320
Glu Asp Ile Pro Tyr Asn Glu Leu Thr Thr Ala Ala Trp Leu Phe Ala
                325                 330                 335
Tyr Ala Met Gly Arg Ser Ser Gly Leu Glu Gln Arg Phe Thr Thr Asp
            340                 345                 350
Asp Ser Tyr Tyr Gln Glu Asp Glu Ile Asn Lys Gly Leu Gly Val
        355                 360                 365
Lys Ala Pro Thr Thr Arg Asp Val Gln Met Trp Leu Ala Trp Trp Ser
    370                 375                 380
Asp Ile Gly Lys Val Pro Thr Gln Asp Met Glu Thr Phe Ala Arg Arg
385                 390                 395                 400
Glu Val Leu Gly Leu Thr Glu Ile Arg Ser Lys Thr Ile Gly Glu Tyr
                405                 410                 415
Ala Lys Lys Thr Phe Ser Val
            420

<210> SEQ ID NO 3
<211> LENGTH: 289
<212> TYPE: PRT
<213> ORGANISM: Isfahan Virus
```

<400> SEQUENCE: 3

```
Met Ser Arg Leu Asn Gln Ile Leu Lys Asp Tyr Pro Leu Leu Glu Ala
1               5                   10                  15

Thr Thr Ser Glu Ile Glu Ser Met Glu Ser Ser Leu Ala Asp Asp Val
            20                  25                  30

Ile Thr Ser Asn Asp Asp Glu Ile Gln Ser Val Ser Pro Gln Tyr Tyr
        35                  40                  45

Leu Arg Asp Met Phe Lys Ala Ser Ile Thr Glu Gly Pro Asp Asp Asp
    50                  55                  60

Phe Pro Pro Val Pro Glu Val Glu Asn Asp Ile Ile Leu Asp Asp Asp
65                  70                  75                  80

Glu Glu Tyr Asp Gly Tyr Lys Val Asp Phe Ala Glu Ala Arg Pro Trp
                85                  90                  95

Thr Ala Leu Thr Gln Lys Asn Ile Asp Gly Arg Met Asn Leu Glu Leu
            100                 105                 110

Met Ala Pro Glu Asn Leu Thr Asp Ala Gln Tyr Lys Gln Trp Val Glu
        115                 120                 125

Ser Val Ser Ser Ile Met Thr Ile Ser Arg Gln Ile Arg Leu His Gln
    130                 135                 140

Ala Glu Ile Met Asp Thr Ser Ser Gly Leu Leu Ile Glu Asn Met
145                 150                 155                 160

Ile Pro Ser Ile Gly Arg Thr Ser Glu Phe Lys Ser Ile Pro Glu His
                165                 170                 175

Ile Pro Pro Ser Pro Thr Ser Asp His Thr Thr Pro Pro Ser Ser Leu
            180                 185                 190

Arg Ser Asp Thr Pro Ser Gln Thr Ser Ser Ser Met Gly Leu Pro
        195                 200                 205

Asp Val Ser Ser Ala Ser Asp Trp Ser Gly Met Ile Asn Lys Lys Ile
    210                 215                 220

Arg Ile Pro Pro Val Val Ser Ser Lys Ser Pro Tyr Glu Phe Thr Leu
225                 230                 235                 240

Ser Asp Leu Tyr Gly Ser Asn Gln Ala Ala Leu Asp Tyr Leu Ser Gly
                245                 250                 255

Ser Gly Met Asp Leu Arg Thr Ala Val Cys Ser Gly Leu Lys Gln Arg
            260                 265                 270

Gly Ile Tyr Asn Arg Ile Arg Ile Gln Tyr Lys Ile Thr Pro Glu Phe
        275                 280                 285

Val
```

<210> SEQ ID NO 4
<211> LENGTH: 226
<212> TYPE: PRT
<213> ORGANISM: Isfahan Virus

<400> SEQUENCE: 4

```
Met Lys Ser Leu Lys Arg Leu Ile Lys Ser Asn Lys Lys Lys Gly Asp
1               5                   10                  15

Lys Lys Asn Val Ser Phe Met Asp Trp Asp Glu Pro Pro Ser Tyr Ser
            20                  25                  30

Asp Ser Arg Tyr Gly Cys Tyr Pro Ser Ala Pro Leu Phe Gly Val Asp
        35                  40                  45

Glu Met Met Glu Thr Leu Pro Thr Leu Gly Ile Gln Ser Leu Lys Ile
    50                  55                  60
```

```
Gln Tyr Lys Cys Ser Leu Gln Val Arg Ala Glu Thr Pro Phe Thr Ser
 65                  70                  75                  80

Phe Asn Asp Ala Ala Arg Cys Ile Ser Leu Trp Glu Thr Asp Tyr Arg
                 85                  90                  95

Gly Tyr Ala Gly Lys Lys Pro Phe Tyr Arg Leu Leu Met Leu Ile Ala
            100                 105                 110

Thr Lys Lys Leu Arg Ala Ala Pro Met Ser Leu Met Asp Gly Asn Arg
        115                 120                 125

Pro Glu Tyr Ser Ser Met Ile Gln Gly Gln Ser Ile Val His His Ser
    130                 135                 140

Leu Gly Val Ile Pro Pro Met Met His Val Pro Glu Thr Phe Thr Arg
145                 150                 155                 160

Glu Trp Asn Leu Leu Thr Asn Lys Gly Met Ile Thr Ala Gln Ile Trp
                165                 170                 175

Leu Gly Ile Thr Asp Val Val Asp Asp Leu Asn Pro Leu Ile Asn Pro
            180                 185                 190

Ala Leu Phe Ser Asp Glu Lys Glu Met Thr Leu Thr Ser Gln Met Phe
        195                 200                 205

Gly Leu Glu Leu Lys Lys Arg Asn Asp Asn Thr Trp Leu Ile Ser Lys
    210                 215                 220

Ser Tyr
225

<210> SEQ ID NO 5
<211> LENGTH: 523
<212> TYPE: PRT
<213> ORGANISM: Isfahan Virus

<400> SEQUENCE: 5

Met Thr Ser Val Leu Phe Met Val Gly Val Leu Leu Gly Ala Phe Gly
  1               5                  10                  15

Ser Thr His Cys Ser Ile Gln Ile Val Phe Pro Ser Glu Thr Lys Leu
                 20                  25                  30

Val Trp Lys Pro Val Leu Lys Gly Thr Arg Tyr Cys Pro Gln Ser Ala
            35                  40                  45

Glu Leu Asn Leu Glu Pro Asp Leu Lys Thr Met Ala Phe Asp Ser Lys
 50                  55                  60

Val Pro Ile Gly Ile Thr Pro Ser Asn Ser Asp Gly Tyr Leu Cys His
 65                  70                  75                  80

Ala Ala Lys Trp Val Thr Thr Cys Asp Phe Arg Trp Tyr Gly Pro Lys
                 85                  90                  95

Tyr Ile Thr His Ser Val His Ser Leu Arg Pro Thr Val Ser Asp Cys
            100                 105                 110

Lys Ala Ala Val Glu Ala Tyr Asn Ala Gly Thr Leu Met Tyr Pro Gly
        115                 120                 125

Phe Pro Pro Glu Ser Cys Gly Tyr Ala Ser Ile Thr Asp Ser Glu Phe
    130                 135                 140

Tyr Val Met Leu Val Thr Pro His Pro Val Gly Val Asp Asp Tyr Arg
145                 150                 155                 160

Gly His Trp Val Asp Pro Leu Phe Pro Thr Ser Glu Cys Asn Ser Asn
                165                 170                 175

Phe Cys Glu Thr Val His Asn Ala Thr Met Trp Ile Pro Lys Asp Leu
            180                 185                 190

Lys Thr His Asp Val Cys Ser Gln Asp Phe Gln Thr Ile Arg Val Ser
        195                 200                 205
```

```
Val Met Tyr Pro Gln Thr Lys Pro Thr Lys Gly Ala Asp Leu Thr Leu
    210                 215                 220

Lys Ser Lys Phe His Ala His Met Lys Gly Asp Arg Val Cys Lys Met
225                 230                 235                 240

Lys Phe Cys Asn Lys Asn Gly Leu Arg Leu Gly Asn Gly Glu Trp Ile
                245                 250                 255

Glu Val Gly Asp Glu Val Met Leu Asp Asn Ser Lys Leu Leu Ser Leu
                260                 265                 270

Phe Pro Asp Cys Leu Val Gly Ser Val Lys Ser Thr Leu Leu Ser
            275                 280                 285

Glu Gly Val Gln Thr Ala Leu Trp Glu Thr Asp Arg Leu Leu Asp Tyr
    290                 295                 300

Ser Leu Cys Gln Asn Thr Trp Glu Lys Ile Asp Arg Lys Glu Pro Leu
305                 310                 315                 320

Ser Ala Val Asp Leu Ser Tyr Leu Ala Pro Arg Ser Pro Gly Lys Gly
                325                 330                 335

Met Ala Tyr Ile Val Ala Asn Gly Ser Leu Met Ser Ala Pro Ala Arg
                340                 345                 350

Tyr Ile Arg Val Trp Ile Asp Ser Pro Ile Leu Lys Glu Ile Lys Gly
                355                 360                 365

Lys Lys Glu Ser Ala Ser Gly Ile Asp Thr Val Leu Trp Glu Gln Trp
370                 375                 380

Leu Pro Phe Asn Gly Met Glu Leu Gly Pro Asn Gly Leu Ile Lys Thr
385                 390                 395                 400

Lys Ser Gly Tyr Lys Phe Pro Leu Tyr Leu Gly Met Gly Ile Val
                405                 410                 415

Asp Gln Asp Leu Gln Glu Leu Ser Ser Val Asn Pro Val Asp His Pro
                420                 425                 430

His Val Pro Ile Ala Gln Ala Phe Ser Glu Gly Glu Val Phe
            435                 440                 445

Phe Gly Asp Thr Gly Val Ser Lys Asn Pro Ile Glu Leu Ile Ser Gly
    450                 455                 460

Trp Phe Ser Asp Trp Lys Glu Thr Ala Ala Leu Gly Phe Ala Ala
465                 470                 475                 480

Ile Ser Val Ile Leu Ile Ile Gly Leu Met Arg Leu Pro Leu Leu
                485                 490                 495

Cys Arg Arg Arg Lys Gln Lys Lys Val Ile Tyr Lys Asp Val Glu Leu
                500                 505                 510

Asn Ser Phe Asp Pro Arg Gln Ala Phe His Arg
                515                 520

<210> SEQ ID NO 6
<211> LENGTH: 2093
<212> TYPE: PRT
<213> ORGANISM: Isfahan Virus

<400> SEQUENCE: 6

Met Asp Glu Tyr Ser Glu Glu Lys Trp Gly Asp Ser Asp Glu Ser
1               5                   10                  15

Phe Gly Thr Gly Lys Tyr Ser Asp Glu Ser Arg Ile Arg Gly Leu Asn
                20                  25                  30

Ser Val Asp Tyr Asn Leu Asn Ser Pro Leu Ile Gln Asp Asp Leu Tyr
                35                  40                  45

Tyr Leu Met Glu Arg Val Arg Gly Arg Pro Val Pro Pro Ile Trp Lys
```

```
            50                  55                  60
Ala Lys Asn Trp Thr Glu Thr Ile His Leu Val Gln Glu Ser Arg Leu
 65                  70                  75                  80

Asp Tyr Leu Pro Thr Gln Lys Leu His Ser Trp Tyr Ala Glu Trp Leu
                 85                  90                  95

Met Glu Glu Ser His Asp Ser Ser Gln Gly Leu Ala Phe Leu Lys Glu
            100                 105                 110

Val Asp Lys Asp Ser Leu Glu Thr Tyr Glu Val Val Met Ser Phe Leu
        115                 120                 125

Arg Gly Trp Cys Gly Gly Ala Pro Ala Tyr Lys Lys Lys Glu Gly Arg
    130                 135                 140

His Ile Ala Lys Ile Gly Ser Leu Cys Gln Lys Phe Leu Asp Leu His
145                 150                 155                 160

Arg Val Ile Leu Ile Met Asn Ala Ser Thr Gln Met Glu Leu Ser Asn
                165                 170                 175

Leu Ala Glu Thr Phe Gln Ala Ser Ser Val Ser Lys Lys Ile Ile Thr
            180                 185                 190

Thr Pro Ser Met Gly Lys Met Glu Met Ser Gly Gln Phe Ala Leu Ala
        195                 200                 205

Tyr Gln Gln Lys Val Ile Leu Asp Arg Asn Phe Leu Leu Met Met Lys
    210                 215                 220

Asp Val Val Ile Gly Arg Met Gln Thr Leu Leu Ser Met Val Ser Arg
225                 230                 235                 240

Thr Asp Asp Lys Phe Ser Asp Gly Asp Ile Ser Tyr Leu Ile Lys Ile
                245                 250                 255

Tyr Gln Leu Gly Asp Lys Ile Ile Gln Ser Leu Gly Asn Asp Gly Tyr
            260                 265                 270

Glu Leu Ile Lys Thr Ile Glu Pro Met Cys Asn Leu Arg Leu Ser Asp
        275                 280                 285

Leu Ala Arg Glu Tyr Arg Pro Leu Ile Pro Glu Phe Pro His Phe Arg
    290                 295                 300

Gln His Ile Glu Gly Thr Val Ser Glu Leu Arg Lys Lys Thr Ala Leu
305                 310                 315                 320

Ile Val Asp Met Phe Lys Met Ile Asp Arg Thr Pro Gly Val Asp Ile
                325                 330                 335

Thr Leu Val Ile Tyr Gly Ser Phe Arg His Trp Gly His Pro Phe Ile
            340                 345                 350

Asp Tyr Phe Ala Gly Leu Thr Lys Leu Asn Ser Gln Val Thr Met Gly
        355                 360                 365

Lys Gln Ile Asp Asp Glu Tyr Val Ala Cys Leu Ala Ser Asp Leu Ala
    370                 375                 380

Arg Ile Val Leu Thr Lys Glu Phe Asn Glu Lys Lys Arg Trp Ser Val
385                 390                 395                 400

Asn Tyr Asn Leu Val Pro Gln Asp His Pro Phe His Glu His Ile Arg
                405                 410                 415

Asp Asn Thr Trp Pro Thr Pro Ala Val Ile Gln Asp Phe Gly Asp Lys
            420                 425                 430

Trp His Glu Leu Pro Leu Thr Gln Cys Phe Glu Ile Pro Asp Leu Ile
        435                 440                 445

Asp Pro Ser Ile Ile Tyr Ser Asp Lys Ser His Ser Met Asn Arg Gln
    450                 455                 460

Asp Val Leu Asn His Val Lys Arg Lys Pro Asp Gln Pro Ile Pro Ser
465                 470                 475                 480
```

```
Arg Lys Val Leu Gln Thr Met Ile Asp Thr Pro Ala Thr Asn Trp Leu
                485                 490                 495

Glu Phe Leu Glu Glu Ile Asp Lys Asn Gly Leu Ser Asp Asp Leu
        500                 505                 510

Val Ile Gly Leu Lys Gly Lys Glu Arg Glu Leu Lys Ile Ala Gly Arg
            515                 520                 525

Phe Phe Ser Leu Met Ser Trp Lys Leu Arg Glu Tyr Phe Val Ile Thr
530                 535                 540

Glu Tyr Leu Ile Lys Thr His Phe Val Pro Leu Phe His Gly Leu Thr
545                 550                 555                 560

Met Ala Asp Asp Met Thr Ala Val Ile Lys Lys Met Leu Glu Ser Ser
                565                 570                 575

Ser Gly Gln Gly Leu Lys Asp Tyr Ser Ala Val Cys Ile Ala Asn His
            580                 585                 590

Ile Asp Tyr Glu Lys Trp Asn Asn His Gln Arg Lys Arg Ser Asn Glu
        595                 600                 605

Pro Ile Phe Lys Val Met Gly Gln Phe Leu Gly Phe Pro Asn Leu Ile
    610                 615                 620

Ser Arg Thr His Glu Phe Phe Glu Lys Ser Leu Ile Tyr Tyr Asn Gly
625                 630                 635                 640

Arg Pro Asp Leu Met Lys Val Gln Asp Gly Arg Leu Val Asn Thr Thr
                645                 650                 655

Lys Gln Leu Val Cys Trp Glu Gly Gln Ala Gly Gly Leu Glu Gly Leu
            660                 665                 670

Arg Gln Lys Gly Trp Ser Ile Leu Asn Leu Leu Val Ile Gln Arg Glu
        675                 680                 685

Ser Lys Ile Arg Asn Thr Ala Val Lys Val Leu Ala Gln Gly Asp Asn
    690                 695                 700

Gln Val Ile Cys Thr Gln Tyr Lys Thr Lys Gln His Arg Asn Glu Thr
705                 710                 715                 720

Glu Leu Arg Ser Ala Leu Thr Gln Met Lys Leu Asn Asn Asp Ala Val
                725                 730                 735

Met Lys Ala Ile Glu Ser Gly Thr Asn Lys Leu Gly Leu Leu Ile Asn
            740                 745                 750

Gln Asp Glu Thr Met Gln Ser Ala Asp Tyr Leu Asn Tyr Gly Lys Val
        755                 760                 765

Pro Ile Phe Arg Gly Val Ile Arg Gly Leu Glu Thr Lys Arg Trp Ser
    770                 775                 780

Arg Val Thr Cys Val Thr Asn Asp Gln Leu Pro Thr Cys Ala Asn Leu
785                 790                 795                 800

Met Ser Ser Val Ser Thr Asn Ala Leu Thr Val Ala His Phe Asp Val
                805                 810                 815

Thr Pro Leu Asn Ala Met Ile Gln Tyr Asn Tyr Phe Gly Asn Phe Ser
            820                 825                 830

Arg Leu Leu Leu Asn Met His Asp Pro Ala Val Arg Cys Ser Leu Phe
        835                 840                 845

Gln Leu Ser Gln Lys His Lys Ile Asp Leu Phe Ser Phe Glu Phe Lys
    850                 855                 860

Val Gly Val Leu Tyr Leu Asp Pro Ser Ile Gly Gly Val Cys Gly Thr
865                 870                 875                 880

Ala Leu Ser Arg Phe Leu Ile Arg Gly Phe Pro Asp Pro Val Thr Glu
                885                 890                 895
```

-continued

Ser Ile Ser Phe Trp Lys Val Ile Tyr Asn Asn Thr Gln Asp Asn Arg
              900                 905                 910

Leu Lys Lys Leu Cys Thr Ala Phe Gly Asn Pro Lys Ile Ala Gln Phe
        915                 920                 925

Arg Tyr Ser His Ile Glu Lys Leu Leu Glu Asp Pro Thr Ser Leu Asn
    930                 935                 940

Ile Ser Met Gly Met Ser Ala Ala Asn Leu Leu Lys Ser Glu Ile Lys
945                 950                 955                 960

Lys Asn Leu Leu Arg Lys Arg Arg Thr Ile Gly Asn Ser Ile Val Arg
                965                 970                 975

Asp Ala Val Thr Tyr Ile His Ser Glu Asp Glu Lys Ile Arg Ser Tyr
            980                 985                 990

Leu Trp Ser Ile Asn Pro Leu Phe Pro Arg Phe Leu Ser Glu Phe Lys
        995                 1000                1005

Ser Gly Thr Phe Met Gly Val Ala Ser Ser Val Val Ser Leu Phe
    1010                1015                1020

Gln Asn Ser Arg Thr Ile Arg Asn Val Phe Lys Asp Tyr Met Ser
    1025                1030                1035

Ser Ala Ile Asp Glu Leu Ile Thr Lys Ser Glu Val Asn Ser Leu
    1040                1045                1050

Glu His Leu Cys Lys Tyr Lys Gly Val Arg Asn Phe Asp Gln Val
    1055                1060                1065

Trp Lys Cys Ser Ala Ser Gln Ala Asp Tyr Leu Arg Arg Leu Ser
    1070                1075                1080

Trp Gly Arg Lys Val Leu Gly Thr Thr Ile Pro His Pro Leu Glu
    1085                1090                1095

Met Leu Gly Ala Gly Thr Ile Lys Asn Asn Ser Ser Thr Cys Cys
    1100                1105                1110

Glu His Ser Gly Gln Asp Tyr Ile Ser Val Phe Cys Pro Lys Gly
    1115                1120                1125

Ile Ser Asn Val Leu Ile Glu Arg Gly Pro Met Ala Ala Tyr Leu
    1130                1135                1140

Gly Ser Lys Thr Ser Glu Ser Thr Ser Ile Leu Gln Pro Trp Glu
    1145                1150                1155

Lys Glu Ser Lys Ile Pro Ile Ile Lys Arg Ala Thr Arg Leu Arg
    1160                1165                1170

Asp Ala Ile His Trp Phe Val Glu Pro Ser Ser Asn Leu Ala Lys
    1175                1180                1185

Ser Ile Leu Gln Asn Ile Thr Ala Leu Thr Gly Glu Glu Trp Gly
    1190                1195                1200

Ser Ser Leu Glu Gly Phe Lys Arg Thr Gly Ser Ala Leu His Arg
    1205                1210                1215

Phe Thr Thr Ser Arg Met Ser His Gly Gly Phe Cys Ala Gln Ser
    1220                1225                1230

Pro Ala Ala Leu Thr Arg Met Met Ala Thr Thr Asp Thr Met Ser
    1235                1240                1245

Asp Tyr Ala Lys Asp Asn Tyr Asp Phe Met Phe Gln Ala Cys Leu
    1250                1255                1260

Leu Phe Ser Gln Ile Thr Thr Ser Val Leu Leu Leu Glu Thr Thr
    1265                1270                1275

Ile Ser Asn Thr Val His Phe His Thr Arg Cys Ile Asn Cys Val
    1280                1285                1290

Arg Lys Ile Glu Glu Pro Trp Leu Glu Ser Pro Ser Val Leu Gln

-continued

```
            1295                1300                1305
Ser Lys Asp Val Ser Asn Val Leu Ala Ser Trp Arg Asn Gly Gly
    1310                1315                1320
Gly Ser Trp Gly Glu Gln Leu His Gln Leu Lys Pro Leu Lys Gly
    1325                1330                1335
Asp Trp Glu Ile Leu Thr Pro Ala Glu Lys Ser Tyr His Val Gly
    1340                1345                1350
Arg Thr Leu Gly Phe Leu Phe Gly Asp Leu Thr Gly Gln Ser Ser
    1355                1360                1365
Ile Arg Ala Asp Asp Ser Ser Leu Phe Pro Leu Ser Ile Gln Lys
    1370                1375                1380
Arg Leu Arg Gly Arg Gly Phe Leu Arg Gly Val Leu Asp Gly Leu
    1385                1390                1395
Val Arg Ala Ser Ala Cys Gln Val Ile His Arg Arg Ser Leu Thr
    1400                1405                1410
Gln Leu Lys Arg Pro Ala Asn Ala Val Tyr Gly Gly Leu Ile Phe
    1415                1420                1425
Leu Ile Asp Lys Ile Ser Ala Ser Ser Thr Phe Ile Asn Leu Cys
    1430                1435                1440
Arg Asp Gly Pro Ile Arg Glu Glu Leu Ser Ser Ile Pro His Lys
    1445                1450                1455
Ile Pro Thr Ser Tyr Pro Thr Ser Asn Ala Asp Leu Gly Leu His
    1460                1465                1470
Ile Arg Asn Tyr Phe Lys Phe Gln Cys Lys Ser Val Glu Leu Gly
    1475                1480                1485
Lys Tyr Gln Ser Asp Leu Glu Asp Leu Trp Leu Phe Ser Asp Leu
    1490                1495                1500
Leu Ser Ser Gly Phe Ala Gly Pro Tyr Ala Leu Ser Ser Lys Val
    1505                1510                1515
Leu Lys Ser Leu Tyr Lys Pro Ser Leu Ser Arg Arg Asp Arg Asn
    1520                1525                1530
Asn Ile Arg Lys Leu Gly Ala Leu Ser Arg Leu Leu Arg Ser His
    1535                1540                1545
Glu Asn Trp Ser Glu Leu His Lys Glu Phe Leu Thr Ser Gln Leu
    1550                1555                1560
Leu Leu Cys Gln Glu Glu Val Arg His Ala Cys Lys Phe Gly Ile
    1565                1570                1575
Pro Lys Asn Val Ser Ala Lys Ser Ser Met Val Trp Gly Lys Glu
    1580                1585                1590
Ala Val Ser Tyr Val Leu Asp Ile Pro Val Glu Phe Thr Ser Gln
    1595                1600                1605
Lys Gln Thr Lys His Leu Asn Ala Cys Pro Arg Ile Gln Asp Pro
    1610                1615                1620
Thr Ile Ser Gly Leu Arg Leu Gly Gln Leu Pro Thr Gly Ala His
    1625                1630                1635
Tyr Lys Ile Arg Thr Ile Leu Asn Ala Tyr Asn Ile Lys Cys Arg
    1640                1645                1650
Asp Val Leu Cys Gly Gly Asp Gly Ser Gly Gly Met Thr Ala Ala
    1655                1660                1665
Cys Leu Arg Tyr Tyr Ser Asn Ser Arg Ala Ile Phe Asn Ser Ile
    1670                1675                1680
Leu Glu Phe Asp Gly Ser Ser Met Lys Gly Ser Ser Pro Asp Pro
    1685                1690                1695
```

```
Pro Ser Ala Leu Glu Thr Val Asp Gln Gly Met Val Arg Cys Val
    1700                1705                1710

Asn Ala Thr Thr Cys Trp Glu Asn Pro Ser Asp Leu Ser Gln Glu
    1715                1720                1725

Arg Thr Trp Asp Tyr Phe Leu His Leu Lys Lys Ser Phe Asn Met
    1730                1735                1740

Lys Ile Asp Leu Ile Ile Leu Asp Met Glu Val Arg Asp Phe Gln
    1745                1750                1755

Ile Ser Lys Leu Ile Glu Gly Asn Leu Arg Leu Lys Ile Ser Lys
    1760                1765                1770

Leu Leu Glu Lys Asn Gly Thr Leu Ile Tyr Lys Thr Tyr Gly Thr
    1775                1780                1785

Ile Ile Cys Ser Glu Thr Ser Asn Val Leu Thr Thr Leu Gly Pro
    1790                1795                1800

Leu Phe His Ser Val Tyr Ile Val Gln Thr Gly Tyr Ser Ser Ser
    1805                1810                1815

Phe Thr Ser Glu Val Tyr Val Leu Phe Ser Lys Gln Lys Ser Phe
    1820                1825                1830

Val Asp Ser Pro Tyr Val Asp Trp Gly Ser Leu Gln Tyr Asn Trp
    1835                1840                1845

Glu Lys Leu Ala Cys Phe Arg Asn Pro Arg Gln Glu Phe Lys Arg
    1850                1855                1860

Ala Leu Arg Ile Arg Ser Ser Arg Ser Leu Met Gly Ile Pro Ser
    1865                1870                1875

Ser Phe Leu Pro Asp Pro Leu Val Asn Leu Glu Thr Leu Leu Gln
    1880                1885                1890

Ile Ser Gly Val Pro Ser Gly Val Ser His Gln Leu Val Thr Asp
    1895                1900                1905

Val Lys Ser Ser Gly Ala Ser Gly Leu Ser Ser Ala Ile Gly Leu
    1910                1915                1920

Leu Gly Leu Ile Ser His Phe Thr Leu Asp Val Thr Lys Leu Tyr
    1925                1930                1935

Val Gln Glu Tyr Arg Pro Pro Ser Asp Asn Arg Leu Ile Lys Met
    1940                1945                1950

Ala Ser Ala Ile Thr Gly Ile Ser Tyr Trp Ile Ser Ile Ala Tyr
    1955                1960                1965

His Asp Gln Gln Leu Asn Gln Ala Leu Thr Ser Val Ile Lys Lys
    1970                1975                1980

Ser Phe Pro Ile Arg Trp Gly Leu Ile Asn His Arg Leu His Trp
    1985                1990                1995

Ser Val Ser Asp Arg Phe His Arg Ser Lys Asp Val Arg Leu Ser
    2000                2005                2010

Asp Cys Leu Ala Gly Ile Gly Asn Trp Ile Arg Gly Met Glu Leu
    2015                2020                2025

Met Lys Leu Pro Ala Gly Met Phe Ser His Lys Glu Val Asn Met
    2030                2035                2040

Ile Leu Ser Lys Tyr Ile Arg Gly Leu Asn Tyr His Thr Ile Ser
    2045                2050                2055

Ser Arg Thr Gly Ile Leu Glu Ile Leu Lys Ser Gln Phe Ser Ile
    2060                2065                2070

Ile Asp Arg Ser Leu Met Thr Ile Thr Thr Asp Asn Ile Gln Ser
    2075                2080                2085
```

Ser Asp Trp Thr Asp
    2090

<210> SEQ ID NO 7
<211> LENGTH: 11161
<212> TYPE: DNA
<213> ORGANISM: Vesicular stomatitis virus

<400> SEQUENCE: 7

| | | | | | |
|---|---|---|---|---|---|
| acgaagacaa | acaaaccatt | attatcatta | aaaggctcag | gagaaacttt | aacagtaatc | 60 |
| aaaatgtctg | ttacagtcaa | gagaatcatt | gacaacacag | tcatagttcc | aaaacttcct | 120 |
| gcaaatgagg | atccagtgga | atacccggca | gattacttca | gaaaatcaaa | ggagattcct | 180 |
| ctttacatca | atactacaaa | aagtttgtca | gatctaagag | gatatgtcta | ccaaggcctc | 240 |
| aaatccggaa | atgtatcaat | catacatgtc | aacagctact | tgtatggagc | attaaaggac | 300 |
| atccggggta | agttggataa | agattggtca | agtttcggaa | taaacatcgg | gaaagcaggg | 360 |
| gatacaatcg | gaatatttga | ccttgtatcc | ttgaaagccc | tggacggcgt | acttccagat | 420 |
| ggagtatcgg | atgcttccag | aaccagcgca | gatgacaaat | ggttgccttt | gtatctactt | 480 |
| ggcttataca | gagtgggcag | aacacaaatg | cctgaataca | gaaaaaagct | catggatggg | 540 |
| ctgacaaatc | aatgcaaaat | gatcaatgaa | cagtttgaac | ctcttgtgcc | agaaggtcgt | 600 |
| gacattttg | atgtgtgggg | aaatgacagt | aattacacaa | aaattgtcgc | tgcagtggac | 660 |
| atgttcttcc | acatgttcaa | aaaacatgaa | tgtgcctcgt | tcagatacgg | aactattgtt | 720 |
| tccagattca | aagattgtgc | tgcattggca | catttggac | acctctgcaa | ataaccgga | 780 |
| atgtctacag | aagatgtaac | gacctggatc | ttgaaccgag | aagttgcaga | tgaaatggtc | 840 |
| caaatgatgc | ttccaggcca | agaaattgac | aaggccgatt | catacatgcc | ttatttgatc | 900 |
| gactttggat | tgtcttctaa | gtctccatat | tcttccgtca | aaaccctgc | cttccacttc | 960 |
| tgggggcaat | tgacagctct | tctgctcaga | tccaccagag | caaggaatgc | ccgacagcct | 1020 |
| gatgacattg | agtatacatc | tcttactaca | gcaggtttgt | tgtacgctta | tgcagtagga | 1080 |
| tcctctgccg | acttggcaca | acagtttttgt | gttggagata | caaatacac | tccagatgat | 1140 |
| agtaccggag | gattgacgac | taatgcaccg | ccacaaggca | gagatgtggt | cgaatggctc | 1200 |
| ggatggtttg | aagatcaaaa | cagaaaaccg | actcctgata | tgatgcagta | tgcgaaaaga | 1260 |
| gcagtcatgt | cactgcaagg | cctaagagag | aagacaattg | gcaagtatgc | taagtcagaa | 1320 |
| tttgacaaat | gaccctataa | ttctcagatc | acctattata | tattatgcta | catatgaaaa | 1380 |
| aaactaacag | atatcatgga | taatctcaca | aaagttcgtg | agtatctcaa | gtcctattct | 1440 |
| cgtctggatc | aggcggtagg | agagatagat | gagatcgaag | cacaacgagc | tgaaaagtcc | 1500 |
| aattatgagt | tgttccaaga | ggatggagtg | aagagcata | ctaagcctc | ttattttcag | 1560 |
| gcagcagatg | attctgacac | agaatctgaa | ccagaaattg | aagacaatca | aggtttgtat | 1620 |
| gcacaggatc | cagaagctga | gcaagttgaa | ggctttatac | aggggccttt | agatgactat | 1680 |
| gcagatgagg | aagtggatgt | tgtatttact | tcggactgga | aaccacctga | gcttgaatct | 1740 |
| gacgagcatg | gaaagaccct | tacggttgaca | tcgccagagg | gtttaagtgg | agagcagaaa | 1800 |
| tcccagtggc | tttcgacgat | taagcagtc | gtgcaaagtg | ccaaatactg | gaatctggca | 1860 |
| gagtgcacat | ttgaagcatc | gggagaaggg | gtcattatga | aggagcgcca | gataactccg | 1920 |
| gatgtatata | aggtcactcc | agtgatgaac | acacatccgt | cccaatcaga | agcagtatca | 1980 |
| gatgtttggt | ctctctcaaa | gacatccatg | actttccaac | ccaagaaagc | aagtcttcag | 2040 |

```
cctctcacca tatccttgga tgaattgttc tcatctagag gagagttcat ctctgtcgga    2100
ggtgacggac gaatgtctca taaagaggcc atcctgctcg gcctgagata caaaaagttg    2160
tacaatcagg cgagagtcaa atattctctg tagactatga aaaaagtaa cagatatcac     2220 gatctaagtg ttatcccaat ccattcatca tgagttcctt aaagaagatt ctcggtctga    2280
aggggaaagg taagaaatct aagaaattag ggatcgcacc acccccttat gaagaggaca    2340
ctagcatgga gtatgctccg agcgctccaa ttgacaaatc ctattttgga gttgacgaga    2400
tggacaccta tgatccgaat caattaagat atgagaaatt cttctttaca gtgaaaatga    2460
cggttagatc taatcgtccg ttcagaacat actcagatgt ggcagccgct gtatcccatt    2520
gggatcacat gtacatcgga atggcaggga acgtcccctt ctacaaaatc ttggcttttt    2580
tgggttcttc taatctaaag gccactccag cggtattggc agatcaaggt caaccagagt    2640
atcacactca ctgcgaaggc agggcttatt tgccacatag gatggggaag accccctccca   2700 tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctaac ttctagcttc tgaacaatcc ccggtttact cagtctctcc taattccagc    3000
ctctcgaaca actaatatcc tgtcttttct atccctatga aaaaactaa cagagatcga    3060 tctgtttcct tgacactatg aagtgccttt tgtacttagc cttttttattc attggggtga   3120 attgcaagtt caccatagtt tttccacaca accaaaaagg aaactggaaa aatgttcctt    3180
ctaattacca ttattgcccg tcaagctcag atttaaattg cataatgac ttaataggca     3240 cagccataca agtcaaaatg cccaagagtc acaaggctat tcaagcagac ggttggatgt    3300
gtcatgcttc caaatgggtc actacttgtg atttccgctg gtatggaccg aagtatataa    3360
cacagtccat ccgatccttc actccatctg tagaacaatg caaggaaagc attgaacaaa    3420
cgaaacaagg aacttggctg aatccaggct tccctcctca aagttgtgga tatgcaactg    3480
tgacggatgc cgaagcagtg attgtccagg tgactcctca ccatgtgctg gttgatgaat    3540
acacaggaga atgggttgat tcacagttca tcaacggaaa atgcagcaat tacatatgcc    3600
ccactgtcca taactctaca acctggcatt ctgactataa ggtcaaaggg ctatgtgatt    3660
ctaacctcat ttccatggac atcaccttct tctcagagga cggagagcta tcatccctgg    3720
gaaaggaggg cacagggttc agaagtaact actttgctta tgaaactgga ggcaaggcct    3780
gcaaaatgca atactgcaag cattggggag tcagactccc atcaggtgtc tggttcgaga    3840
tggctgataa ggatctcttt gctgcagcca gattccctga atgcccagaa gggtcaagta    3900
tctctgctcc atctcagacc tcagtggatg taagtctaat tcaggacgtt gagaggatct    3960
tggattattc cctctgccaa gaaacctgga gcaaaatcag agcgggtctt ccaatctctc    4020
cagtggatct cagctatctt gctcctaaaa acccaggaac cggtcctgct ttcaccataa    4080
tcaatggtac cctaaaatac tttgagacca gatacatcag agtcgatatt gctgctccaa    4140
tcctctcaag aatggtcgga atgatcagtg gaactaccac agaaagggaa ctgtgggatg    4200
actgggcacc atatgaagac gtggaaattg gacccaatgg agttctgagg accagttcag    4260
gatataagtt ccctttatac atgattggac atggtatgtt ggactccgat cttcatctta    4320
gctcaaaggc tcaggtgttc gaacatcctc acattcaaga cgctgcttcg caacttcctg    4380
atgatgagag tttatttttt ggtgatactg ggctatccaa aaatccaatc gagcttgtag    4440
```

```
aaggttggtt cagtagttgg aaaagctcta ttgcctcttt tttctttatc atagggttaa   4500
tcattggact attcttggtt ctccgagttg gtatccatct ttgcattaaa ttaaagcaca   4560
ccaagaaaag acagatttat acagacatag agatgaaccg acttggaaag taactcaaat   4620
cctgcacaac agattcttca tgtttggacc aaatcaactt gtgataccat gctcaaagag   4680
gcctcaatta tatttgagtt tttaatttt atgaaaaaaa ctaacagcaa tcatggaagt   4740
ccacgatttt gagaccgacg agttcaatga tttcaatgaa gatgactatg ccacaagaga   4800
attcctgaat cccgatgagc gcatgacgta cttgaatcat gctgattaca atttgaattc   4860
tcctctaatt agtgatgata ttgacaattt gatcaggaaa ttcaattctc ttccgattcc   4920
ctcgatgtgg gatagtaaga actgggatgg agttcttgag atgttaacat catgtcaagc   4980
caatcccatc tcaacatctc agatgcataa atggatggga agttggttaa tgtctgataa   5040
tcatgatgcc agtcaagggt atagttttt acatgaagtg gacaaagagg cagaaataac   5100
atttgacgtg gtggagacct tcatccgcgg ctggggcaac aaaccaattg aatacatcaa   5160
aaaggaaaga tggactgact cattcaaaat tctcgcttat ttgtgtcaaa agttttgga   5220 cttacacaag ttgacattaa tcttaaatgc tgtctctgag gtggaattgc tcaacttggc   5280
gaggactttc aaaggcaaag tcagaagaag ttctcatgga acgaacatat gcaggattag   5340
ggttcccagc ttgggtccta cttttatttc agaaggatgg gcttacttca agaaacttga   5400
tattctaatg gaccgaaact ttctgttaat ggtcaaagat gtgattatag ggaggatgca   5460
aacggtgcta tccatggtat gtagaataga caacctgttc tcagagcaag acatcttctc   5520
ccttctaaat atctacagaa ttggagataa aattgtggag aggcagggaa attttttctta   5580 tgacttgatt aaaatggtgg aaccgatatg caacttgaag ctgatgaaat tagcaagaga   5640
atcaaggcct ttagtcccac aattccctca ttttgaaaat catatcaaga cttctgttga   5700
tgaaggggca aaaattgacc gaggtataag attcctccat gatcagataa tgagtgtgaa   5760
aacagtggat ctcacactgg tgatttatgg atcgttcaga cattggggtc atccttttat   5820
agattattac actggactag aaaaattaca ttcccaagta accatgaaga agatattga   5880 tgtgtcatat gcaaaagcac ttgcaagtga tttagctcgg attgttctat ttcaacagtt   5940
caatgatcat aaaaagtggt tcgtgaatgg agacttgctc cctcatgatc atccctttaa   6000
aagtcatgtt aaagaaaata catggcccac agctgctcaa gttcaagatt ttggagataa   6060
atggcatgaa cttccgctga ttaaatgttt tgaaataccc gacttactag acccatcgat   6120
aatatactct gacaaaagtc attcaatgaa taggtcagag gtgttgaaac atgtccgaat   6180
gaatccgaac actcctatcc ctagtaaaaa ggtgttgcag actatgttgg acacaaaggc   6240
taccaattgg aaagaatttc ttaaagagat tgatgagaag ggcttagatg atgatgatct   6300
aattattggt cttaaaggaa aggagaggga actgaagttg gcaggtagat ttttctccct   6360
aatgtcttgg aaattgcgag aatactttgt aattaccgaa tatttgataa agactcattt   6420
cgtccctatg tttaaaggcc tgacaatggc ggacgatcta actgcagtca ttaaaaagat   6480
gttagattcc tcatccggcc aaggattgaa gtcatatgag gcaatttgca tagccaatca   6540
cattgattac gaaaaatgga ataaccacca aggaagtta tcaaacggcc cagtgttccg   6600
agttatgggc cagttcttag gttatccatc cttaatcgag agaactcatg aattttttga   6660
gaaaagtctt atatactaca atggaagacc agacttgatg cgtgttcaca acaacacact   6720
gatcaattca acctcccaac gagtttgttg gcaaggacaa gagggtggac tggaaggtct   6780
```

```
acggcaaaaa ggatggacta tcctcaatct actggttatt caaagagagg ctaaaatcag    6840
aaacactgct gtcaaagtct tggcacaagg tgataatcaa gttatttgca cacagtataa    6900
aacgaagaaa tcgagaaacg ttgtagaatt acagggtgct ctcaatcaaa tggtttctaa    6960
taatgagaaa attatgactg caatcaaaat agggacaggg aagttaggac ttttgataaa    7020
tgacgatgag actatgcaat ctgcagatta cttgaattat ggaaaaatac cgattttccg    7080
tggagtgatt agagggttag agaccaagag atggtcacga gtgacttgtg tcaccaatga    7140
ccaaataccc acttgtgcta atataatgag ctcagtttcc acaaatgctc tcaccgtagc    7200
tcattttgct gagaacccaa tcaatgccat gatacagtac aattattttg gacatttgc    7260 tagactcttg ttgatgatgc atgatcctgc tcttcgtcaa tcattgtatg aagttcaaga    7320
taagataccg ggcttgcaca gttctacttt caaatacgcc atgttgtatt ggacccttc    7380 cattggagga gtgtcgggca tgtctttgtc caggtttttg attagagcct tcccagatcc    7440
cgtaacagaa agtctctcat tctggagatt catccatgta catgctcgaa gtgagcatct    7500
gaaggagatg agtgcagtat ttggaaaccc cgagatagcc aagtttcgaa taactcacat    7560
agacaagcta gtagaagatc caacctctct gaacatcgct atgggaatga gtccagcgaa    7620
cttgttaaag actgaggtta aaaaatgctt aatcgaatca agacaaacca tcaggaacca    7680
ggtgattaag gatgcaacca tatttgta tcatgaagag gatcggctca gaagtttctt    7740
atggtcaata aatcctctgt tccctagatt tttaagtgaa ttcaaatcag gcactttttt    7800
gggagtcgca gacgggctca tcagtctatt tcaaaattct cgtactattc ggaactcctt    7860
taagaaaaag tatcataggg aattggatga tttgattgtg aggagtgagg tatcctcttt    7920
gacacattta gggaaacttc atttgagaag gggatcatgt aaaatgtgga catgttcagc    7980
tactcatgct gacacattaa gatacaaatc ctggggccgt acagttattg gacaactgt    8040 accccatcca ttagaaatgt tgggtccaca acatcgaaaa gagactcctt gtgcaccatg    8100
taacacatca gggttcaatt atgtttctgt gcattgtcca gacgggatcc atgacgtctt    8160
tagttcacgg ggaccattgc ctgcttatct agggtctaaa acatctgaat ctacatctat    8220
tttgcagcct tgggaaaggg aaagcaaagt cccactgatt aaaagagcta cacgtcttag    8280
agatgctatc tcttggtttg ttgaacccga ctctaaaacta gcaatgacta ctttctaa    8340 catccactct ttaacaggcg aagaatggac caaaaggcag catgggttca aaagaacagg    8400
gtctgccctt cataggtttt cgacatctcg gatgagccat ggtgggttcg catctcagag    8460
cactgcagca ttgaccaggt tgatggcaac tacagacacc atgagggatc tgggagatca    8520
gaatttcgac tttttattcc aagcaacgtt gctctatgct caaattacca ccactgttgc    8580
aagagacgga tggatcacca gttgtacaga tcattatcat attgcctgta agtcctgttt    8640
gagacccata gaagagatca ccctggactc aagtatggac tacacgcccc cagatgtatc    8700
ccatgtgctg aagacatgga ggaatgggga aggttcgtgg ggacaagaga taaaacagat    8760 ctatcctta gaagggaatt ggaagaattt agcacctgct gagcaatcct atcaagtcgg    8820
cagatgtata ggttttctat atggagactt ggcgtataga aaatctactc atgccgagga    8880
cagttctcta tttcctctat ctatacaagg tcgtattaga ggtcgaggtt tcttaaaagg    8940
gttgctagac ggattaatga gagcaagttg ctgccaagta atacaccgga gaagtctggc    9000
tcatttgaag aggccggcca acgcagtgta cggaggtttg atttacttga ttgataaatt    9060
gagtgtatca cctccattcc tttctcttac tagatcagga cctattagag acgaattaga    9120
aacgattccc cacaagatcc caacctccta tccgacaagc aaccgtgata tgggggtgat    9180
```

| tgtcagaaat tacttcaaat accaatgccg tctaattgaa aagggaaaat acagatcaca | 9240 |
| ttattcacaa ttatggttat tctcagatgt cttatccata gacttcattg gaccattctc | 9300 |
| tatttccacc accctcttgc aaatcctata caagccattt ttatctggga aagataagaa | 9360 |
| tgagttgaga gagctggcaa atctttcttc attgctaaga tcaggagagg ggtgggaaga | 9420 |
| catacatgtg aaattcttca ccaaggacat attattgtgt ccagaggaaa tcagacatgc | 9480 |
| ttgcaagttc gggattgcta aggataataa taaagacatg agctatcccc cttggggaag | 9540 |
| ggaatccaga gggacaatta caacaatccc tgtttattat acgaccaccc cttacccaaa | 9600 |
| gatgctagag atgcctccaa gaatccaaaa tccctgctg tccggaatca ggttgggcca | 9660 |
| attccaact ggcgctcatt ataaaattcg gagtatatta catggaatgg gaatccatta | 9720 |
| cagggacttc ttgagttgtg gagacggctc cggaggggatg actgctgcat tactacgaga | 9780 |
| aaatgtgcat agcagaggaa tattcaatag tctgttagaa ttatcagggt cagtcatgcg | 9840 |
| aggcgcctct cctgagcccc ccagtgccct agaaacttta ggaggagata atcgagatg | 9900 |
| tgtaaatggt gaaacatgtt gggaatatcc atctgactta tgtgacccaa ggacttggga | 9960 |
| ctatttcctc cgactcaaag caggcttggg gcttcaaatt gatttaattg taatggatat | 10020 |
| ggaagttcgg gattcttcta ctagcctgaa aattgagacg aatgttagaa attatgtgca | 10080 |
| ccggattttg gatgagcaag gagttttaat ctacaagact tatggaacat atatttgtga | 10140 |
| gagcgaaaag aatgcagtaa caatccttgg tcccatgttc aagacggtcg acttagttca | 10200 |
| aacagaattt agtagttctc aaacgtctga agtatatatg gtatgtaaag gtttgaagaa | 10260 |
| attaatcgat gaacccaatc ccgattggtc ttccatcaat gaatcctgga aaaacctgta | 10320 |
| cgcattccag tcatcagaac aggaatttgc cagagcaaag aaggttagta catactttac | 10380 |
| cttgacaggt attccctccc aattcattcc tgatcctttt gtaaacattg agactatgct | 10440 |
| acaaatattc ggagtaccca cgggtgtgtc tcatgcggct gccttaaaat catctgatag | 10500 |
| acctgcagat ttattgacca ttagccttt ttatatggcg attatatcgt attataacat | 10560 |
| caatcatatc agagtaggac cgataacctcc gaaccccca tcagatggaa ttgcacaaaa | 10620 |
| tgtggggatc gctataactg gtataagctt ttggctgagt ttgatggaga aagacattcc | 10680 |
| actatatcaa cagtgtttag cagttatcca gcaatcattc ccgattaggt gggaggctgt | 10740 |
| ttcagtaaaa ggaggataca agcagaagtg gagtactaga ggtgatggc tcccaaaaga | 10800 |
| tacccgaact tcagactcct tggccccaat cgggaactgg atcagatctc tggaattggt | 10860 |
| ccgaaaccaa gttcgtctaa atccattcaa tgagatcttg ttcaatcagc tatgtcgtac | 10920 |
| agtggataat catttgaaat ggtcaaattt gcgaagaaac acaggaatga ttgaatggat | 10980 |
| caatagcga atttcaaaag aagaccggtc tatactgatg ttgaagagtg acctacgacga | 11040 |
| ggaaaactct tggagagatt aaaaaatcat gaggagactc caaactttaa gtatgaaaaa | 11100 |
| aactttgatc cttaagaccc tcttgtggtt tttatttttt atctggtttt gtggtcttcg | 11160 |
| t | 11161 |

<210> SEQ ID NO 8
<211> LENGTH: 422
<212> TYPE: PRT
<213> ORGANISM: Vesicular stomatitis virus

<400> SEQUENCE: 8

Met Ser Val Thr Val Lys Arg Ile Ile Asp Asn Thr Val Ile Val Pro
1               5                   10                  15

```
Lys Leu Pro Ala Asn Glu Asp Pro Val Glu Tyr Pro Ala Asp Tyr Phe
         20                  25                  30

Arg Lys Ser Lys Glu Ile Pro Leu Tyr Ile Asn Thr Thr Lys Ser Leu
         35                  40                  45

Ser Asp Leu Arg Gly Tyr Val Tyr Gln Gly Leu Lys Ser Gly Asn Val
 50                  55                  60

Ser Ile Ile His Val Asn Ser Tyr Leu Tyr Gly Ala Leu Lys Asp Ile
 65                  70                  75                  80

Arg Gly Lys Leu Asp Lys Asp Trp Ser Ser Phe Gly Ile Asn Ile Gly
             85                  90                  95

Lys Ala Gly Asp Thr Ile Gly Ile Phe Asp Leu Val Ser Leu Lys Ala
            100                 105                 110

Leu Asp Gly Val Leu Pro Asp Gly Val Ser Asp Ala Ser Arg Thr Ser
            115                 120                 125

Ala Asp Asp Lys Trp Leu Pro Leu Tyr Leu Leu Gly Leu Tyr Arg Val
130                 135                 140

Gly Arg Thr Gln Met Pro Glu Tyr Arg Lys Lys Leu Met Asp Gly Leu
145                 150                 155                 160

Thr Asn Gln Cys Lys Met Ile Asn Glu Gln Phe Glu Pro Leu Val Pro
                165                 170                 175

Glu Gly Arg Asp Ile Phe Asp Val Trp Gly Asn Asp Ser Asn Tyr Thr
            180                 185                 190

Lys Ile Val Ala Ala Val Asp Met Phe Phe His Met Phe Lys Lys His
            195                 200                 205

Glu Cys Ala Ser Phe Arg Tyr Gly Thr Ile Val Ser Arg Phe Lys Asp
            210                 215                 220

Cys Ala Ala Leu Ala Thr Phe Gly His Leu Cys Lys Ile Thr Gly Met
225                 230                 235                 240

Ser Thr Glu Asp Val Thr Thr Trp Ile Leu Asn Arg Glu Val Ala Asp
                245                 250                 255

Glu Met Val Gln Met Met Leu Pro Gly Gln Glu Ile Asp Lys Ala Asp
            260                 265                 270

Ser Tyr Met Pro Tyr Leu Ile Asp Phe Gly Leu Ser Ser Lys Ser Pro
            275                 280                 285

Tyr Ser Ser Val Lys Asn Pro Ala Phe His Phe Trp Gly Gln Leu Thr
290                 295                 300

Ala Leu Leu Leu Arg Ser Thr Arg Ala Arg Asn Ala Arg Gln Pro Asp
305                 310                 315                 320

Asp Ile Glu Tyr Thr Ser Leu Thr Thr Ala Gly Leu Leu Tyr Ala Tyr
                325                 330                 335

Ala Val Gly Ser Ser Ala Asp Leu Ala Gln Gln Phe Cys Val Gly Asp
            340                 345                 350

Asn Lys Tyr Thr Pro Asp Asp Ser Thr Gly Gly Leu Thr Thr Asn Ala
            355                 360                 365

Pro Pro Gln Gly Arg Asp Val Val Glu Trp Leu Gly Trp Phe Glu Asp
            370                 375                 380

Gln Asn Arg Lys Pro Thr Pro Asp Met Met Gln Tyr Ala Lys Arg Ala
385                 390                 395                 400

Val Met Ser Leu Gln Gly Leu Arg Glu Lys Thr Ile Gly Lys Tyr Ala
                405                 410                 415

Lys Ser Glu Phe Asp Lys
            420
```

```
<210> SEQ ID NO 9
<211> LENGTH: 265
<212> TYPE: PRT
<213> ORGANISM: Vesicular stomatitis virus

<400> SEQUENCE: 9

Met Asp Asn Leu Thr Lys Val Arg Glu Tyr Leu Lys Ser Tyr Ser Arg
1               5                   10                  15

Leu Asp Gln Ala Val Gly Glu Ile Asp Glu Ile Glu Ala Gln Arg Ala
            20                  25                  30

Glu Lys Ser Asn Tyr Glu Leu Phe Gln Glu Asp Gly Val Glu Glu His
        35                  40                  45

Thr Lys Pro Ser Tyr Phe Gln Ala Ala Asp Asp Ser Asp Thr Glu Ser
    50                  55                  60

Glu Pro Glu Ile Glu Asp Asn Gln Gly Leu Tyr Ala Gln Asp Pro Glu
65                  70                  75                  80

Ala Glu Gln Val Glu Gly Phe Ile Gln Gly Pro Leu Asp Asp Tyr Ala
                85                  90                  95

Asp Glu Glu Val Asp Val Val Phe Thr Ser Asp Trp Lys Pro Pro Glu
            100                 105                 110

Leu Glu Ser Asp Glu His Gly Lys Thr Leu Arg Leu Thr Ser Pro Glu
        115                 120                 125

Gly Leu Ser Gly Glu Gln Lys Ser Gln Trp Leu Ser Thr Ile Lys Ala
    130                 135                 140

Val Val Gln Ser Ala Lys Tyr Trp Asn Leu Ala Glu Cys Thr Phe Glu
145                 150                 155                 160

Ala Ser Gly Glu Gly Val Ile Met Lys Glu Arg Gln Ile Thr Pro Asp
                165                 170                 175

Val Tyr Lys Val Thr Pro Val Met Asn Thr His Pro Ser Gln Ser Glu
            180                 185                 190

Ala Val Ser Asp Val Trp Ser Leu Ser Lys Thr Ser Met Thr Phe Gln
        195                 200                 205

Pro Lys Lys Ala Ser Leu Gln Pro Leu Thr Ile Ser Leu Asp Glu Leu
    210                 215                 220

Phe Ser Ser Arg Gly Glu Phe Ile Ser Val Gly Asp Gly Arg Met
225                 230                 235                 240

Ser His Lys Glu Ala Ile Leu Leu Gly Leu Arg Tyr Lys Lys Leu Tyr
                245                 250                 255

Asn Gln Ala Arg Val Lys Tyr Ser Leu
            260                 265

<210> SEQ ID NO 10
<211> LENGTH: 229
<212> TYPE: PRT
<213> ORGANISM: Vesicular stomatitis virus

<400> SEQUENCE: 10

Met Ser Ser Leu Lys Lys Ile Leu Gly Leu Lys Gly Lys Gly Lys Lys
1               5                   10                  15

Ser Lys Lys Leu Gly Ile Ala Pro Pro Pro Tyr Glu Glu Asp Thr Ser
            20                  25                  30

Met Glu Tyr Ala Pro Ser Ala Pro Ile Asp Lys Ser Tyr Phe Gly Val
        35                  40                  45

Asp Glu Met Asp Thr Tyr Asp Pro Asn Gln Leu Arg Tyr Glu Lys Phe
    50                  55                  60
```

```
Phe Phe Thr Val Lys Met Thr Val Arg Ser Asn Arg Pro Phe Arg Thr
 65                  70                  75                  80

Tyr Ser Asp Val Ala Ala Val Ser His Trp Asp His Met Tyr Ile
             85                  90                  95

Gly Met Ala Gly Lys Arg Pro Phe Tyr Lys Ile Leu Ala Phe Leu Gly
            100                 105                 110

Ser Ser Asn Leu Lys Ala Thr Pro Ala Val Leu Ala Asp Gln Gly Gln
            115                 120                 125

Pro Glu Tyr His Thr His Cys Glu Gly Arg Ala Tyr Leu Pro His Arg
        130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Ile Glu Leu Thr Met Thr
                165                 170                 175

Ile Tyr Asp Asp Glu Ser Leu Glu Ala Ala Pro Met Ile Trp Asp His
            180                 185                 190

Phe Asn Ser Ser Lys Phe Ser Asp Phe Arg Glu Lys Ala Leu Met Phe
        195                 200                 205

Gly Leu Ile Val Glu Lys Lys Ala Ser Gly Ala Trp Val Leu Asp Ser
210                 215                 220

Ile Ser His Phe Lys
225

<210> SEQ ID NO 11
<211> LENGTH: 511
<212> TYPE: PRT
<213> ORGANISM: Vesicular stomatitis virus

<400> SEQUENCE: 11

Met Lys Cys Leu Leu Tyr Leu Ala Phe Leu Phe Ile Gly Val Asn Cys
  1               5                  10                  15

Lys Phe Thr Ile Val Phe Pro His Asn Gln Lys Gly Asn Trp Lys Asn
             20                  25                  30

Val Pro Ser Asn Tyr His Tyr Cys Pro Ser Ser Ser Asp Leu Asn Trp
         35                  40                  45

His Asn Asp Leu Ile Gly Thr Ala Ile Gln Val Lys Met Pro Lys Ser
 50                  55                  60

His Lys Ala Ile Gln Ala Asp Gly Trp Met Cys His Ala Ser Lys Trp
 65                  70                  75                  80

Val Thr Thr Cys Asp Phe Arg Trp Tyr Gly Pro Lys Tyr Ile Thr Gln
             85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
            115                 120                 125

Ser Cys Gly Tyr Ala Thr Val Thr Asp Ala Glu Ala Val Ile Val Gln
        130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205
```

Gly Glu Leu Ser Ser Leu Gly Lys Glu Gly Thr Gly Phe Arg Ser Asn
        210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
        435                 440                 445

Asn Pro Ile Glu Leu Val Glu Gly Trp Phe Ser Ser Trp Lys Ser Ser
450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510

<210> SEQ ID NO 12
<211> LENGTH: 2109
<212> TYPE: PRT
<213> ORGANISM: Vesicular stomatitis virus

<400> SEQUENCE: 12

Met Glu Val His Asp Phe Glu Thr Asp Glu Phe Asn Asp Phe Asn Glu
1               5                   10                  15

Asp Asp Tyr Ala Thr Arg Glu Phe Leu Asn Pro Asp Glu Arg Met Thr
            20                  25                  30

Tyr Leu Asn His Ala Asp Tyr Asn Leu Asn Ser Pro Leu Ile Ser Asp
        35                  40                  45

Asp Ile Asp Asn Leu Ile Arg Lys Phe Asn Ser Leu Pro Ile Pro Ser
    50                  55                  60

Met Trp Asp Ser Lys Asn Trp Asp Gly Val Leu Glu Met Leu Thr Ser

-continued

```
                65                  70                  75                  80
Cys Gln Ala Asn Pro Ile Ser Thr Ser Gln Met His Lys Trp Met Gly
                        85                  90                  95
Ser Trp Leu Met Ser Asp Asn His Asp Ala Ser Gln Gly Tyr Ser Phe
                        100                 105                 110
Leu His Glu Val Asp Lys Glu Ala Glu Ile Thr Phe Asp Val Val Glu
                        115                 120                 125
Thr Phe Ile Arg Gly Trp Gly Asn Lys Pro Ile Glu Tyr Ile Lys Lys
            130                 135                 140
Glu Arg Trp Thr Asp Ser Phe Lys Ile Leu Ala Tyr Leu Cys Gln Lys
145                 150                 155                 160
Phe Leu Asp Leu His Lys Leu Thr Leu Ile Leu Asn Ala Val Ser Glu
                165                 170                 175
Val Glu Leu Leu Asn Leu Ala Arg Thr Phe Lys Gly Lys Val Arg Arg
                180                 185                 190
Ser Ser His Gly Thr Asn Ile Cys Arg Ile Arg Val Pro Ser Leu Gly
                195                 200                 205
Pro Thr Phe Ile Ser Glu Gly Trp Ala Tyr Phe Lys Lys Leu Asp Ile
        210                 215                 220
Leu Met Asp Arg Asn Phe Leu Leu Met Val Lys Asp Val Ile Ile Gly
225                 230                 235                 240
Arg Met Gln Thr Val Leu Ser Met Val Cys Arg Ile Asp Asn Leu Phe
                245                 250                 255
Ser Glu Gln Asp Ile Phe Ser Leu Leu Asn Ile Tyr Arg Ile Gly Asp
                260                 265                 270
Lys Ile Val Glu Arg Gln Gly Asn Phe Ser Tyr Asp Leu Ile Lys Met
        275                 280                 285
Val Glu Pro Ile Cys Asn Leu Lys Leu Met Lys Leu Ala Arg Glu Ser
        290                 295                 300
Arg Pro Leu Val Pro Gln Phe Pro His Phe Glu Asn His Ile Lys Thr
305                 310                 315                 320
Ser Val Asp Glu Gly Ala Lys Ile Asp Arg Gly Ile Arg Phe Leu His
                325                 330                 335
Asp Gln Ile Met Ser Val Lys Thr Val Asp Leu Thr Leu Val Ile Tyr
                340                 345                 350
Gly Ser Phe Arg His Trp Gly His Pro Phe Ile Asp Tyr Tyr Thr Gly
            355                 360                 365
Leu Glu Lys Leu His Ser Gln Val Thr Met Lys Lys Asp Ile Asp Val
        370                 375                 380
Ser Tyr Ala Lys Ala Leu Ala Ser Asp Leu Ala Arg Ile Val Leu Phe
385                 390                 395                 400
Gln Gln Phe Asn Asp His Lys Lys Trp Phe Val Asn Gly Asp Leu Leu
                405                 410                 415
Pro His Asp His Pro Phe Lys Ser His Val Lys Glu Asn Thr Trp Pro
                420                 425                 430
Thr Ala Ala Gln Val Gln Asp Phe Gly Asp Lys Trp His Glu Leu Pro
            435                 440                 445
Leu Ile Lys Cys Phe Glu Ile Pro Asp Leu Leu Asp Pro Ser Ile Ile
        450                 455                 460
Tyr Ser Asp Lys Ser His Ser Met Asn Arg Ser Glu Val Leu Lys His
465                 470                 475                 480
Val Arg Met Asn Pro Asn Thr Pro Ile Pro Ser Lys Lys Val Leu Gln
                485                 490                 495
```

```
Thr Met Leu Asp Thr Lys Ala Thr Asn Trp Lys Glu Phe Leu Lys Glu
            500                 505                 510
Ile Asp Glu Lys Gly Leu Asp Asp Asp Leu Ile Ile Gly Leu Lys
            515                 520                 525
Gly Lys Glu Arg Glu Leu Lys Leu Ala Gly Arg Phe Phe Ser Leu Met
530                 535                 540
Ser Trp Lys Leu Arg Glu Tyr Phe Val Ile Thr Glu Tyr Leu Ile Lys
545                 550                 555                 560
Thr His Phe Val Pro Met Phe Lys Gly Leu Thr Met Ala Asp Asp Leu
            565                 570                 575
Thr Ala Val Ile Lys Lys Met Leu Asp Ser Ser Gly Gln Gly Leu
            580                 585                 590
Lys Ser Tyr Glu Ala Ile Cys Ile Ala Asn His Ile Asp Tyr Glu Lys
            595                 600                 605
Trp Asn Asn His Gln Arg Lys Leu Ser Asn Gly Pro Val Phe Arg Val
            610                 615                 620
Met Gly Gln Phe Leu Gly Tyr Pro Ser Leu Ile Glu Arg Thr His Glu
625                 630                 635                 640
Phe Phe Glu Lys Ser Leu Ile Tyr Tyr Asn Gly Arg Pro Asp Leu Met
                645                 650                 655
Arg Val His Asn Asn Thr Leu Ile Asn Ser Thr Ser Gln Arg Val Cys
            660                 665                 670
Trp Gln Gly Gln Glu Gly Gly Leu Glu Gly Leu Arg Gln Lys Gly Trp
            675                 680                 685
Thr Ile Leu Asn Leu Leu Val Ile Gln Arg Glu Ala Lys Ile Arg Asn
            690                 695                 700
Thr Ala Val Lys Val Leu Ala Gln Gly Asp Asn Gln Val Ile Cys Thr
705                 710                 715                 720
Gln Tyr Lys Thr Lys Lys Ser Arg Asn Val Val Glu Leu Gln Gly Ala
                725                 730                 735
Leu Asn Gln Met Val Ser Asn Asn Glu Lys Ile Met Thr Ala Ile Lys
            740                 745                 750
Ile Gly Thr Gly Lys Leu Gly Leu Leu Ile Asn Asp Asp Glu Thr Met
            755                 760                 765
Gln Ser Ala Asp Tyr Leu Asn Tyr Gly Lys Ile Pro Ile Phe Arg Gly
770                 775                 780
Val Ile Arg Gly Leu Glu Thr Lys Arg Trp Ser Arg Val Thr Cys Val
785                 790                 795                 800
Thr Asn Asp Gln Ile Pro Thr Cys Ala Asn Ile Met Ser Ser Val Ser
                805                 810                 815
Thr Asn Ala Leu Thr Val Ala His Phe Ala Glu Asn Pro Ile Asn Ala
            820                 825                 830
Met Ile Gln Tyr Asn Tyr Phe Gly Thr Phe Ala Arg Leu Leu Leu Met
            835                 840                 845
Met His Asp Pro Ala Leu Arg Gln Ser Leu Tyr Glu Val Gln Asp Lys
            850                 855                 860
Ile Pro Gly Leu His Ser Ser Thr Phe Lys Tyr Ala Met Leu Tyr Leu
865                 870                 875                 880
Asp Pro Ser Ile Gly Gly Val Ser Gly Met Ser Leu Ser Arg Phe Leu
                885                 890                 895
Ile Arg Ala Phe Pro Asp Pro Val Thr Glu Ser Leu Ser Phe Trp Arg
            900                 905                 910
```

```
Phe Ile His Val His Ala Arg Ser Glu His Leu Lys Glu Met Ser Ala
            915                 920                 925
Val Phe Gly Asn Pro Glu Ile Ala Lys Phe Arg Ile Thr His Ile Asp
930                 935                 940
Lys Leu Val Glu Asp Pro Thr Ser Leu Asn Ile Ala Met Gly Met Ser
945                 950                 955                 960
Pro Ala Asn Leu Leu Lys Thr Glu Val Lys Lys Cys Leu Ile Glu Ser
            965                 970                 975
Arg Gln Thr Ile Arg Asn Gln Val Ile Lys Asp Ala Thr Ile Tyr Leu
            980                 985                 990
Tyr His Glu Glu Asp Arg Leu Arg Ser Phe Leu Trp Ser Ile Asn Pro
            995                 1000                1005
Leu Phe Pro Arg Phe Leu Ser Glu Phe Lys Ser Gly Thr Phe Leu
    1010                1015                1020
Gly Val Ala Asp Gly Leu Ile Ser Leu Phe Gln Asn Ser Arg Thr
    1025                1030                1035
Ile Arg Asn Ser Phe Lys Lys Lys Tyr His Arg Glu Leu Asp Asp
    1040                1045                1050
Leu Ile Val Arg Ser Glu Val Ser Ser Leu Thr His Leu Gly Lys
    1055                1060                1065
Leu His Leu Arg Arg Gly Ser Cys Lys Met Trp Thr Cys Ser Ala
    1070                1075                1080
Thr His Ala Asp Thr Leu Arg Tyr Lys Ser Trp Gly Arg Thr Val
    1085                1090                1095
Ile Gly Thr Thr Val Pro His Pro Leu Glu Met Leu Gly Pro Gln
    1100                1105                1110
His Arg Lys Glu Thr Pro Cys Ala Pro Cys Asn Thr Ser Gly Phe
    1115                1120                1125
Asn Tyr Val Ser Val His Cys Pro Asp Gly Ile His Asp Val Phe
    1130                1135                1140
Ser Ser Arg Gly Pro Leu Pro Ala Tyr Leu Gly Ser Lys Thr Ser
    1145                1150                1155
Glu Ser Thr Ser Ile Leu Gln Pro Trp Glu Arg Glu Ser Lys Val
    1160                1165                1170
Pro Leu Ile Lys Arg Ala Thr Arg Leu Arg Asp Ala Ile Ser Trp
    1175                1180                1185
Phe Val Glu Pro Asp Ser Lys Leu Ala Met Thr Ile Leu Ser Asn
    1190                1195                1200
Ile His Ser Leu Thr Gly Glu Glu Trp Thr Lys Arg Gln His Gly
    1205                1210                1215
Phe Lys Arg Thr Gly Ser Ala Leu His Arg Phe Ser Thr Ser Arg
    1220                1225                1230
Met Ser His Gly Gly Phe Ala Ser Gln Ser Thr Ala Ala Leu Thr
    1235                1240                1245
Arg Leu Met Ala Thr Thr Asp Thr Met Arg Asp Leu Gly Asp Gln
    1250                1255                1260
Asn Phe Asp Phe Leu Phe Gln Ala Thr Leu Leu Tyr Ala Gln Ile
    1265                1270                1275
Thr Thr Thr Val Ala Arg Asp Gly Trp Ile Thr Ser Cys Thr Asp
    1280                1285                1290
His Tyr His Ile Ala Cys Lys Ser Cys Leu Arg Pro Ile Glu Glu
    1295                1300                1305
Ile Thr Leu Asp Ser Ser Met Asp Tyr Thr Pro Pro Asp Val Ser
```

```
                1310                1315                1320
His Val Leu Lys Thr Trp Arg Asn Gly Glu Gly Ser Trp Gly Gln
                1325                1330                1335
Glu Ile Lys Gln Ile Tyr Pro Leu Glu Gly Asn Trp Lys Asn Leu
                1340                1345                1350
Ala Pro Ala Glu Gln Ser Tyr Gln Val Gly Arg Cys Ile Gly Phe
                1355                1360                1365
Leu Tyr Gly Asp Leu Ala Tyr Arg Lys Ser Thr His Ala Glu Asp
                1370                1375                1380
Ser Ser Leu Phe Pro Leu Ser Ile Gln Gly Arg Ile Arg Gly Arg
                1385                1390                1395
Gly Phe Leu Lys Gly Leu Leu Asp Gly Leu Met Arg Ala Ser Cys
                1400                1405                1410
Cys Gln Val Ile His Arg Arg Ser Leu Ala His Leu Lys Arg Pro
                1415                1420                1425
Ala Asn Ala Val Tyr Gly Gly Leu Ile Tyr Leu Ile Asp Lys Leu
                1430                1435                1440
Ser Val Ser Pro Pro Phe Leu Ser Leu Thr Arg Ser Gly Pro Ile
                1445                1450                1455
Arg Asp Glu Leu Glu Thr Ile Pro His Lys Ile Pro Thr Ser Tyr
                1460                1465                1470
Pro Thr Ser Asn Arg Asp Met Gly Val Ile Val Arg Asn Tyr Phe
                1475                1480                1485
Lys Tyr Gln Cys Arg Leu Ile Glu Lys Gly Lys Tyr Arg Ser His
                1490                1495                1500
Tyr Ser Gln Leu Trp Leu Phe Ser Asp Val Leu Ser Ile Asp Phe
                1505                1510                1515
Ile Gly Pro Phe Ser Ile Ser Thr Thr Leu Leu Gln Ile Leu Tyr
                1520                1525                1530
Lys Pro Phe Leu Ser Gly Lys Asp Lys Asn Glu Leu Arg Glu Leu
                1535                1540                1545
Ala Asn Leu Ser Ser Leu Leu Arg Ser Gly Glu Gly Trp Glu Asp
                1550                1555                1560
Ile His Val Lys Phe Phe Thr Lys Asp Ile Leu Leu Cys Pro Glu
                1565                1570                1575
Glu Ile Arg His Ala Cys Lys Phe Gly Ile Ala Lys Asp Asn Asn
                1580                1585                1590
Lys Asp Met Ser Tyr Pro Pro Trp Gly Arg Glu Ser Arg Gly Thr
                1595                1600                1605
Ile Thr Thr Ile Pro Val Tyr Tyr Thr Thr Pro Tyr Pro Lys
                1610                1615                1620
Met Leu Glu Met Pro Pro Arg Ile Gln Asn Pro Leu Leu Ser Gly
                1625                1630                1635
Ile Arg Leu Gly Gln Leu Pro Thr Gly Ala His Tyr Lys Ile Arg
                1640                1645                1650
Ser Ile Leu His Gly Met Gly Ile His Tyr Arg Asp Phe Leu Ser
                1655                1660                1665
Cys Gly Asp Gly Ser Gly Gly Met Thr Ala Ala Leu Leu Arg Glu
                1670                1675                1680
Asn Val His Ser Arg Gly Ile Phe Asn Ser Leu Leu Glu Leu Ser
                1685                1690                1695
Gly Ser Val Met Arg Gly Ala Ser Pro Glu Pro Pro Ser Ala Leu
                1700                1705                1710
```

```
Glu Thr Leu Gly Gly Asp Lys Ser Arg Cys Val Asn Gly Glu Thr
1715                1720                1725

Cys Trp Glu Tyr Pro Ser Asp Leu Cys Asp Pro Arg Thr Trp Asp
1730                1735                1740

Tyr Phe Leu Arg Leu Lys Ala Gly Leu Gly Leu Gln Ile Asp Leu
1745                1750                1755

Ile Val Met Asp Met Glu Val Arg Asp Ser Ser Thr Ser Leu Lys
1760                1765                1770

Ile Glu Thr Asn Val Arg Asn Tyr Val His Arg Ile Leu Asp Glu
1775                1780                1785

Gln Gly Val Leu Ile Tyr Lys Thr Tyr Gly Thr Tyr Ile Cys Glu
1790                1795                1800

Ser Glu Lys Asn Ala Val Thr Ile Leu Gly Pro Met Phe Lys Thr
1805                1810                1815

Val Asp Leu Val Gln Thr Glu Phe Ser Ser Gln Thr Ser Glu
1820                1825                1830

Val Tyr Met Val Cys Lys Gly Leu Lys Lys Leu Ile Asp Glu Pro
1835                1840                1845

Asn Pro Asp Trp Ser Ser Ile Asn Glu Ser Trp Lys Asn Leu Tyr
1850                1855                1860

Ala Phe Gln Ser Ser Glu Gln Glu Phe Ala Arg Ala Lys Lys Val
1865                1870                1875

Ser Thr Tyr Phe Thr Leu Thr Gly Ile Pro Ser Gln Phe Ile Pro
1880                1885                1890

Asp Pro Phe Val Asn Ile Glu Thr Met Leu Gln Ile Phe Gly Val
1895                1900                1905

Pro Thr Gly Val Ser His Ala Ala Ala Leu Lys Ser Ser Asp Arg
1910                1915                1920

Pro Ala Asp Leu Leu Thr Ile Ser Leu Phe Tyr Met Ala Ile Ile
1925                1930                1935

Ser Tyr Tyr Asn Ile Asn His Ile Arg Val Gly Pro Ile Pro Pro
1940                1945                1950

Asn Pro Pro Ser Asp Gly Ile Ala Gln Asn Val Gly Ile Ala Ile
1955                1960                1965

Thr Gly Ile Ser Phe Trp Leu Ser Leu Met Glu Lys Asp Ile Pro
1970                1975                1980

Leu Tyr Gln Gln Cys Leu Ala Val Ile Gln Gln Ser Phe Pro Ile
1985                1990                1995

Arg Trp Glu Ala Val Ser Val Lys Gly Gly Tyr Lys Gln Lys Trp
2000                2005                2010

Ser Thr Arg Gly Asp Gly Leu Pro Lys Asp Thr Arg Thr Ser Asp
2015                2020                2025

Ser Leu Ala Pro Ile Gly Asn Trp Ile Arg Ser Leu Glu Leu Val
2030                2035                2040

Arg Asn Gln Val Arg Leu Asn Pro Phe Asn Glu Ile Leu Phe Asn
2045                2050                2055

Gln Leu Cys Arg Thr Val Asp Asn His Leu Lys Trp Ser Asn Leu
2060                2065                2070

Arg Arg Asn Thr Gly Met Ile Glu Trp Ile Asn Arg Arg Ile Ser
2075                2080                2085

Lys Glu Asp Arg Ser Ile Leu Met Leu Lys Ser Asp Leu His Glu
2090                2095                2100
```

Glu Asn Ser Trp Arg Asp
        2105

<210> SEQ ID NO 13
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 13
gtgcgtggaa gaccggtacc tcccatttgg                              30

<210> SEQ ID NO 14
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 14
taatgttatt gccggcgaat tcgaaactga ataaatc                       37

<210> SEQ ID NO 15
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 15
aataacatta ctcgagttcg gtacctccca tttgg                         35

<210> SEQ ID NO 16
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 16
caactttaaa ttcgaaactg aataaatcta tc                            32

<210> SEQ ID NO 17
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 17
taatacgact cactatagg                                           19

<210> SEQ ID NO 18
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 18
acggagaaaa acaaaccaat tcacgc                                   26

<210> SEQ ID NO 19
<211> LENGTH: 36
<212> TYPE: DNA

```
<213> ORGANISM: Artificial Sequence
<220> FEATURE:
<223> OTHER INFORMATION: Synthetic oligonucleotide

<400> SEQUENCE: 19
ttgagcacct ggtacaggta tgaattgatg tgacac                                36

<210> SEQ ID NO 20
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 20
gcgtgaattg gtttgttttt ctccgtccta tagtgagtcg tattagccgg cctcgagtaa      60
attaatt                                                               67

<210> SEQ ID NO 21
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 21
ttgagcacct ggtacaggta tgaattgatg tgacac                                36

<210> SEQ ID NO 22
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 22
cgtattagcc ggcctcgagt aaattaatt                                        29

<210> SEQ ID NO 23
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 23
aatctggacg cgtctcgcta gtcaggctga ttatttgagg                            40

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 24
ttgatatttc cccaactcta c                                                21

<210> SEQ ID NO 25
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 25
```
cgcatgccgt ctccttatgt tgattg        26

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 26
agcattcatt ataagtatga c        21

<210> SEQ ID NO 27
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 27
gcttttcaca gatgaagcta gctgaaagta tgaaaaaaac g        41

<210> SEQ ID NO 28
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 28 gttttttca tactttcagc tagcttcatc tgtgaaaagc ttg        43

<210> SEQ ID NO 29
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 29
aacagaggtc aaacgcgtgt caaaatgact tcagttttat tcatg        45

<210> SEQ ID NO 30
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 30
gaataaaact gaagtcattt tgacacgcgt ttgacctctg ttaat        45

<210> SEQ ID NO 31
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 31
cagctggcgg ccgctaggaa ttcaaatcaa catatatgaa aaaaatcaac agagatacaa        60
caatg        65

<210> SEQ ID NO 32

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 32
acatagtggc attgtgaaca g                                       21

<210> SEQ ID NO 33
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 33
cgcatgccgt ctccttatgt tgattg                                  26

<210> SEQ ID NO 34
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 34
agtcataccg gtctcgttaa ttttttttcat atctttcttc tgcatgttat aattc  55

<210> SEQ ID NO 35
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 35
tcgagaacgc gtttgacctc tgttaatttt tttcatatat gttgatttga attc   54

<210> SEQ ID NO 36
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 36
attccaacgc gtctcgttaa cagggatcaa aatgacttct gtagtaaag         49

<210> SEQ ID NO 37
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 37
gcttttcaca gatgaagcta gcgcatgcgg ccgctgaaag tatgaaaaaa acg    53

<210> SEQ ID NO 38
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 38
```

```
gttttttttca tactttcagc ggccgcatgc gctagcttca tctgtgaaaa gcttg          55
```

<210> SEQ ID NO 39
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 39

```
ctagctgaaa gtatgaaaaa aattaacaga ggtcaaactc gaggatatcg gtaccgaagg     60
cgcgcccagc tgtgcggcc                                                  79
```

<210> SEQ ID NO 40
<211> LENGTH: 75
<212> TYPE: DNA
<213> ORGANISM: Artificial Sequence
<220> FEATURE:
<223> OTHER INFORMATION: Synthetic oligonucleotide

<400> SEQUENCE: 40

```
ggccgcacag ctgggcgcgc cttcggtacc gatatcctcg agtttgacct ctgttaattt     60
ttttcatact ttcag                                                      75
```

<210> SEQ ID NO 41
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 41

```
gaattcctcg agttgacctc tgttaatttt tttcatatat gttgatttga attc           54
```

<210> SEQ ID NO 42
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 42

```
gatgaagcta gctgaaagta tgaaaaaaat taacagggat caaaatgact tctgtag        57
```

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 43

```
atcattcctt tatttgtcag c                                               21
```

<210> SEQ ID NO 44
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 44

```
tatatggcta gcgaagacag agggatcaaa atgtctcgac tcaaccaaat                50
```

<210> SEQ ID NO 45
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 45
ctagcccggc taatacgact cactataggg cggagaaaaa caaa            44

<210> SEQ ID NO 46
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 46
ttggtttgtt tttctccgtc ctatagtgag tcgtattagc cggcg           45

<210> SEQ ID NO 47
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 47
ccaattcacg cattagaaga ttccagagga aagtgctaac                 40

<210> SEQ ID NO 48
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 48
ccctgttagc actttcctct ggaatcttct aatgcgtgaa                 40

<210> SEQ ID NO 49
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 49
gaaagacaag aagtggacca gagcgattcc tacatgcctt acatgattga tatggggatc    60
tcaaccaaat c                                                        71

<210> SEQ ID NO 50
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 50
ggttgagatc cccatatcaa tcatgtaagg catgtaggaa tcgctctggt ccacttcttg    60
tctttctttc                                                          70

<210> SEQ ID NO 51
<211> LENGTH: 117

```
<212> TYPE: PRT
<213> ORGANISM: Artificial Sequence
<220> FEATURE:
<223> OTHER INFORMATION: Synthetic polypeptide

<400> SEQUENCE: 51

Met Val Ala Arg Ala Ser Val Leu Gly Gly Glu Leu Asp Arg Trp Glu
1               5                   10                  15
Lys Glu Glu Glu Arg Pro Gly Gly Lys Lys Tyr Lys Leu Lys Glu
            20                  25                  30
Glu Glu Trp Ala Ser Arg Glu Leu Glu Arg Phe Ala Val Asn Pro Gly
        35                  40                  45
Leu Glu Thr Ser Glu Gly Cys Arg Gln Ile Gly His Gln Ala Ala
    50                  55                  60
Met Gln Met Leu Lys Glu Thr Ile Asn Glu Glu Ala Ala Ile Leu Lys
65                  70                  75                  80
Ala Leu Gly Pro Ala Ala Thr Leu Glu Glu Met Met Thr Ala Cys Gln
                85                  90                  95
Gly Val Gly Gly Tyr Pro Tyr Asp Val Pro Asp Tyr Ala Pro Gly His
            100                 105                 110
Lys Ala Arg Val Leu
        115

<210> SEQ ID NO 52
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 52

Ala Met Gln Met Leu Lys Glu Thr Ile
1               5

<210> SEQ ID NO 53
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 53 tttttttgcta gcttcacctg cataatagtg gcaac                              35

<210> SEQ ID NO 54
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 54
aacagaggtc aaacgcgtgt caaaatgact tcagttttat tcatg                    45

<210> SEQ ID NO 55
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 55
gtgcgtatga aaaaaacgaa tcaacagagt tcatcatgga tgagtactct gaagaaaagt    60
```
ggggcgattc                                                              70

<210> SEQ ID NO 56
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 56

Met Asp Glu Tyr Ser Glu Glu Lys Trp Gly Asp
1               5                   10

<210> SEQ ID NO 57
<211> LENGTH: 137
<212> TYPE: DNA
<213> ORGANISM: Artificial Sequence
<220> FEATURE:
<223> OTHER INFORMATION: Synthetic oligonucleotide

<400> SEQUENCE: 57
gtgcaggtga gctagccgcc tagccagatt ctatgtttgg accaaatcaa cttgtgatac      60
catgctcaaa gaggcctcat tatatttgag tttttaattt ttatgaaaaa aacgaatcaa     120
cagagttcat catggat                                                   137

<210> SEQ ID NO 58
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 58
ctattatgcg tatgcgagac gcgtctcgta tgaaaaaaac gaatcaacag ag              52

<210> SEQ ID NO 59
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 59
ctgttgattc gttttttttca tacgagacgc gtctcgcata cgcataatag tg             52

<210> SEQ ID NO 60
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 60
aattaacgtc tcagagattg cagcgaaccc cagtgcggct gctgtttctt tc              52

<210> SEQ ID NO 61
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 61
aacagaggtc aaacgcgtgt caaaatgact tcagttttat tcatg                      45

-continued

<210> SEQ ID NO 62
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 62
tctctgtgat cctgatcatc ggactgatga ggctgctgcc actactgtgc aggtgag    57

<210> SEQ ID NO 63
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 63
ctagctcacc tgcacagtag tggcagcagc ctcatcagtc cgatgatcag gatcaca    57

<210> SEQ ID NO 64
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 64
ctaggcgcgt ctcgcatacg cacagtagtg gcag    34

<210> SEQ ID NO 65
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 65
aacagaggtc aaacgcgtgt caaaatgact tcagttttat tcatg    45

<210> SEQ ID NO 66
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 66
tgttagcgtc tctcataaaa attaaaaact caaatataat tg    42

<210> SEQ ID NO 67
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 67
aacagaggtc aaacgcgtgt caaaatgact tcagttttat tcatg    45

<210> SEQ ID NO 68
<211> LENGTH: 18
<212> TYPE: PRT
<213> ORGANISM: Thosea asigna virus

<400> SEQUENCE: 68

Glu Gly Arg Gly Ser Leu Leu Thr Cys Gly Asp Val Glu Glu Asn Pro
1               5                   10                  15

Gly Pro

<210> SEQ ID NO 69
<211> LENGTH: 37
<212> TYPE: DNA
<213> ORGANISM: Artificial Sequence
<220> FEATURE:
<223> OTHER INFORMATION: Synthetic Primer

<400> SEQUENCE: 69
gggcccactc gagaacatga gcctggccat ccccgtg                              37

<210> SEQ ID NO 70
<211> LENGTH: 37
<212> TYPE: DNA
<213> ORGANISM: Artificial Sequence
<220> FEATURE:
<223> OTHER INFORMATION: Synthetic Primer

<400> SEQUENCE: 70
gggcccagct agcggccgct tagtgcctgc tgaagct                              37

<210> SEQ ID NO 71
<211> LENGTH: 423
<212> TYPE: PRT
<213> ORGANISM: Vesicular stomatitis virus

<400> SEQUENCE: 71

Met Thr Ser Val Val Lys Arg Ile Ala Thr Gly Ser Ser Val Leu Ala
1               5                   10                  15

Val Leu Pro Ala Asn Glu Asp Pro Val Glu Phe Pro Gly Asp Tyr Phe
                20                  25                  30

Leu Gln Asn Pro Gly Lys Ile Arg Val Cys Ile Asn Arg Lys Leu Asp
            35                  40                  45

Val Ala Thr Leu Arg Gln Tyr Val Tyr Glu Gly Leu Lys Asn Gly Asp
        50                  55                  60

Val His Val Cys His Ile Asn Ser Tyr Leu Tyr Gln Val Leu Lys Asp
65                  70                  75                  80

Thr Arg Asp Glu Ala Gln Ser Asp Trp Ile Ser Phe Gly Val Ser Leu
                85                  90                  95

Ala Val Lys Gly Gly Ile Val Ser Val Phe Asp Thr Leu Met Ile Glu
            100                 105                 110

Asp Tyr Arg Gly Glu Ala Pro Asp Gly Arg Lys Cys Asp Gly Arg Thr
        115                 120                 125

Ile Asp Asp Asp Lys Trp Leu Pro Met Leu Ile Leu Gly Leu Tyr Arg
    130                 135                 140

Val Ser Arg Ala Thr Gln Glu Asp Tyr Lys Lys Ser Leu Leu Gln Lys
145                 150                 155                 160

Leu Tyr Ala Gln Cys Lys Leu Arg Ser Pro Gln Ala Glu Glu Leu Val
                165                 170                 175

Glu Asp Ala Ala Glu Phe Tyr Glu Val Trp Ser Asn Asp Ser Asn Phe
            180                 185                 190

Leu Lys Leu Val Ala Ala Ile Asp Met Phe Phe His Lys Phe Lys Asn
        195                 200                 205

His Ala Asp Ala Gly Leu Arg Trp Gly Thr Ile Val Ser Arg Phe Lys

```
            210                 215                 220
Asp Cys Ala Ala Leu Ala Thr Leu Ser His Val Gln Lys Val Thr Gly
225                 230                 235                 240

Leu Ser Ile Lys Glu Val Phe Thr Trp Val Leu Asn Lys Ser Val Glu
                245                 250                 255

Asp Glu Leu Cys Arg Met Met Lys Glu Arg Gln Glu Val Asp Lys Ala
            260                 265                 270

Asp Ser Tyr Met Pro Tyr Leu Ile Asp Phe Gly Ile Ser Thr Lys Ser
                275                 280                 285

Pro Tyr Ser Ser Val Lys Asn Pro Cys Phe His Phe Trp Gly Gln Leu
            290                 295                 300

Thr Ala Leu Leu Val His Ser His Arg Ala Lys Asn Ala Arg Val Pro
305                 310                 315                 320

Glu Asp Ile Pro Tyr Asn Glu Leu Thr Thr Ala Ala Trp Leu Phe Ala
                325                 330                 335

Tyr Ala Met Gly Arg Ser Ser Gly Leu Glu Gln Arg Phe Thr Thr Asp
            340                 345                 350

Asp Ser Tyr Tyr Gln Glu Asp Glu Ile Asn Lys Gly Leu Gly Val
                355                 360                 365

Lys Ala Pro Thr Thr Arg Asp Val Gln Met Trp Leu Ala Trp Trp Ser
            370                 375                 380

Asp Ile Gly Lys Val Pro Thr Gln Asp Met Glu Thr Phe Ala Arg Arg
385                 390                 395                 400

Glu Val Leu Gly Leu Thr Glu Ile Arg Ser Lys Thr Ile Gly Glu Tyr
                405                 410                 415

Ala Lys Lys Thr Phe Ser Val
            420

<210> SEQ ID NO 72
<211> LENGTH: 423
<212> TYPE: PRT
<213> ORGANISM: Vesicular stomatitis virus

<400> SEQUENCE: 72

Met Ser Val Thr Val Lys Arg Ile Ile Asp Asn Thr Val Val Pro
1               5                   10                  15

Lys Leu Pro Ala Asn Glu Asp Pro Val Glu Tyr Pro Ala Asp Tyr Phe
                20                  25                  30

Arg Lys Ser Lys Glu Ile Pro Leu Tyr Ile Asn Thr Thr Ser Lys Leu
            35                  40                  45

Ser Asp Leu Arg Gly Tyr Val Tyr Gln Gly Leu Lys Ser Gly Asn Val
        50                  55                  60

Ser Ile Ile His Val Asn Ser Tyr Leu Tyr Gly Ala Leu Lys Asp Ile
65                  70                  75                  80

Arg Gly Lys Leu Asp Lys Asp Trp Ser Ser Phe Gly Ile Asn Ile Gly
                85                  90                  95

Lys Ala Lys Gly Asp Thr Ile Gly Ile Phe Asp Leu Val Ser Leu Lys
            100                 105                 110

Ala Leu Asp Gly Val Leu Pro Asp Gly Val Ser Asp Ala Ser Arg Thr
        115                 120                 125

Ser Ala Asp Asp Lys Trp Leu Pro Leu Tyr Leu Leu Gly Leu Tyr Arg
    130                 135                 140

Val Gly Arg Thr Gln Met Pro Glu Tyr Arg Lys Lys Leu Met Asp Gly
145                 150                 155                 160
```

```
Leu Thr Asn Gln Cys Lys Met Ile Asn Glu Gln Phe Glu Pro Leu Val
                165                 170                 175

Pro Glu Gly Arg Asp Ile Phe Asp Val Trp Gly Asn Asp Ser Asn Tyr
            180                 185                 190

Thr Lys Ile Val Ala Ala Val Asp Met Phe Phe His Met Phe Lys Lys
        195                 200                 205

His Glu Cys Ala Ser Phe Arg Tyr Gly Thr Ile Val Ser Arg Phe Lys
    210                 215                 220

Asp Cys Ala Ala Leu Ala Thr Phe Gly His Leu Cys Lys Ile Thr Gly
225                 230                 235                 240

Met Ser Thr Glu Asp Val Thr Thr Trp Ile Leu Asn Arg Glu Val Ala
                245                 250                 255

Asp Glu Met Val Gln Met Met Leu Pro Gly Gln Glu Ile Asp Lys Ala
            260                 265                 270

Asp Ser Tyr Met Pro Tyr Leu Ile Asp Phe Gly Leu Ser Ser Lys Ser
        275                 280                 285

Pro Tyr Ser Ser Val Lys Asn Pro Ala Phe His Phe Trp Gly Gln Leu
    290                 295                 300

Thr Ala Leu Leu Leu Arg Ser Thr Arg Ala Arg Asn Ala Arg Gln Pro
305                 310                 315                 320

Asp Asp Ile Glu Tyr Thr Ser Leu Thr Thr Ala Gly Leu Leu Tyr Ala
                325                 330                 335

Tyr Ala Val Gly Ser Ser Ala Asp Leu Ala Gln Gln Phe Cys Val Gly
            340                 345                 350

Asp Asn Lys Tyr Thr Pro Asp Asp Ser Thr Gly Gly Leu Thr Thr Asn
        355                 360                 365

Ala Pro Pro Gln Gly Arg Asp Val Val Glu Trp Leu Gly Trp Phe Glu
    370                 375                 380

Asp Gln Asn Arg Lys Pro Thr Pro Asp Met Met Gln Tyr Ala Lys Arg
385                 390                 395                 400

Ala Val Met Ser Leu Gln Gly Leu Arg Glu Lys Thr Ile Gly Lys Tyr
                405                 410                 415

Ala Lys Ser Glu Phe Asp Lys
            420

<210> SEQ ID NO 73
<211> LENGTH: 422
<212> TYPE: PRT
<213> ORGANISM: Vesicular stomatitis virus

<400> SEQUENCE: 73

Met Ala Pro Thr Val Lys Arg Ile Ile Asn Asp Ser Ile Ile Gln Pro
1               5                   10                  15

Lys Leu Pro Ala Asn Glu Asp Pro Val Glu Tyr Pro Ala Asp Tyr Phe
            20                  25                  30

Glu Asn Asn Thr Asn Ile Val Leu Tyr Val Asn Thr Lys Val Ala Leu
        35                  40                  45

Asn Asp Leu Arg Ala Tyr Val Tyr Gln Gly Ile Lys Ser Gly Asn Pro
    50                  55                  60

Ser Ile Leu His Ile Asn Ala Tyr Leu Tyr Ala Ala Leu Lys Gly Val
65                  70                  75                  80

Glu Gly Thr Leu Asp Arg Asp Trp Val Ser Phe Gly Arg Thr Ile Gly
                85                  90                  95

Lys Arg Glu Glu Asn Val Lys Ile Phe Asp Leu Val Lys Val Glu Glu
            100                 105                 110
```

```
Leu Lys Thr Ala Leu Pro Asp Gly Lys Ser Asp Pro Asp Arg Ser Ala
            115                 120                 125

Glu Asp Asp Lys Trp Leu Pro Ile Tyr Ile Leu Gly Leu Tyr Arg Val
        130                 135                 140

Gly Arg Ser Lys Val Thr Asp Tyr Arg Lys Lys Leu Leu Asp Gly Leu
145                 150                 155                 160

Glu Asn Gln Cys Arg Val Ala Ser Thr Arg Phe Glu Ser Leu Val Glu
                165                 170                 175

Asp Gly Leu Asp Phe Phe Asp Ile Trp Glu Asn Asp Pro Asn Phe Thr
            180                 185                 190

Lys Ile Val Ala Ala Val Asp Met Phe Phe His Met Phe Lys Lys His
        195                 200                 205

Glu Arg Ala Pro Ile Arg Tyr Gly Thr Ile Val Ser Arg Phe Lys Asp
    210                 215                 220

Cys Ala Ala Leu Ala Thr Phe Gly His Leu Ser Lys Val Ser Gly Leu
225                 230                 235                 240

Ser Ile Glu Asp Leu Thr Thr Trp Val Leu Asn Arg Glu Val Ala Asp
                245                 250                 255

Glu Leu Cys Gln Met Met Tyr Pro Gly Gln Glu Ile Asp Lys Ala Asp
            260                 265                 270

Ser Tyr Met Pro Tyr Met Ile Asp Phe Gly Leu Ser Gln Lys Ser Pro
        275                 280                 285

Tyr Ser Val Lys Asn Pro Ala Phe His Phe Trp Gly Gln Leu Ala
    290                 295                 300

Ala Leu Leu Leu Arg Ser Thr Arg Ala Lys Asn Ala Arg Gln Pro Asp
305                 310                 315                 320

Asp Ile Glu Tyr Thr Ser Leu Thr Cys Ala Ser Leu Leu Ser Phe
                325                 330                 335

Ala Val Gly Ser Ser Ala Asp Ile Glu Gln Gln Phe Tyr Ile Gly Glu
            340                 345                 350

Asp Lys Tyr Thr Thr Glu Lys Asp Asp Ser Leu Lys Lys Ser Asp Val
        355                 360                 365

Pro Pro Lys Gly Arg Asn Val Val Asp Trp Leu Gly Trp Tyr Asp Asp
    370                 375                 380

Asn Gly Gly Lys Pro Thr Pro Asp Met Leu Asn Phe Ala Arg Arg Ala
385                 390                 395                 400

Val Ser Ser Leu Gln Ser Leu Arg Glu Lys Thr Ile Gly Lys Tyr Ala
                405                 410                 415

Lys Val Glu Phe Asp Lys
            420

<210> SEQ ID NO 74
<211> LENGTH: 422
<212> TYPE: PRT
<213> ORGANISM: Chandipura virus

<400> SEQUENCE: 74

Met Ser Ser Gln Val Phe Cys Ile Ser Thr Gly Gln Thr Val Ser Val
1               5                   10                  15

Cys Leu Pro Ala Asn Glu Asp Pro Val Glu Phe Pro Gly Ala Phe Phe
            20                  25                  30

Thr Pro Asn Ala Arg Lys Pro Thr Val Tyr Ile Lys Lys Glu Thr Asp
        35                  40                  45

Leu Ser Leu Leu Arg Ser His Val Tyr Asp Gly Ile Lys Asp Gly Ser
```

```
                 50                  55                  60
Val Thr Val Ser Gln Ile Asn Ser Tyr Leu Tyr Met Val Leu Lys Asp
 65                  70                  75                  80

Ile Arg Glu Lys Pro Asp Lys Asn Trp Thr Ser Phe Gly Val Glu Leu
                 85                  90                  95

Gly Lys Lys Asn Glu Pro Met Gly Ile Phe Asp Leu Leu Asn Val Glu
                100                 105                 110

Asp Val Lys Gly Lys Glu Leu Asp Lys Gly Gln Asp Thr Arg Leu
                115                 120                 125

Pro Gly Asp Asp Leu Trp Leu Pro Thr Leu Ile Phe Gly Leu Tyr Arg
    130                 135                 140

Val Ser Arg Ala Thr Gln Val Glu Tyr Lys Lys Thr Leu Met Thr Asn
145                 150                 155                 160

Leu Tyr Ala Gln Cys Lys Leu Arg Thr Lys Asp Ala Glu Glu Ile Val
                165                 170                 175

Asp Glu Thr Ala Glu Phe Phe Asn Ala Trp Ala Asn Asp Ser Asn Phe
                180                 185                 190

Thr Lys Ile Val Ala Ala Val Asp Met Tyr Phe His His Phe Lys Lys
                195                 200                 205

Ser Asp His Ala Pro Ile Arg Phe Gly Thr Ile Val Ser Arg Phe Lys
    210                 215                 220

Asp Cys Ala Ala Leu Ser Thr Leu Ser His Leu Gln Lys Val Thr Gly
225                 230                 235                 240

Leu Pro Ile Glu Glu Val Phe Thr Trp Val Phe Asn Lys Ser Val Gln
                245                 250                 255

Asp Asp Leu Leu Arg Met Met Thr Pro Gly Gln Glu Ile Asp Gln Ala
                260                 265                 270

Asp Ser Tyr Met Pro Tyr Leu Ile Asp Met Gly Leu Ser Thr Lys Ser
                275                 280                 285

Pro Tyr Ser Ser Thr Lys Asn Pro Ser Phe His Phe Trp Gly Gln Leu
    290                 295                 300

Thr Ala Phe Leu Val Lys Ser Ala Arg Ala Lys Asn Ala Leu Val Pro
305                 310                 315                 320

Val Asp Ile Ala Tyr His Glu Leu Thr Thr Ala Ala Leu Leu Phe Ala
                325                 330                 335

Tyr Ala Ile Gly Arg Ser Ser Glu Leu Glu Gln Arg Phe Val Leu Asn
                340                 345                 350

Gly Lys Lys Phe Thr Lys Glu Lys Asp Ser Arg Glu Asp Asn Asp Thr
                355                 360                 365

Thr Pro Pro Ser Glu Arg Asn Val Val Val Trp Leu Ala Trp Trp Glu
    370                 375                 380

Asp Ile Lys His Glu Ile Thr Pro Asp Met Lys Ala Phe Ala Lys Arg
385                 390                 395                 400

Ala Val Glu Arg Val Gly Asp Ile Arg Val Asn Ser Val Ala Glu Tyr
                405                 410                 415

Ala Arg Lys Leu Phe Ala
                420

<210> SEQ ID NO 75
<211> LENGTH: 427
<212> TYPE: PRT
<213> ORGANISM: Piry virus

<400> SEQUENCE: 75
```

-continued

```
Met Ser Val Ser Val Lys Arg Ile Ser Thr Gly Thr Gln Val Val Ala
1               5                   10                  15

Ala Leu Pro Ala Ser Glu Asp Pro Val Glu Phe Pro Ala Glu Tyr Phe
            20                  25                  30

Ala Lys Asn Pro Gly Lys Ile Pro Val Phe Ile Ser Thr Arg Leu Asp
            35                  40                  45

Leu Asp Lys Leu Arg Gln Tyr Val Tyr Met Gly Leu Thr Thr Gly Glu
        50                  55                  60

Val Asn Val Cys His Ile Asn Ser Tyr Leu Tyr Arg Val Leu Gln Asn
65                  70                  75                  80

Ile Glu Asp Glu Ala Arg Asp Asn Trp Val Ser Phe Arg Val Thr Ile
                85                  90                  95

Ala Ala Lys Asp Thr Thr Val Arg Leu Phe Asp Met Leu Glu Val Lys
            100                 105                 110

Glu Tyr Ala Gly Leu Val Pro Asp Gly Lys Glu Asn Ala Asn Leu Thr
            115                 120                 125

Gln Thr Val Asp Glu Trp Leu Pro Met Tyr Ile Leu Gly Leu Gln Arg
        130                 135                 140

Val Gly Arg Ala Thr Asp Glu Arg Tyr Arg Gly Asp Leu Tyr Asp His
145                 150                 155                 160

Leu Cys Ala Gln Cys Lys Leu Lys Ser Pro Ser Phe Glu Ser Leu Gly
                165                 170                 175

Asn Pro Ala Asp Asn Asn Tyr Ala Ser Trp Ile Asn Asp Ser Asn Phe
            180                 185                 190

Leu Lys Leu Val Ala Ala Ile Asp Met Phe Phe His His Phe Lys Lys
        195                 200                 205

His Glu Glu Ala Val Ile Arg Phe Gly Thr Ile Thr Ser Arg Phe Lys
    210                 215                 220

Asp Cys Ala Ala Leu Ser Thr Met Ala His Leu Val Lys Val Thr Gly
225                 230                 235                 240

Met Pro Val Glu Glu Val Met Thr Trp Val Leu Asn Lys Pro Val Glu
                245                 250                 255

Asp Glu Val Cys Arg Met Met Thr Pro Gly Gln Glu Ile Asp Lys Ala
            260                 265                 270

Asp Ser Tyr Met Pro Tyr Leu Ile Asp Phe Gly Leu Ser Thr Lys Ser
        275                 280                 285

Pro Tyr Ser Ser Val Lys Asn Pro Cys Phe His Phe Trp Gly Gln Leu
        290                 295                 300

Thr Ala Val Leu Val Asn Ser Ala Arg Ala Arg Asn Ala Arg Val Pro
305                 310                 315                 320

Asp Asp Ile Pro Tyr Gln Glu Leu Thr Gln Ala Ala Leu Leu Phe Ala
                325                 330                 335

Tyr Ala Thr Gly Arg Ser Ser Asp Leu Ala Gln Arg Phe Val Leu His
            340                 345                 350

Asn Lys Glu Tyr Ile Lys Ala Ala Pro Asp Ala Ser Asp Asn Ser Glu
        355                 360                 365

Arg Glu Glu Ser Lys Glu Ala Pro Thr Thr Arg Asp Val Val Glu Trp
    370                 375                 380

Leu Ala Trp Trp Asp Asp Ile Gly Gln Val Arg Thr Arg Asp Met Glu
385                 390                 395                 400

Val Phe Ala Arg Arg Ala Val His Gly Ile Leu Asp Pro Arg Glu Lys
                405                 410                 415

Ser Ile Gly Ala Tyr Ala Arg Gly Tyr Phe Ala
```

<210> SEQ ID NO 76
<211> LENGTH: 422
<212> TYPE: PRT
<213> ORGANISM: Vesicular stomatitis virus

<400> SEQUENCE: 76

Met Ala Ala Thr Val Lys Arg Val Ile Asp Asp Ser Val Ile Thr Pro
1               5                   10                  15

Lys Leu Pro Ala Asn Glu Asp Pro Val Glu Tyr Pro Ala Asp Tyr Phe
            20                  25                  30

Lys Lys Ser Arg Asp Ile Pro Val Tyr Ile Asn Thr Thr Lys Ser Leu
        35                  40                  45

Ala Asp Leu Arg Gly Tyr Val Tyr Gln Gly Leu Lys Ala Gly Ser Leu
    50                  55                  60

Ser Ile Val His Val Asn Ser Tyr Leu Tyr Ala Ala Leu Lys Asp Val
65                  70                  75                  80

Lys Gly Lys Leu Asp Arg Asp Trp Ile Thr Phe Asn Ile Gln Ile Gly
                85                  90                  95

Lys Ala Gly Asp Asn Val Gly Ile Phe Asp Leu Val Thr Val Lys Asn
            100                 105                 110

Leu Glu Gly Val Cys Pro Asp Gly Val Ser Asp Ala Thr Arg Thr Ser
        115                 120                 125

Ala Asp Asp Gln Trp Leu Pro Leu Tyr Leu Leu Gly Leu Tyr Arg Val
    130                 135                 140

Gly Arg Thr Gln Met Thr Asp Tyr Arg Lys Lys Leu Met Asp Gly Leu
145                 150                 155                 160

Ile Ala Gln Cys Lys Leu Ile Asn Glu Lys Phe Glu Pro Leu Ile Pro
                165                 170                 175

Glu Gly Arg Asp Phe Tyr Asp Ile Trp Gly Asn Asp Gly Asn Tyr Thr
            180                 185                 190

Lys Ile Val Ala Ala Val Asp Met Phe Phe His Met Phe Lys Lys His
        195                 200                 205

Glu Lys Ala Ser Phe Arg Tyr Gly Thr Ile Val Ser Arg Phe Lys Asp
    210                 215                 220

Cys Ala Ala Leu Ala Thr Phe Gly His Val Cys Lys Ile Thr Gly Met
225                 230                 235                 240

Ser Thr Glu Glu Val Thr Thr Trp Ile Leu Asn Arg Glu Val Ala Asp
                245                 250                 255

Glu Met Val Gln Met Met Tyr Pro Gly Gln Glu Ile Asp Lys Ser Asp
            260                 265                 270

Ser Tyr Met Pro Tyr Leu Ile Asp Leu Gly Leu Ser Gln Lys Ser Pro
        275                 280                 285

Tyr Ser Thr Val Lys Asn Pro Ala Phe His Phe Trp Gly Gln Leu Thr
    290                 295                 300

Ala Leu Leu Leu Arg Ser Thr Arg Ala Arg Asn Ala Arg Gln Pro Asp
305                 310                 315                 320

Asp Ile Glu Tyr Thr Ser Leu Thr Thr Ala Gly Leu Leu Tyr Ala Tyr
                325                 330                 335

Ala Val Gly Ser Ser Ala Asp Leu Ser Gln Gln Phe Tyr Val Gly Asp
            340                 345                 350

Asp Lys Tyr Ile Ser Glu Asn Thr Thr Gly Gly Leu Asn Ser Asn Ala
        355                 360                 365

```
Pro Pro Gln Gly Arg Asp Val Val Glu Trp Leu Gly Trp Phe Asp Asp
    370                 375                 380

Asn Gln Arg Lys Pro Thr Ala Asp Met Leu Gln Tyr Ala Lys Lys Ala
385                 390                 395                 400

Val Met Ser Leu Gln Gly Leu Arg Asp Lys Thr Ile Gly Lys Tyr Ala
                405                 410                 415

Lys Ala Glu Phe Asp Lys
                420

<210> SEQ ID NO 77
<211> LENGTH: 422
<212> TYPE: PRT
<213> ORGANISM: Vesicular stomatitis virus

<400> SEQUENCE: 77

Met Ala Val Val Lys Arg Ile Ile Asp Asp Thr Leu Ile Val Pro
1               5                   10                  15

Lys Leu Pro Ala Ser Glu Asp Pro Val Glu Tyr Pro Ala Asp Tyr Phe
                20                  25                  30

Lys Lys Thr Ser Glu Ile Pro Leu Phe Ile Asn Thr Thr Lys Ser Leu
                35                  40                  45

Ala Glu Leu Arg Gly Phe Val Tyr Gln Gly Leu Lys Ser Gly Val Val
        50                  55                  60

Ser Ile Ile His Val Asn Ser Tyr Leu Tyr Ala Ala Leu Lys Asp Val
65                  70                  75                  80

Gln Ala Lys Leu Asp Arg Asp Trp Thr Ser Phe Gly Val Asn Ile Gly
                85                  90                  95

Arg Ala Gly Ala Asn Val Gly Ile Phe Asp Leu Val Ser Val Lys Gly
                100                 105                 110

Leu Glu Gly Val Cys Pro Asp Gly Val Ser Asp Ala Ser Arg Thr Ser
            115                 120                 125

Ala Asp Asp Asn Trp Leu Pro Leu Tyr Leu Leu Gly Leu Tyr Arg Val
        130                 135                 140

Gly Arg Thr Gln Met Thr Asp Tyr Arg Lys Arg Leu Met Asp Gly Leu
145                 150                 155                 160

Ile Asn Gln Cys Lys Met Ile Asp Asp Lys Phe Glu Pro Leu Ile Pro
                165                 170                 175

Glu Gly Arg Asp Phe Phe Asp Leu Trp Gly Asn Asp Asn Asn Tyr Thr
            180                 185                 190

Lys Ile Ile Ala Ala Val Asp Met Phe Phe His Met Phe Lys Lys His
        195                 200                 205

Glu Arg Ala Tyr Leu Arg Tyr Gly Thr Ile Val Ser Arg Phe Lys Asp
210                 215                 220

Cys Ala Ala Leu Ala Thr Phe Gly His Val Cys Lys Ile Thr Gly Met
225                 230                 235                 240

Ser Thr Glu Glu Val Thr Thr Trp Ile Leu Asn Arg Glu Val Gly Asp
                245                 250                 255

Glu Met Ile Gln Met Met Lys Pro Gly Gln Glu Ile Asp Lys Ala Asp
            260                 265                 270

Ser Tyr Met Pro Tyr Leu Ile Asp Phe Gly Leu Ser Gln Lys Ser Pro
        275                 280                 285

Tyr Ser Thr Val Lys Asn Pro Ala Phe His Phe Trp Gly Gln Leu Thr
    290                 295                 300

Ala Leu Leu Leu Arg Ser Thr Arg Ala Lys Asn Ala Arg Gln Pro Asp
305                 310                 315                 320
```

```
Asp Ile Glu Tyr Thr Ser Leu Thr Thr Ala Gly Leu Leu Tyr Ala Tyr
                325                 330                 335

Ala Val Gly Ser Ser Ala Asp Leu Thr Gln Gln Phe Tyr Met Gly Asp
            340                 345                 350

Asn Lys Tyr Val Pro Asp Asn Ser Asp Gly Gly Leu Thr Thr Asn Ala
            355                 360                 365

Pro Pro Gln Gly Arg Asp Val Val Glu Trp Leu Gly Trp Phe Asp Asp
    370                 375                 380

Asn His Arg Lys Pro Thr Pro Asp Met Leu Gln Tyr Ala Lys Arg Ala
385                 390                 395                 400

Val Met Ser Leu Gln Gly Leu Arg Asp Lys Thr Ile Gly Lys Tyr Ala
                405                 410                 415

Lys Ser Glu Phe Asp Lys
            420

<210> SEQ ID NO 78
<211> LENGTH: 418
<212> TYPE: PRT
<213> ORGANISM: V

```
                    260                 265                 270
Met Pro Tyr Leu Ile Asp Met Gly Ile Ser Ala Lys Ser Pro Tyr Ser
                275                 280                 285

Thr Ile Lys Asn Pro Ser Phe His Phe Trp Gly Gln Leu Val Ala Ala
            290                 295                 300

Leu Cys Arg Ser Lys Arg Ala Leu Asn Ala Arg Gln Pro Asp Glu Ile
305                 310                 315                 320

Asp Ser Met Ser Ile Ser Asn Ala Ser Leu Leu Met Ala Tyr Ala Leu
                325                 330                 335

Gly Ser Ser Pro Asp Ile Glu Gln Gln Phe Ser Thr Gly Asp Thr Tyr
            340                 345                 350

Arg Lys Pro Pro Lys Glu Ala Ser Tyr Leu Val Ser Glu Glu Pro Lys
        355                 360                 365

Asn Arg Ser Val Val Glu Trp Ile Ala Trp Tyr Ser Asp Val Asp Asn
    370                 375                 380

Lys Pro Thr Asp Asp Met Leu Met Met Ala Lys Arg Val Ala Gly Thr
385                 390                 395                 400

Val Ser Gly Pro Arg Asp Asn Ser Val Gly Lys Trp Ile Lys Gln Thr
                405                 410                 415

Tyr Gly

<210> SEQ ID NO 79
<211> LENGTH: 419
<212> TYPE: PRT
<213> ORGANISM: Vesicular stomatitis virus

<400> SEQUENCE: 79

Met Ser Val Ile Arg Ile Lys Thr Asn Ala Ala Val Ala Ala Val Leu
1               5                   10                  15

Pro Ala Asn Glu Asp Gln Ala Asp Tyr Pro Ala Thr Phe Phe Glu Gly
            20                  25                  30

Gly Asn Glu Ile Arg Leu Tyr Val His Arg Gly Glu Lys Leu Asp Val
        35                  40                  45

Leu Arg Gln Tyr Val Tyr Met Gly Leu Gln Glu Lys Asn Cys Lys Ile
    50                  55                  60

Gln His Val Asn Ala Tyr Leu Tyr Glu Val Leu Lys Gly Glu Glu Glu
65                  70                  75                  80

Arg Leu Glu Ala Asp Trp Asp Ser Phe Gly Gln Lys Ile Gly Asn Gln
                85                  90                  95

Gly Glu Lys Ile Gly Pro Phe Lys Leu Val Lys Val Gly Asp Ile Thr
            100                 105                 110

Glu Gly Leu Pro Asp Gly Lys Leu Asn Ala Glu Val Ser Ala Glu Asp
        115                 120                 125

Asp Ala Trp Leu Pro Leu Phe Leu Leu Gly Leu Tyr Arg Val Gly Arg
    130                 135                 140

Ala Ser Glu Thr Ala Tyr Arg Thr Leu Leu Met Glu Ala Leu Ile Lys
145                 150                 155                 160

Gln Cys Lys Ala Ile Lys Ser Asp Trp Val Ser Pro Val Thr Ser Thr
                165                 170                 175

His Lys Tyr Phe Asp Val Trp Gly Asn Asp Gly Asn Tyr Leu Lys Ile
            180                 185                 190

Val Ala Cys Val Asp Met Phe Tyr Asn His Phe Lys Lys Ser Ile Lys
        195                 200                 205

Ala Thr Phe Arg Trp Gly Thr Ile Val Ser Arg Phe Lys Asp Cys Ala
```

```
            210                 215                 220
Ala Leu Ala Thr Leu Gly His Leu Val Lys Ile Thr Gly Leu Thr Ile
225                 230                 235                 240

Glu Glu Val Phe Thr Trp Val Leu Gln Thr Glu Val Ala Asp Glu Leu
                245                 250                 255

Val Arg Met Met Lys Pro Gly Gln Glu Ile Asp Asn Gly Ala Ser Tyr
            260                 265                 270

Met Pro Tyr Leu Ile Asp Met Gly Ile Ser Ala Lys Ser Pro Tyr Ser
        275                 280                 285

Thr Ile Lys Asn Pro Ser Phe His Phe Trp Gly Gln Leu Thr Ser Ala
    290                 295                 300

Leu Cys Arg Ser Lys Arg Ala Leu Asn Ala Arg Gln Pro Asp Glu Ile
305                 310                 315                 320

Asp Ser Val Ser Ile Ser Asn Ala Gly Leu Leu Met Ala Tyr Ala Leu
                325                 330                 335

Gly Ser Ser Pro Asp Ile Glu Gln Gln Phe Ser Thr Gly Asp Thr Tyr
            340                 345                 350

Arg Lys Pro Pro Lys Glu Gly Ser Tyr Leu Val Thr Glu Glu Pro Lys
        355                 360                 365

Thr Arg Ala Val Val Asp Trp Ile Ala Trp Tyr Ser Asp Val Asp Asn
    370                 375                 380

Lys Pro Thr Asp Glu Met Leu Leu Met Ala Lys Arg Val Ala Gly Thr
385                 390                 395                 400

Ile Ser Gly Pro Arg Glu Asn Ser Val Gly Lys Trp Ile Lys Gln Thr
                405                 410                 415

Tyr Gly Gln

<210> SEQ ID NO 80
<211> LENGTH: 426
<212> TYPE: PRT
<213> ORGANISM: Vesicular stomatitis virus

<400> SEQUENCE: 80

Met Asp Asn Ser Leu Val Val Arg Ala Thr Lys Ala Ala Phe Val
1               5                   10                  15

Pro Val Arg Pro Lys Leu Glu Asp Glu Val Asn Tyr Pro Ser Glu Phe
            20                  25                  30

Phe Val Asp Gly Lys Ile Pro Ala Phe Leu His Tyr Tyr Ala Asp Lys
        35                  40                  45

Thr Gln Ala Glu Leu Leu Gly Met Ile Phe Gly Glu Leu Ser Glu Ser
    50                  55                  60

Arg Leu Pro Ser Glu Leu Val Thr Ser Tyr Leu Tyr Asn Val Ile Lys
65                  70                  75                  80

Asp Trp Val Glu Lys Leu Asp Ala Ala Trp Glu Ser Tyr Gly Thr Thr
                85                  90                  95

Ile Gly Asp Leu Asn Glu Val Ile Asn Ala Phe Ser Leu Met Ser Tyr
            100                 105                 110

Gln Val Ala Ala Gln Pro Leu Pro Asp Tyr Lys Val Gly Ala Val Pro
        115                 120                 125

Ala Asp Ile Asp Pro Val Ala Met Val Ile Phe Leu Ala Pro Tyr
    130                 135                 140

Arg Ile Val Gly Ile Gln Asn Glu Glu Tyr Gln Thr Arg Val Met Gln
145                 150                 155                 160

Thr Ile Gln Asn Gln Leu Asp Ser Leu Gly Ala Lys Lys Leu Ser Val
```

```
                165                 170                 175
Arg Gln Leu Lys Asn Ile Thr Thr Leu Thr Lys Ser Pro Asn Tyr Leu
            180                 185                 190

Lys Val Ala Ala Val Asp Met Phe Tyr Phe His Phe Lys Asn Asn
            195                 200                 205

Asn Glu Lys Ala Val Val Arg Val Ser Thr Leu Gly Ser Arg His Arg
            210                 215                 220

Asp Cys Ala Ala Leu Ala Thr Leu Asn His Ile Val Gln Phe Thr Gly
225                 230                 235                 240

Leu Thr Leu Leu Glu Val Leu Asp Trp Val Phe Thr Asp Gln Val Ala
            245                 250                 255

Met Glu Ile Ala Arg Met Met His Pro Asn Gln Glu Ile Asp Gln Ala
            260                 265                 270

Asp Ser Tyr Met Pro Tyr Leu Lys Asp Phe Gly Leu Cys Arg Lys Ser
            275                 280                 285

Pro Tyr Ser Ser Ala Asn Pro Gly Thr His Cys Trp Ala Gln Met
            290                 295                 300

Thr Cys Ala Leu Leu Gly Ser Lys Arg Ser Gln Asn Ala Ile Ala Asn
305                 310                 315                 320

Thr Glu Glu Asn Leu Val Asn Leu Thr Arg Asn Ala Glu Ile Met Ala
            325                 330                 335

Cys Val Leu Gly Thr Gly Ala Thr Leu Val Lys Ala Ile Glu Ile Asn
            340                 345                 350

Gly Val Thr Gly Ser Glu Asp Asp Asp Ala Thr Glu Glu Asp Gly
            355                 360                 365

Thr Ala Glu Pro Thr Ser Met Glu Ala Leu Asp Trp Leu Asp Tyr Val
            370                 375                 380

Lys Ala Asn Asn Cys Gln Leu Thr Pro Lys Met Glu Ala Arg Val His
385                 390                 395                 400

Met Met Ser Gln Arg Ile Gln His Ala Arg Lys Asp Thr Val Gly Ala
            405                 410                 415

Tyr Leu Lys Ala Arg Val Ser Ala Asp His
            420                 425

<210> SEQ ID NO 81
<211> LENGTH: 35
<212> TYPE: PRT
<213> ORGANISM: Chandipura virus

<400> SEQUENCE: 81

Met Met Thr Pro Gly Gln Glu Ile Asp Gln Ala Asp Ser Tyr Met Pro
1               5                   10                  15

Tyr Leu Ile Asp Met Gly Leu Ser Thr Lys Ser Pro Tyr Ser Ser Thr
            20                  25                  30

Lys Asn Pro
        35

<210> SEQ ID NO 82
<211> LENGTH: 35
<212> TYPE: PRT
<213> ORGANISM: Piry virus

<400> SEQUENCE: 82

Met Met Thr Pro Gly Gln Glu Ile Asp Lys Ala Asp Ser Tyr Met Pro
1               5                   10                  15

Tyr Leu Ile Asp Phe Gly Leu Ser Thr Lys Ser Pro Tyr Ser Ser Val
```

-continued

```
<210> SEQ ID NO 83
<211> LENGTH: 35
<212> TYPE: PRT
<213> ORGANISM: Cocal virus

<400> SEQUENCE: 83

Met Met Tyr Pro Gly Gln Glu Ile Asp Lys Ser Asp Ser Tyr Met Pro
1               5                   10                  15

Tyr Leu Ile Asp Leu Gly Leu Ser Gln Lys Ser Pro Tyr Ser Thr Val
            20                  25                  30

Lys Asn Pro
        35

<210> SEQ ID NO 84
<211> LENGTH: 35
<212> TYPE: PRT
<213> ORGANISM: Vesicular stomatitis virus

<400> SEQUENCE: 84

Met Met Lys Pro Gly Gln Glu Ile Asp Lys Ala Asp Ser Tyr Met Pro
1               5                   10                  15

Tyr Leu Ile Asp Phe Gly Leu Ser Gln Lys Ser Pro Tyr Ser Thr Val
            20                  25                  30

Lys Asn Pro
        35

<210> SEQ ID NO 85
<211> LENGTH: 35
<212> TYPE: PRT
<213> ORGANISM: Spring viremia of carp virus

<400> SEQUENCE: 85

Met Met Lys Pro Gly Gln Glu Ile Asp Lys Ser Thr Ser Tyr Met Pro
1               5                   10                  15

Tyr Leu Ile Asp Met Gly Ile Ser Ala Lys Ser Pro Tyr Ser Thr Ile
            20                  25                  30

Lys Asn Pro
        35

<210> SEQ ID NO 86
<211> LENGTH: 35
<212> TYPE: PRT
<213> ORGANISM: Vesicular stomatitis virus

<400> SEQUENCE: 86

Met Met Lys Pro Gly Gln Glu Ile Asp Asn Gly Ala Ser Tyr Met Pro
1               5                   10                  15

Tyr Leu Ile Asp Met Gly Ile Ser Ala Lys Ser Pro Tyr Ser Thr Ile
            20                  25                  30

Lys Asn Pro
        35

<210> SEQ ID NO 87
<211> LENGTH: 35
<212> TYPE: PRT
<213> ORGANISM: Vesicular stomatitis virus
```

```
<400> SEQUENCE: 87

Met Met Tyr Pro Gly Gln Glu Ile Asp Lys Ala Asp Ser Tyr Met Pro
1               5                   10                  15

Tyr Met Ile Asp Phe Gly Leu Ser Gln Lys Ser Pro Tyr Ser Ser Val
            20                  25                  30

Lys Asn Pro
        35

<210> SEQ ID NO 88
<211> LENGTH: 35
<212> TYPE: PRT
<213> ORGANISM: Vesicular stomatitis virus

<400> SEQUENCE: 88

Met Met Leu Pro Gly Gln Glu Ile Asp Lys Ala Asp Ser Tyr Met Pro
1               5                   10                  15

Tyr Leu Ile Asp Phe Gly Leu Ser Ser Lys Ser Pro Tyr Ser Ser Val
            20                  25                  30

Lys Asn Pro
        35

<210> SEQ ID NO 89
<211> LENGTH: 35
<212> TYPE: PRT
<213> ORGANISM: Vesicular stomatitis virus

<400> SEQUENCE: 89

Met Met Lys Glu Arg Gln Glu Val Asp Lys Ala Asp Ser Tyr Met Pro
1               5                   10                  15

Tyr Leu Ile Asp Phe Gly Ile Ser Thr Lys Ser Pro Tyr Ser Ser Val
            20                  25                  30

Lys Asn Pro
        35

<210> SEQ ID NO 90
<211> LENGTH: 35
<212> TYPE: PRT
<213> ORGANISM: Vesicular stomatitis virus

<400> SEQUENCE: 90

Met Met Lys Glu Arg Gln Glu Val Asp Gln Ser Asp Ser Tyr Met Pro
1               5                   10                  15

Tyr Met Ile Asp Met Gly Ile Ser Thr Lys Ser Pro Tyr Ser Ser Val
            20                  25                  30

Lys Asn Pro
        35
```